US012595231B2

(12) United States Patent
Protzko et al.

(10) Patent No.: US 12,595,231 B2
(45) Date of Patent: *Apr. 7, 2026

(54) CRYSTALLINE SALT FORMS OF MESEMBRINE

(71) Applicant: Kanna Health Limited, Kent (GB)

(72) Inventors: Ryan Joseph Protzko, Marriottsville, MD (US); Royston Anthony Gray, Essex (GB)

(73) Assignee: Kanna Health Ltd, Kent (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/614,136

(22) Filed: Mar. 22, 2024

(65) Prior Publication Data

US 2024/0409512 A1 Dec. 12, 2024

Related U.S. Application Data

(63) Continuation of application No. 18/129,725, filed on Mar. 31, 2023, now Pat. No. 11,970,446.

(30) Foreign Application Priority Data

Apr. 1, 2022 (GB) ..................................... 2204778

(51) Int. Cl.
*C07D 209/12* (2006.01)

(52) U.S. Cl.
CPC ........ *C07D 209/12* (2013.01); *C07B 2200/13* (2013.01)

(58) Field of Classification Search
CPC .................................................... C07D 209/12
See application file for complete search history.

(56) References Cited

U.S. PATENT DOCUMENTS 3,536,809 A 10/1970 Applezweig et al.
3,598,123 A 8/1971 Zaffaroni
3,710,795 A 1/1973 Higuchi et al.
3,845,770 A 11/1974 Theeuwes et al.
3,916,899 A 11/1975 Theeuwes et al.
RE28,819 E 5/1976 Thompson
4,008,719 A 2/1977 Theeuwes et al.
4,044,126 A 8/1977 Cook et al.
4,328,245 A 5/1982 Yu et al.
4,358,603 A 11/1982 Yu
4,364,923 A 12/1982 Cook et al.
4,409,239 A 10/1983 Yu
4,410,545 A 10/1983 Yu et al.
4,414,209 A 11/1983 Cook et al.
4,522,811 A 6/1985 Eppstein et al.
5,033,252 A 7/1991 Carter
5,052,558 A 10/1991 Carter
5,059,595 A 10/1991 Le Grazie
5,073,543 A 12/1991 Marshall et al.
5,120,548 A 6/1992 McClelland et al.
5,323,907 A 6/1994 Kalvelage
5,354,556 A 10/1994 Sparks et al.
5,591,767 A 1/1997 Mohr et al.
5,639,476 A 6/1997 Oshlack et al.
5,639,480 A 6/1997 Bodmer et al.
5,674,533 A 10/1997 Santus et al.
5,709,874 A 1/1998 Hanson et al.
5,733,566 A 3/1998 Lewis
5,739,108 A 4/1998 Mitchell
5,759,542 A 6/1998 Gurewich
5,840,674 A 11/1998 Yatvin et al.
5,860,957 A 1/1999 Jacobsen et al.
5,891,474 A 4/1999 Busetti et al.
5,900,252 A 5/1999 Calanchi et al.
5,922,356 A 7/1999 Koseki et al.
5,948,433 A 9/1999 Burton et al.
5,972,366 A 10/1999 Haynes et al.
5,972,891 A 10/1999 Kamei et al.
5,980,945 A 11/1999 Ruiz
5,983,134 A 11/1999 Ostrow
5,985,307 A 11/1999 Hanson et al.
5,985,317 A 11/1999 Venkateshwaran et al.
5,993,855 A 11/1999 Yoshimoto et al.
6,004,534 A 12/1999 Langer et al.
6,010,715 A 1/2000 Wick et al.
6,024,975 A 2/2000 D'Angelo et al.
6,039,975 A 3/2000 Shah et al.
6,045,830 A 4/2000 Igari et al.
6,048,736 A 4/2000 Kosak (Continued)

FOREIGN PATENT DOCUMENTS

WO WO-9746234 A1 12/1997
WO WO-2005025506 A2 3/2005

(Continued)

OTHER PUBLICATIONS

Anonymous: "Can Kanna Delay Ejaculation", www.boostmood.com, Sep. 14, 2017, 4 pages.
Bancroft et al., "Three years' experience in a sexual problems clinic". British Medical Journal. Jun. 6, 1976; 1(6025):3 pages.
Berge et al., "Pharmaceutical salts". Journal of pharmaceutical sciences. Jan. 1, 1977;66(1): 1-19.
Bharte et al., "Carboxylic acid counterions in FDA-approved pharmaceutical salts". Pharmaceutical Research. Aug. 2021;38:1307-26.
Bodendorf et al., "Über die Alkaloide von Mesembryanthemum tortuosum", L. Archiv der Pharmazie. 1957; 290(10): 441-8.
Brunetti Pietro et al: "Pharmacology of Herbal Sexual Enhancers: A Review of Psychiatric and Neurological Adverse Effects", Pharmaceuticals, vol. 13, No. 10, Oct. 14, 2020 (Oct. 14, 2020), p. 309.
Buchwald, H et al. Long-term, continuous intravenous heparin administration by an implantable infusion pump in ambulatory patients with recurrent venous thrombosis. Surgery. Oct. 1980;88(4):507-16.

(Continued)

*Primary Examiner* — Shawquia Jackson
(74) *Attorney, Agent, or Firm* — COOLEY LLP

(57) ABSTRACT

The present invention relates to novel crystalline salt forms of mesembrine, also known as 3a-(3,4-dimethoxyphenyl)-octahydro-1-methy-6H-indol-6-one. Mesembrine has the chemical formula $C_{17}H_{23}NO_3$. The invention further relates to the preparation of a novel crystalline salt of mesembrine and to the use of the mesembrine salt as a medicament. In one embodiment the novel crystalline salt form of mesembrine is mesembrine besylate salt.

18 Claims, 27 Drawing Sheets

(56) References Cited

U.S. PATENT DOCUMENTS

| | | | |
|---|---|---|---|
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,264,970 | B1 | 7/2001 | Hata et al. |
| 6,267,981 | B1 | 7/2001 | Okamoto et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 9,381,220 | B2 | 7/2016 | Gericke et al. |
| 9,526,793 | B1 | 12/2016 | Kramer et al. |
| 11,970,446 | B2 | 4/2024 | Protzko |
| 2017/0326139 | A1 | 11/2017 | Foster |
| 2023/0312469 | A1 | 10/2023 | Protzko et al. |
| 2024/0050407 | A1 | 2/2024 | Protzko |
| 2025/0091992 | A1 | 3/2025 | Protzko et al. |
| 2025/0186397 | A1 | 6/2025 | Gray et al. |

FOREIGN PATENT DOCUMENTS

| | | | |
|---|---|---|---|
| WO | WO-2005051380 | A1 | 6/2005 |
| WO | WO-2005051381 | A1 | 6/2005 |
| WO | WO-2007000764 | A2 | 1/2007 |
| WO | WO-2010106495 | A1 | 9/2010 |
| WO | WO-2014155351 | A1 | 10/2014 |
| WO | WO-2015130995 | A1 | 9/2015 |
| WO | WO-2017201071 | A1 | 11/2017 |
| WO | WO-2019021196 | A1 | 1/2019 |
| WO | WO-2022140417 | A1 | 6/2022 |
| WO | WO-2023004428 | A1 | 1/2023 |
| WO | WO-2023166304 | A1 | 9/2023 |
| WO | WO-2023187421 | A1 | 10/2023 |
| WO | WO-2024074831 | A1 | 4/2024 |

OTHER PUBLICATIONS

Clement et al., "Physiology and pharmacology of ejaculation". Basic & Clinical Pharmacology & Toxicology. Oct. 2016; 119: 18-25.

Clement et al., "Role of Peripheral Innervation in P-Chloroamphetamine—Induced Ejaculation in Anesthetized Rats". Journal of andrology. May 6, 2006; 27(3): 381-9.

De Amicis et al., "Clinical follow-up of couples treated for sexual dysfunction". Archives of sexual behavior. Dec. 1985;14: 467-89.

FDA "Guidance for Industry: Estimating the Maximum Safe Starting Dose in Initial Clinical Trials for Therapeutics in Adult Healthy Volunteers" (Jul. 2005), 3 pages.

Gericke "Evaluating the antidepressant-like properties of Sceletium tortuosum, alone and as adjunctive treatment" (Doctoral dissertation, North-West University (South-Africa)), May 2019; 226 pages.

Gericke N et al: "Sceletium—A review update", Journal of Ethnopharmacology, Elsevier Ireland Ltd, IE, vol. 119, No. 3, Oct. 28, 2008 (Oct. 28, 2008), pp. 653-663.

Goodson, "Dental Applications," Medical Applications of Controlled Release, vol. 2, Chapter 6, 1984, pp. 115-138.

Harvey et al., "Pharmacological actions of the South African medicinal and functional food plant Sceletium tortuosum and its principal alkaloids". Journal of Ethnopharmacology. Oct. 11, 2011; 137(3): 1124-9.

Humphries et al., "Mechanisms of PCA-induced hypothermia, ejaculation, salivation and irritability in rats". Pharmacology Biochemistry and Behavior. Aug. 1, 1981; 15(2): 197-200.

International Preliminary Report on Patentability for International Application No. PCT/US2021/064653 dated Jun. 29, 2023, 8 pages.

International Preliminary Report on Patentability for International Application No. PCT/US2022/074072 dated Feb. 1, 2024, 14 pages.

International Search Report and Written Opinionfor International Application No. PCT/US2021/064653, mailed Apr. 13, 2022, 16 pages.

International Search Report and Written Opinion for International Application No. PCT/US2022/074072 dated Dec. 19, 2022, 22 pages.

International Search Report and Written Opinion for PCT/GB2023/050494 mailed May 19, 2023, 12 pages.

International Search Report and Written Opinion for PCT/GB2023/050874 mailed Jul. 3, 2023, 13 pages.

Jeffs et al., "Sceletium alkaloids. Structures of five new bases from Sceletium namaquense". The Journal of Organic Chemistry. Sep. 1982; 47(19): 3611-7.

Jeffs et al., "Late stages in the biosynthesis of mesembrine: sceletenone as a precursor to the cis-3a-(3, 4-dimethoxyphenyl) octahydroindole alkaloids". Journal of the Chemical Society, Chemical Communications. 1977(2): 60-1.

Jeffs et al., "Structure of the mesembranols and the absolute configuration of mesembrine and related alkaloids". Journal of the American Chemical Society. Jul. 1969; 91(14): 3831-9.

Kochhar et al., "A short synthesis of (+)-mesembrine". Tetrahedron letters. Jan. 1, 1983; 24(44): 4785-8.

Krstenansky., "Mesembrine alkaloids: Review of their occurrence, chemistry, and pharmacology" Journal of Ethnopharmacology, 195 (2017) p. 10-19.

Langer, "New methods of drug delivery," Science (1990); 249: 1527-1533.

Maphanga et al., "*Mesembryanthemum tortuosum* L. alkaloids modify anxiety-like behaviour in a zebrafish model". Journal of Ethnopharmacology. May 23, 2022; 290: pp. 1-13.

Meyer et al., "GC-MS, LC-MS(n), LC-high resolution-MS(n), and NMR studies on the metabolism and toxicological detection of mesembrine and mesembrenone, the main alkaloids of the legal high "Kanna" isolated from Sceletium tortuosum," Analytical and Bioanalytical Chemistry, Jan. 2015, vol. 407 (3), pp. 761-778.

Murbach et al., "A toxicological safety assessment of a standardized extract of Sceletium tortuosum (Zembrin®) in rats". Food and Chemical Toxicology. Dec. 1, 2014;74:190-9.

Renyi et al., "Ejaculations induced by p-chloroamphetamine in the rat". Neuropharmacology. Aug. 1, 1985; 24(8): 697-704.

Roscher et al., "Forensic analysis of mesembrine alkaloids in S celetium tortuosum by nonaqueous capillary electrophoresis mass spectrometry". Electrophoresis. Jun. 2012; 33(11): 1567-70.

Saudek et al., "A preliminary trial of the programmable implantable medication system for insulin delivery". New England Journal of Medicine. Aug. 31, 1989; 321(9): 574-9.

Seftel et al., "Premature Ejaculation", Diagnosis and Management of Male Sexual Dysfunction, Edited by J. J. Mulcahy, New York, N.Y., Igaku-Shoin, (1997) Chapter 11, pp. 196-203.

Sefton "Implantable pumps". Crit Rev Biomed Eng. 1987; 14(3): 201-40.

Sharlip "Diagnosis and treatment of premature ejaculation: the physician's perspective". The Journal of Sexual Medicine. May 2005; 2: 103-9.

Smith "The effects of Sceletium tortuosum in an in vivo model of psychological stress". Journal of Ethnopharmacology. Jan. 7, 2011; 133(1): 31-6.

Taber et al., "Opening of Aryl-Substituted Epoxides To Form Quaternary Stereogenic Centers: Synthesis of (-)-Mesembrine". The Journal of organic chemistry. Sep. 16, 2005; 70(19): 7711-4.

Wang et al., "A Concise Total Synthesis of (-)-Mesembrine". The Journal of Organic Chemistry. Nov. 4, 2016; 81(21): 10165-71.

(56) References Cited

OTHER PUBLICATIONS

Wu et al., "Application of temperature cycling for crystal quality control during crystallization". CrystEngComm. 2016;18(13):2222-38.
Aggarwal et al., "The role of selective serotonin reuptake inhibitors in premature ejaculation". EMJ. 2017;2(3):78-81.
Arafa et al., "A randomized study examining the effect of 3 SSRI on premature ejaculation using a validated questionnaire". Therapeutics and Clinical Risk Management. Aug. 30, 2007;3(4):527-31.
Giuliano et al., "Serotonin and premature ejaculation: from physiology to patient management". European urology. Sep. 1, 2006;50(3):454-66.
PCT Application No. PCT/GB2023/050494, International Preliminary Report on Patentability mailed Aug. 30, 2024, Applicant Kanna Health Ltd.; 7 pages.
PCT Application No. PCT/GB2023/052585, International Preliminary Report on Patentability mailed Mar. 1, 2025, Applicant Kanna Health Limited; 7 pages.
PCT Application No. PCT/GB2023/052585, International Search Report and Written Opinion, mailed Feb. 2, 2024, Applicant Kanna Health Limited; 11 pages.
Keely et al., "The 3-arylpyrrolidine alkaloid synthon. A new synthesis of dl-mesembrine". Journal of the American Chemical Society. Sep. 1968;90(20):5584-7.
Makolo et al., "Mesembrine: The archetypal psycho-active Sceletium alkaloid". Phytochemistry. Oct. 1, 2019;166: 8 pages.
Marvän et al., "Women's beliefs about the prevalence of premenstrual syndrome and biases in recall of premenstrual changes". Health Psychology. Jul. 2001; 20(4): 6 pages.
Olatunji et al., "Sceletium tortuosum: A review on its phytochemistry, pharmacokinetics, biological, pre-clinical and clinical activities". Journal of Ethnopharmacology. Apr. 6, 2022; 287: 16 pages.
Paul et al., "The Enantioselective Birch Cope Sequence for the Synthesis of Carbocyclic Quaternary Stereocenters". Application to the Synthesis of (+)-Mesembrine. Organic Letters. Aug. 31, 2006;8(18):4007-10.
Shikanga et al., "The chemotypic variation of Sceletium tortuosum alkaloids and commercial product formulations". Biochemical systematics and ecology. Oct. 1, 2012;44: 364-73.
Stevens et al., "The total synthesis of (±)-15, 16-dimethoxyerythrinan-3-one. A further application of the methyl vinyl ketone annelation of endocyclic enamines". Chemical Communications (London). 1968(18):1104-5.
Stevens et al., "Thermal rearrangement of cyclopropylimines. IV. Total synthesis of dl-mesembrine". Journal of the American Chemical Society. Sep. 1968;90(20):5580-3.
Stevens "General methods of alkaloid synthesis". Accounts of Chemical Research. Jun. 1, 1977;10(6):193-8.
Wang et al., "Palladium-catalyzed asymmetric direct intermolecular allylation of -aryl cyclic vinylogous esters: divergent synthesis of (+)-Oxomaritidine and ()-Mesembrine". Organic Letters. Jan. 27, 2021;23(3):920-4.
Yamada et al., "Total synthesis of (+)-mesembrine by asymmetric synthesis with amino acid". Tetrahedron Letters. Jan. 1, 1971;12(16):1133-6.

TG/DSC analysis of solids of hydrochloride salt Pattern 1

LNB29921-20-02-SDT-16122021

Weight Loss: 0.078 mg
Weight Percent Loss: 2.052 %

Enthalpy (normalized): 119.87 J/g
Peak temperature: 207.77 °C
Onset temperature: 194.07 °C Weight (%)

Heat Flow (Normalized) A (W/g)

Temperature T (°C)

Exo Up

TG/DSC analysis of solids of besylate salt Pattern 1

LNB29921-24-02-SDT-21122021

Weight Loss: 0.049 mg
Weight Percent Loss: 1.113 %

Enthalpy (normalized): 28.287 J/g
Peak temperature: 149.83 °C
Onset temperature: 138.31 °C Polarized light microscopy of hydrochloride salt Pattern 1(A), besylate salt Pattern 1(B) and fumarate salt Pattern 1 and 4 (C)

A:

B:

C:

XRPD of solids from besylate salt Pattern 1 (A) and magnified dried solids (B)

Mean total concentrations of mesembrine besylate salt following IP administration to male C57Bl/6J mouse at 10.0 mg/Kg

CRYSTALLINE SALT FORMS OF MESEMBRINE

The present application is a continuation of U.S. patent application Ser. No. 18/129,725, filed Mar. 31, 2023, which is related to, and claims the benefit of GB2204778.1, filed on 1 Apr. 2022 (01.04.2022), the contents of which are hereby incorporated by reference in their entirety.

FIELD OF THE INVENTION

The present invention relates to novel crystalline salt forms of mesembrine, also known as 3a-(3,4-dimethoxyphenyl)-octahydro-1-methy-6H-indol-6-one. Mesembrine has the chemical formula $C_{17}H_{23}NO_3$.

The invention further relates to the preparation of a novel crystalline salt of mesembrine and to the use of the mesembrine salt as a medicament. In one embodiment the novel crystalline salt form of mesembrine is mesembrine besylate salt.

BACKGROUND TO THE INVENTION

Mesembrine is an alkaloid which naturally occurs in the *Sceletium tortuosum* species of plants indigenous to South Africa. The genus *Sceletium*, classified under the Aizoaceae family, is indigenous to the Western, Eastern and Northern Cape province of South Africa. In addition to mesembrine other alkaloids are found in extracts of *Sceletium tortuosum* including mesembrenol, $\Delta^7$mesembrenone, mesembranol, mesembrenone, and epimesembranol.

Extracts of *S. tortuosum* have a long history of use in traditional medicine by the San and Khoikhoi people in South Africa where it was used as a masticatory and a medicine to quench their thirst, fight fatigue and for healing, social, and spiritual purposes.

More recently studies have revealed that extracts of the plant have numerous biological properties and extracts of *S. tortuosum* may be useful in the treatment of anxiety and depression, psychological and psychiatric disorders, improving mood, promoting relaxation and happiness.

An in vivo study in rats demonstrated a positive effect of an extract of *S. tortuosum* on restraint-induced anxiety (Smith, 2011), and a small series of case reports described preliminary evidence for antidepressant and anxiolytic activity in patients suffering from major depression who were treated with tablets comprising a standardized extract of milled *S. tortuosum* raw material (Gericke, 2001). A dietary supplement comprising such material is available as Zembrin®.

The mechanisms of action on the central nervous system (CNS) of Zembrin® were identified as the ability to cause blockade of the serotonin (5-HT) transporter and enable selective inhibition of the phosphodiesterase-4 (PDE4) enzyme (Harvey et al, 2011).

The various alkaloids which occur in *S. tortuosum* have also been studied in particular the three main alkaloids, mesembrenol, mesembrenone, and mesembrine. All three have been shown to be potently active in a 5-HT transporter binding assay and against PDE4B activity, (Harvey et al., 2011).

Mesembrenone was described as having a dual activity on 5-HT uptake and PDE4 inhibition as the difference $IC_{50}$ concentrations on the two assays was x17, whereas it was x258 for mesembrenol and x5500 mesembrine. However, mesembrine had a greater selectivity for the 5-HT transporter over PDE4B.

The structure of mesembrine was described by Popelak et al., 1960 and the configuration by P. W. Jeffs et al., 1969. Mesembrine occurs naturally as the (−)-isomer as (−)-mesembrine.

Mesembrine can be isolated from extracts of *S. tortuosum* or can be synthesized chemically using the method described by Wang et al., 2016.

Mesembrine has a solubility of 10 mg/ml in chloroform and ethanol but has a low solubility in water meaning that it's use as in the preparation of a pharmaceutical is limited as such formation of a saline form of the compound is desirable.

In 1957 the mesembrine base was successfully crystallized to its hydrochloride salt (Bodendorf and Krieger, 1957), however the HCl salt of mesembrine is poorly soluble at higher concentrations meaning only small doses of mesembrine can be prepared using the HCl salt.

An object of the present invention is the preparation of a salt form of mesembrine with superior properties to those presently available.

It has now been found that the monobenzenesulfonate (also referred to as besylate) salified form of mesembrine exhibits advantageous properties which render it particularly suitable for use as active principle in a medicament.

Specifically, the applicant has demonstrated, that the besylate form of mesembrine unexpectedly has superior properties in comparison to other salt forms. In particular the mesembrine besylate salt of the invention has improved solubility and stability, which are further improved with respect to the hydrochloride or fumarate form of this same compound.

The advantages related to the besylate salt form of mesembrine in comparison to the free base form or to other saline forms, such as the hydrochloride and the fumarate, are described with reference to physicochemical analysis and characterization.

BRIEF SUMMARY OF THE DISCLOSURE

In accordance with a first aspect of the present invention there is provided a mesembrine salt, wherein the salt is taken from the group consisting of mesembrine besylate; mesembrine phosphate; mesembrine tartrate; mesembrine fumarate and mesembrine succinate.

Preferably the mesembrine salt is a mesembrine besylate salt.

More preferably the mesembrine salt is in a solid form. More preferably the salt is in a crystalline form.

When the mesembrine salt of the invention in mesembrine besylate the salt is preferably characterized by an XRPD pattern according to FIG. 18 comprising peaks at about the positions as described in Table 3.10. Such a salt is defined as mesembrine besylate salt Pattern 1.

In embodiments, the crystalline form is characterized by peaks in an XPRD pattern at 11.1±0.2, 12.7±0.2, 16.6±0.2, 23.8±0.2, and 24.6±0.2°2θ. In embodiments, the crystalline form is further characterized by at least one peak selected from 9.2±0.2, 11.0±0.2, 13.5+0.2, 19.5±0.2, 20.7±0.2, and 21.2±0.2°2θ. In embodiments, the variance at any of these peaks is ±0.1°2θ. For example, in embodiments, the crystalline form is characterized by peaks in an XPRD pattern at 11.1±0.1, 12.7±0.1, 16.6±0.1, 23.8±0.1, and 24.6±0.1°2θ. In embodiments, the crystalline form is further characterized by at least one peak selected from 9.2±0.1, 11.0±0.1, 13.5±0.1, 19.5±0 0.1, 20.7±0.1, and 21.2±0.1°2θ.

In embodiments, the crystalline form is characterized by peaks in a XRPD pattern at 9.2±0.2, 11.0±0.2, 11.1±0.2, 12.3±0.2, 12.7±0.2, 13.5±0.2, 15.4±0.2, 16.6±0.2, 18.5±0.2, 19.5±0.2, 19.8±0.2, 20.2±0.2, 20.7±0.2, 21.2±0.2, 21.6±0.2, 22.4±0.2, 22.9±0.2, 23.2±0.2, 23.8±0.2, 24.1±0.2, 24.6±0.2, 25.6±0.2, 26.2±0.2, 27.9±0.2, 28.3±0.2, 28.6±0.2, 29.3±0.2, 31.1±0.2, 32.4±0.2, 33.0±0.2, and 33.9±0.2°2θ. In embodiments, the variance at any of these peaks is ±0.1°2θ.

In embodiments, the crystalline form is characterized by any one, two, three, four, five, six, seven, eight, nine, ten, eleven, or more, XRPD peaks listed in Table 1.1.

TABLE 1.1

XPRD Peaks for the Mesmebrine Besylate Salt: Pattern 1

| Peak # | Pos. [°2θ] |
|---|---|
| 1 | 9.2 |
| 2 | 11.0 |
| 3 | 11.1 |
| 4 | 12.3 |
| 5 | 12.7 |
| 6 | 13.5 |
| 7 | 15.4 |
| 8 | 16.6 |
| 9 | 18.5 |
| 10 | 19.5 |
| 11 | 19.8 |
| 12 | 20.2 |
| 13 | 20.7 |
| 14 | 21.2 |
| 15 | 21.6 |
| 16 | 22.4 |
| 17 | 22.9 |
| 18 | 23.2 |
| 19 | 23.8 |
| 20 | 24.1 |
| 21 | 24.6 |
| 22 | 25.6 |
| 23 | 26.2 |
| 24 | 27.9 |
| 25 | 28.3 |
| 26 | 28.6 |
| 27 | 29.3 |
| 28 | 31.1 |
| 29 | 32.4 |
| 30 | 33.0 |
| 31 | 33.9 |

When the mesembrine salt of the invention in mesembrine besylate the salt is alternatively characterized by an XRPD pattern according to FIG. 20 comprising peaks at about the positions as described in Table 3.13. Such a salt is defined as mesembrine besylate salt Pattern 2.

In embodiments, the crystalline form is characterized by peaks in an XPRD pattern at 11.0±0.2, 13.4±0.2, 15.1±0.2, 18.6±0.2, or 23.7±0.2°2θ. In embodiments, the crystalline form is further characterized by at least one peak selected from 15.6±0.2, 16.1±0.2, 18.2±0.2, 21.3±0.2, or 25.1±0.2°2θ. In embodiments, the variance at any of these peaks is ±0.1 °2θ. For example, in embodiments, the crystalline form is characterized by peaks in an XPRD pattern at 11.0±0.1, 13.4±0.1, 15.1±0.1, 18.6±0.1, or 23.7±0.1°2θ. In embodiments, the crystalline form is further characterized by at least one peak selected from 15.6±0.1, 16.1±0.1, 18.2±0.1, 21.3±0.1, or 25.1±0.1°2θ.

In embodiments, the crystalline form is characterized by peaks in a XRPD pattern at 3.2±0.2, 7.4±0.2, 9.3±0.2, 11.0±0.2, 11.6±0.2, 12.1±0.2, 12.6±0.2, 13.4±0.2, 14.5±0.2, 15.1±0.2, 15.6±0.2, 16.1±0.2, 16.8±0.2, 17.9±0.2, 18.2±0.2, 18.6±0.2, 18.8±0.2, 19.5±0.2, 19.8±0.2, 20.7±0.2, 21.3±0.2, 21.8±0.2, 22.4±0.2, 22.6±0.2, 22.7±0.2, 23.3±0.2, 23.7±0.2, 24.1±0.2, 24.3±0.2, 24.7±0.2, 25.1±0.2, 25.7±0.2, 26.3±0.2, 26.6±0.2, 27.0±0.2, 27.5±0.2, 28.0±0.2, 28.5±0.2, 29.0±0.2, 29.3±0.2, 29.5±0.2, 30.0±0.2, 30.7±0.2, 31.7±0.2, 32.1±0.2, 32.5±0.2, 33.1±0.2, 33.5±0.2, and 34.4±0.2°2θ. In embodiments, the variance at any of these peaks is ±0.1°2θ.

In embodiments, the crystalline form is characterized by any one, two, three, four, five, six, seven, eight, nine, ten, eleven, or more, XRPD peaks listed in Table 1.2.

TABLE 1.2

XPRD Peaks for the Mesmebrine Besylate Salt: Pattern 2

| Peak # | Pos. [°2θ] |
|---|---|
| 1 | 3.2 |
| 2 | 7.4 |
| 3 | 9.3 |
| 4 | 11.0 |
| 5 | 11.6 |
| 6 | 12.1 |
| 7 | 12.6 |
| 8 | 13.4 |
| 9 | 14.5 |
| 10 | 15.1 |
| 11 | 15.6 |
| 12 | 16.1 |
| 13 | 16.8 |
| 14 | 17.9 |
| 15 | 18.2 |
| 16 | 18.6 |
| 17 | 18.8 |
| 18 | 19.5 |
| 19 | 19.8 |
| 20 | 20.7 |
| 21 | 21.3 |
| 22 | 21.8 |
| 23 | 22.4 |
| 24 | 22.6 |
| 25 | 22.7 |
| 26 | 23.3 |
| 27 | 23.7 |
| 28 | 24.1 |
| 29 | 24.3 |
| 30 | 24.7 |
| 31 | 25.1 |
| 32 | 25.7 |
| 33 | 26.3 |
| 34 | 26.6 |
| 35 | 27.0 |
| 36 | 27.5 |
| 37 | 28.0 |
| 38 | 28.5 |
| 39 | 29.0 |
| 40 | 29.3 |
| 41 | 29.5 |
| 42 | 30.0 |
| 43 | 30.7 |
| 44 | 31.7 |
| 45 | 32.1 |
| 46 | 32.5 |
| 47 | 33.1 |
| 48 | 33.5 |
| 49 | 34.4 |

In accordance with a second aspect of the present invention there is provided a process for the preparation of a mesembrine salt comprising the steps of:

a) Dissolving mesembrine in a solvent
b) Addition of the appropriate counterion to the mesembrine solution under temperature cycling conditions; and
c) Isolation of solids comprising the mesembrine salt.

In one embodiment the counterion of step b) is a weak acid with a pKa of greater than 0.5. Preferably the counterion of step b) is benzenesulfonic acid.

In accordance with a third aspect of the present invention there is provided a pharmaceutical preparation comprising a mesembrine salt, wherein the salt is taken from the group consisting of mesembrine besylate; mesembrine phosphate; mesembrine tartrate; mesembrine fumarate and mesembrine succinate.

Preferably the salt is mesembrine besylate.

In accordance with a fourth aspect of the present invention there is provided a mesembrine salt for use in the treatment of a disease, wherein the salt is taken from the group consisting of mesembrine besylate; mesembrine phosphate; mesembrine tartrate; mesembrine fumarate and mesembrine succinate.

Preferably the mesembrine salt is mesembrine besylate.

The mesembrine salt of the invention may be used in the treatment of impulse control in a human or animal subject. In particular the treatment may be related to the field of sexual dysfunction such as delaying ejaculation, delaying orgasm and/or preventing premature ejaculation during sexual activity in human males. In addition the mesembrine salt of the invention may be used to delay ejaculatory latency in a male human.

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration.

In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration, nasal inhalation, and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some embodiments, a therapeutically effective dosage should produce a serum concentration of active ingredient of from about 0.001 ng/ml to about 1.0 ng/ml, 2-10 ng/ml, 11 to 50 ng/ml, 51-200 ng/ml, or about 200 to 1000 ng/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, or about 1000 mg, and in some embodiments from about 10 mg to about 500 mg of the active ingredient or a combination of essential ingredients per dosage unit form.

The active ingredient may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e., dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the U.S. Pharmacopeia (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms including active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water-soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit° series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds, which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE 28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles, and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, CRC Crit. Ref. Biomed. Eng. 14:201 (1987); Buchwald et al., Surgery 88:507 (1980); Saudek et al., N Engl. J. Med. 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, Medical Applications of Controlled Release, vol. 2, pp. 115-138 (1984)). In some embodiments, a controlled release device is introduced into a subject in proximity of the site of inappropriate immune activation or a tumor. Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and non-flammable HFA propellants are selected from HFA 134a (1,1,1,2-tetrafluoroethane) and HFA227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

In human therapeutics, the physician will determine the dosage regimen that is most appropriate according to a preventive or curative treatment and according to the age, weight, stage of the disease and other factors specific to the subject to be treated. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, or about 1000 mg, and in some embodiments from about 10 mg to about 500 mg of the active ingredient or a combination of essential ingredients per dosage unit form.

The amount of active ingredient in the formulations provided herein, which will be effective in the prevention or treatment of a disorder or one or more symptoms thereof, will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject.

Exemplary doses of a formulation include milligram or microgram amounts of the active compound per kilogram of subject (e.g., from about 1 microgram per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above-described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

BRIEF DESCRIPTION OF THE DRAWINGS

Embodiments of the invention are further described hereinafter with reference to the accompanying drawings, in which.

DEFINITIONS

Figure 1:
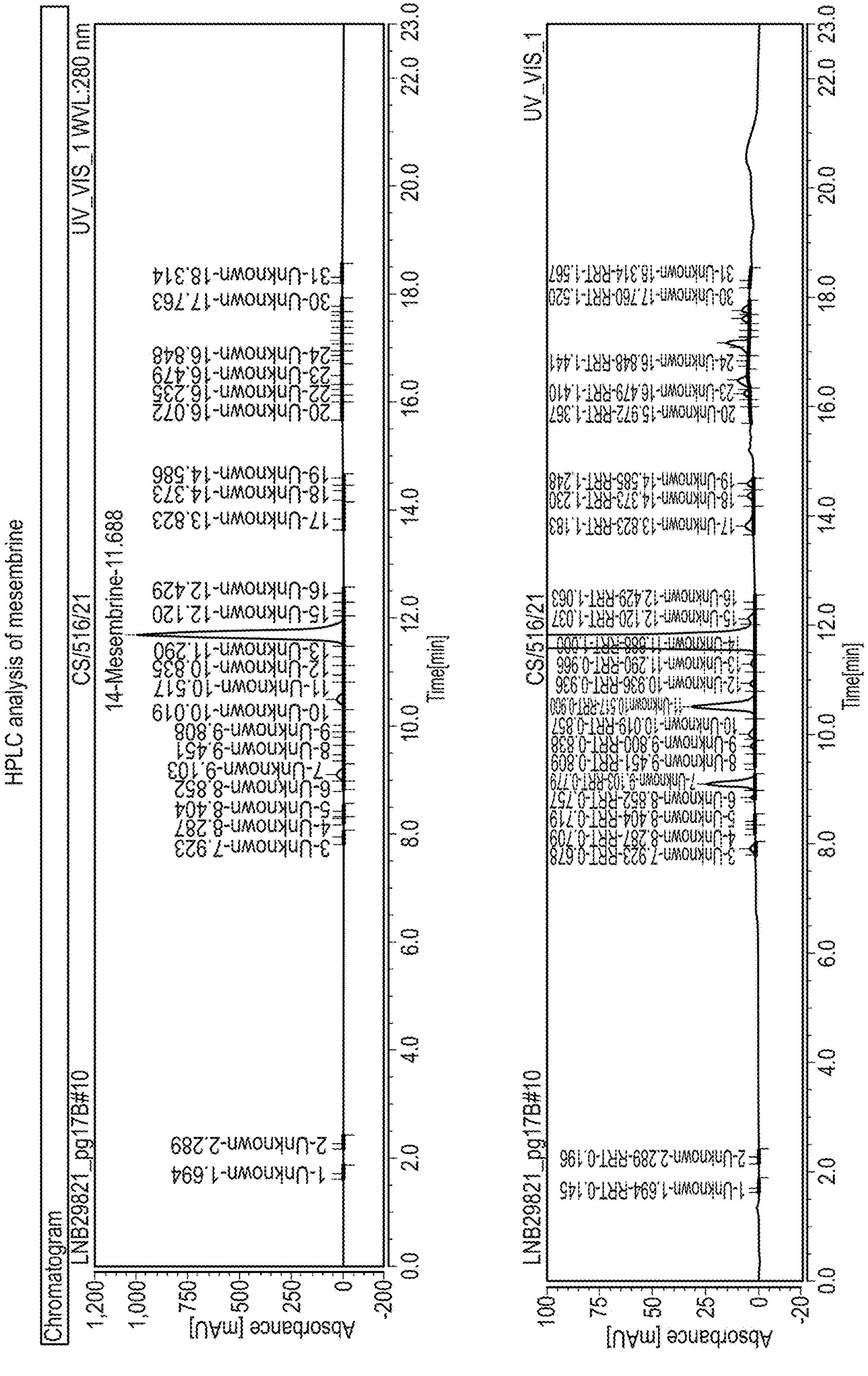
FIG. 1 shows an HPLC analysis of mesembrine.

Various definitions are made throughout this document. Most words have the meaning that would be attributed to those words by one skilled in the art. Words specifically defined either below or elsewhere in this document have the meaning provided in the context of the present invention as a whole and as typically understood by those skilled in the art.

The term "substantially crystalline" means at least about 50% crystalline and ranging up to about 100% crystalline. The present invention provides a salt that is at least about 50% crystalline, at least about 60% crystalline, at least about 70% crystalline, at least about 80% crystalline, at least about 90% crystalline, at least about 95% crystalline, at least about 98% crystalline, or at least about 100% crystalline in form.

The degree or percentage of crystallinity may be determined by the skilled person using X-ray powder diffraction (XRPD). Other techniques, such as solid-state nuclear magnetic resonance (NMR), FT-IR, Raman spectroscopy, differential scanning calorimetry (DSC) and microcalorimetry, may also be used.

Crystalline forms of the salt of the invention may be in the form of a solvate, including but not limited to a hydrate (e.g., a monohydrate), or otherwise (e.g., in the form of an anhydrate).

"Subject," "individual" or "patient" is used interchangeably herein and refers to a vertebrate, preferably a mammal. Mammals include, but are not limited to, murines, rodents, simians, humans, farm animals, sport animals and pets.

"Treating" or "treatment" of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. Treatment can also refer to the lessening of the severity and/or the duration of one or more symptoms of a disease or disorder. In a further feature, the treatment rendered has lower potential for long term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, adsorption, distribution, metabolism and excretion etc., of the patient to be treated.

"Vehicle" refers to a diluent, excipient or carrier with which a compound is administered to a subject. In some embodiments, the vehicle is pharmaceutically acceptable.

"Active ingredient" or "Active pharmaceutical ingredient" or "API" refers to the novel mesembrine salt of the invention.

Mesembrine is a chiral alkaloid with the CAS name: (3aS-cis)-3a-(3,4-Dimethoxyphenyl)octahydro-1-methyl-6H-indol-6-one. It occurs naturally at the cis-isomer but may also be synthesized as the trans-isomer or as a racemate. The structures below denote the structural configuration of mesembrine. The mesembrine of the present invention may occur as the cis-isomer, the trans-isomer or a racemate of the two.

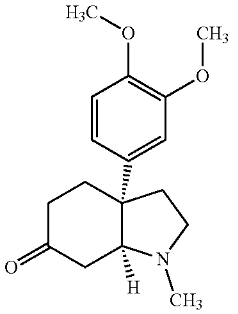

Cis-mesembrine

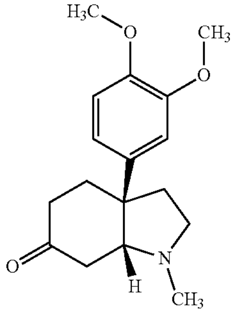

Trans-mesembrine

DETAILED DESCRIPTION OF THE INVENTION

The Examples below describe the phases of development of a highly soluble and characterized mesembrine salt of the present invention. The applicant has determined that mesembrine is poorly soluble in aqueous systems and as such means that the use of the compound as an active pharmaceutical ingredient in medicinal presentations is limited by its lack of solubility. A novel salt form has been produced which is both soluble and stable and as such is able to be used in the preparation of medicines and supplements.

Mesembrine can be isolated from extracts of *S. tortuosum* or can be synthesized chemically using the method described by Wang et al., 2016.

Example 1: Characterisation of Mesembrine

Materials and Methods

The mesembrine used in the following series of experiments was isolated from an extract of *Sceletium tortuosum*, the compound was characterized by several different methods in order to determine the purity of the starting material and to benchmark it against the subsequent salts that were to be formed.

HPLC analysis was carried out to determine the chemical purity of the mesembrine and to provide information on any impurities. The following conditions were use:

Column: Waters Acquity BEH 018 1.7 μm 150 mm×2.1 mm

Column Temperature: 33° C.

Autosampler Temperature: 25° C.

UV Wavelength: 280 nm

Injection Volume: 5 μL

Flow Rate: 0.29 mL/min

Mobile Phase A: 0.1% NH4 in H2O

Mobile Phase B: Methanol:Water 20:80% v/v

Gradient Program:

| Time (minutes) | Mobile Phase A [%] | Mobile Phase B [%] |
|---|---|---|
| 0.00 | 80 | 20 |
| 2.0 | 80 | 20 |
| 4.0 | 60 | 40 |
| 6.0 | 50 | 50 |
| 9.0 | 50 | 50 |
| 14.0 | 10 | 90 |
| 17.0 | 10 | 90 |

-continued

| Time (minutes) | Mobile Phase A [%] | Mobile Phase B [%] |
|---|---|---|
| 17.1 | 80 | 20 |
| 23.0 | 80 | 20 |

$^1H$ and $^1H/^{13}C$ NMR analysis were carried out in order to determine the chemical structure of the mesembrine used. NMR experiments were performed on a Bruker AVIIIHD spectrometer equipped with a DCH cryoprobe operating at 500.12 MHz for protons. Experiments were performed in deuterated DMSO, and each sample was prepared to ca. 10 mM concentration.

The infrared (IR) spectrum was additionally recorded in order to obtain a benchmark of the starting mesembrine material. The following conditions were used Infrared spectroscopy was carried out on a Bruker ALPHA P spectrometer. Sufficient material was placed onto the centre of the plate of the spectrometer and the spectra were obtained using the following parameters:

Resolution: 4 cm−1

Background Scan Time: 16 scans

Sample Scan Time: 16 scans

Data Collection: 4000 to 400 cm−1

Result Spectrum: Transmittance

Software: OPUS version 6

A Karl Fischer (KF) analysis was finally undertaken in order to determine the water content of the mesembrine sample used. The following conditions were used Solids were analysed either using a vaporizer method, or using an external dissolution method:

Vaporizer method: Approximately 10 mg of material was weighted into a 10 mL glass vial and tightly sealed with a screw cap. The water content of the samples was analysed using an InMotion KFoven Autosampler, at 150° C. The samples were run in duplicate, and an average moisture content reported.

| | | |
|---|---|---|
| Blank | Oven Temperature | 150° C. |
| | Source for Drift | Determination |
| | Max. Start Drift | 10 μg/min |
| | Carrier Gas Flow Rate | 80 mL/min |
| | Transfer Tube Heating | No |
| | Mix Time | 60 s |
| | Stir Speed | 45% |
| | Drift Termination | 10 s (Delay Time) |
| | Max. Titration Time | 600 s |
| Sample | Oven Temperature | 150° C. |
| | Source for Drift | Determination |
| | Max. start Drift | 10 μg/min |
| | Carrier Gas Flow Rate | 80 mL/min |
| | Mix Time | 60 s |
| | Stir Speed | 45% |
| | Drift Termination | 10 s (Delay Time) |
| | Max. Titration Time | 600 s |

External Dissolution method: A known mass of the sample to be analysed was dissolved in a known mass of methanol. Prior to analysis being carried out, solvent blank measurements were carried out. Approximately 1 mL of methanol was injected into the titration cell of a Mettler Toledo C30 compact titrator, and the syringe back-weighed to determine the weight of methanol added.

For the sample analysis, approximately 1 mL of the solution was injected into the titration cell, and the syringe back-weighed and the weight of the added solution entered onto the instrument. Titration was initiated once complete dissolution was observed, and the water content was automatically calculated by the instrument. The measurement was carried out in duplicate and an average water content reported.

Results

FIG. 1 shows the HPLC analysis of the mesembrine starting material and the impurity peaks found within the sample. It was determined that the purity of the mesembrine was 91.17% are by HPLC, with 8.83% area by HPLC impurities.

Figure 2:
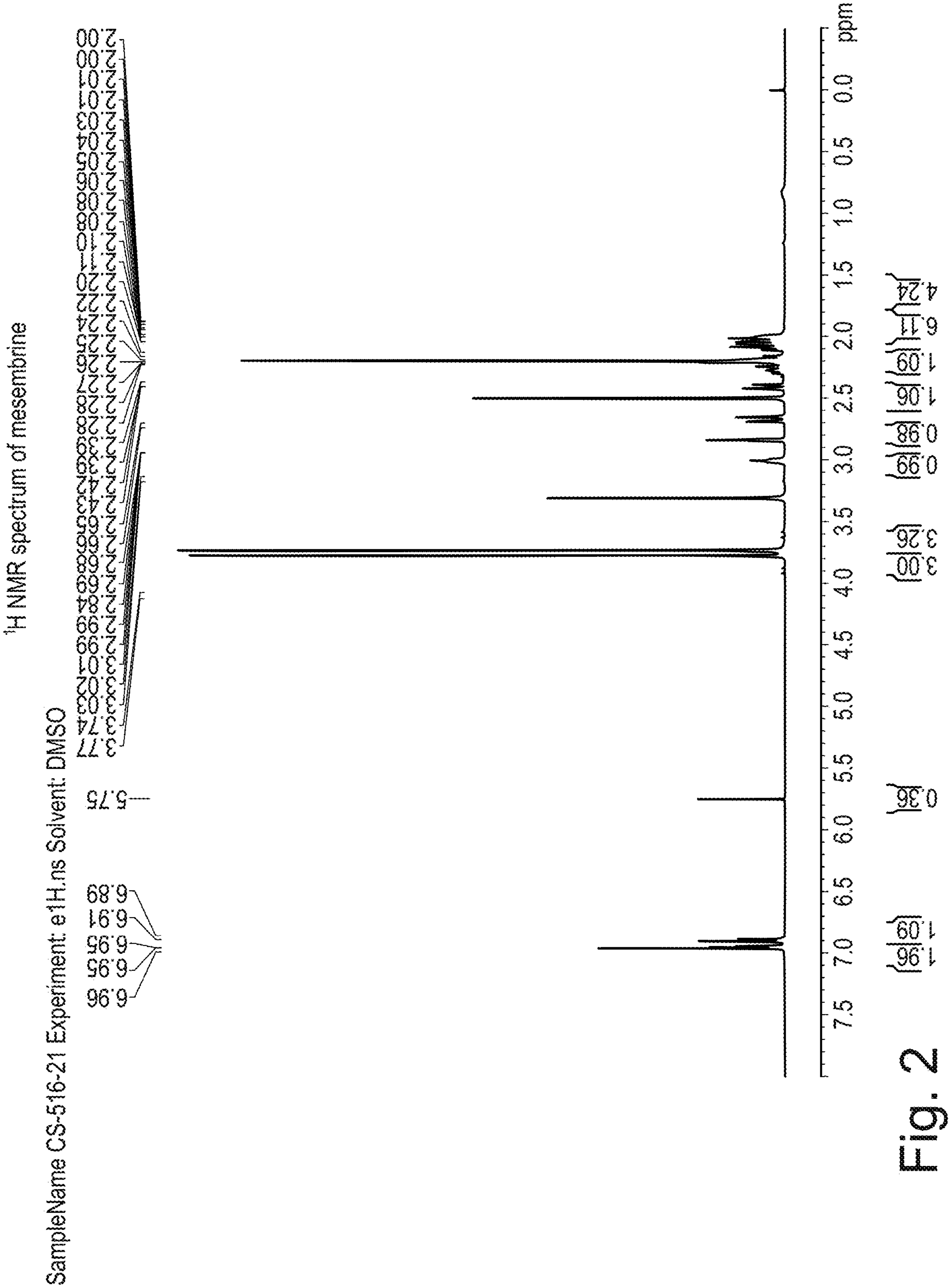
FIG. 2 shows a $^1$H NMR spectrum of mesembrine.

FIG. 2 details the $^1H$ NMR spectrum, it was determined that the spectrum was consistent with the chemical structure of mesembrine. There was a residual content of 5.0 wt % DCM which is equal to 0.2 equivalents of DCM. No residual methanol was observed.

Figure 3:
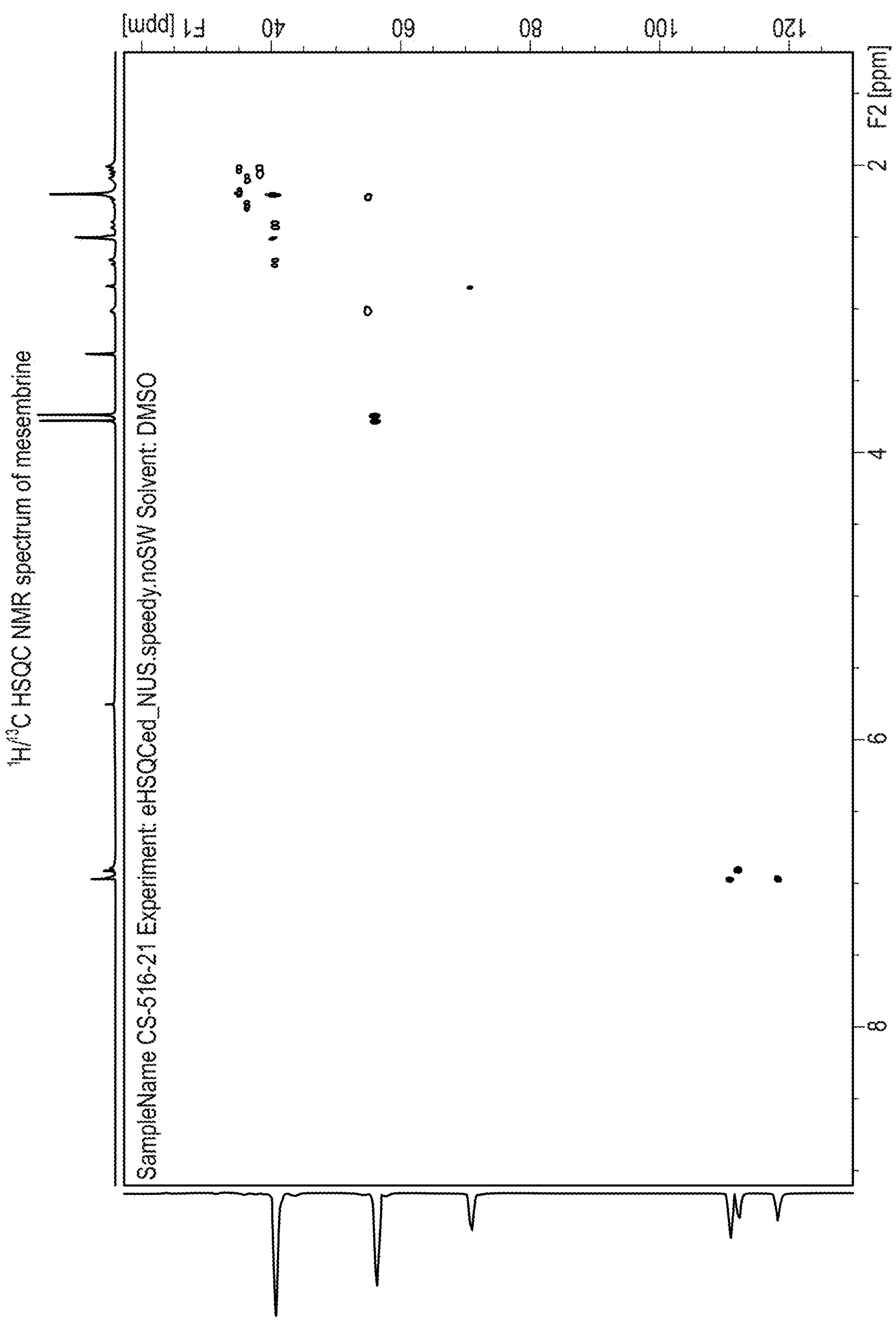
FIG. 3 shows a $^1$H/$^{13}$C HSQC NMR spectrum of mesembrine.

FIG. 3 details the $^1H/^{13}C$ HSQC NMR spectrum. Analysis showed that the sample was consistent with mesembrine.

Figure 4:
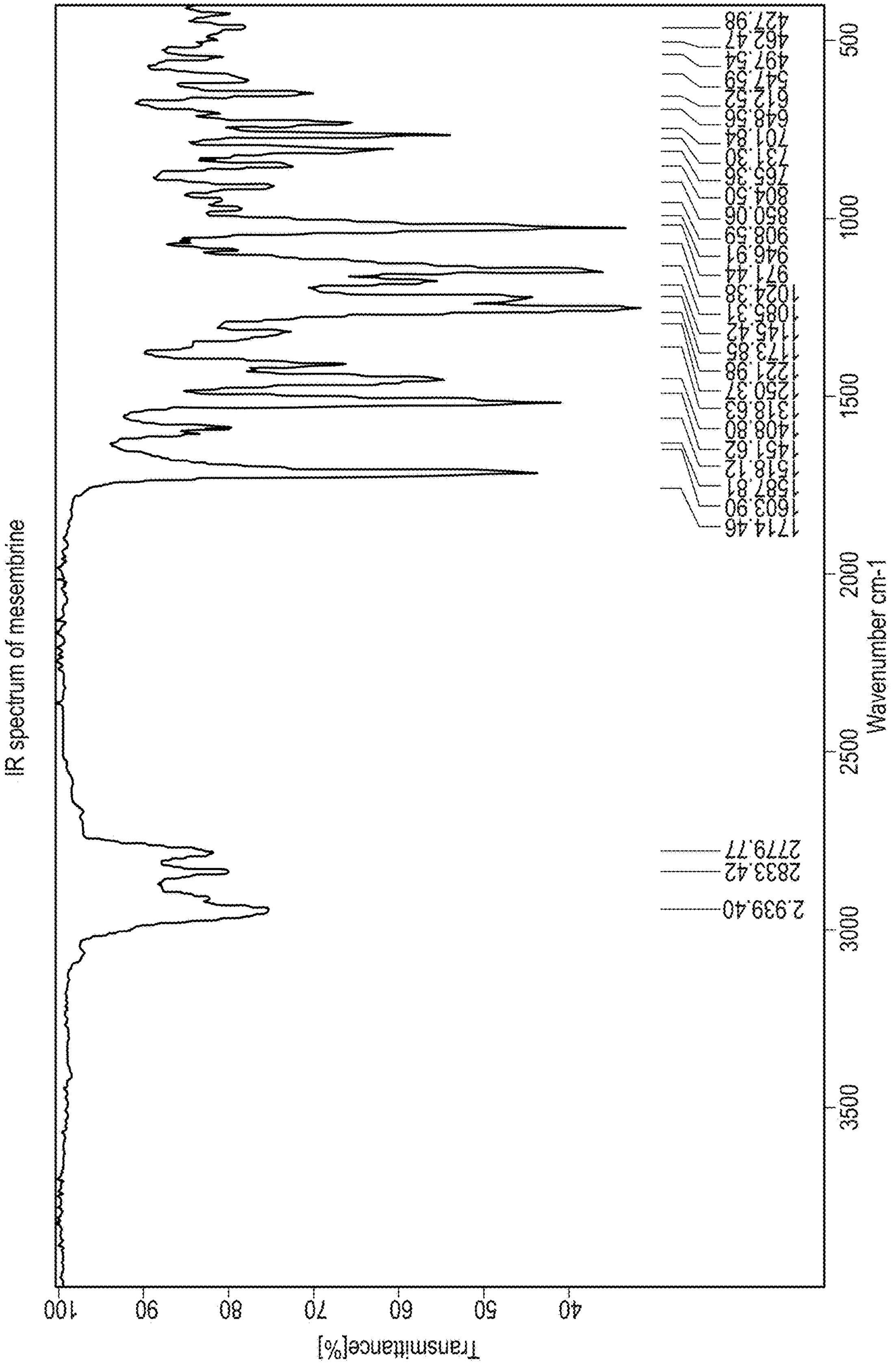
FIG. 4 shows an IR spectrum of mesembrine.

FIG. 4 details the IR spectrum of the mesembrine used and KF analysis determined that the water content of the received material was 1.1% (w/w).

Conclusion

The characterization of mesembrine determined that the sample used for salt formation assessment was of an acceptable purity, matched the expected chemical structure for mesembrine and comprised an acceptable level of water.

The mesembrine sample was therefore suitable for use in additional experiments to assess the ability of salt formation.

Example 2: Solubility of Mesembrine

Materials and Methods

Approximately 360 mg of mesembrine was weighed out and dissolved in 5 mL of dichloromethane (DCM). After dissolution 278 μL of the solution was aliquoted into pre-tared vials, and the solvent allowed to evaporate at ambient conditions for 1 h. The vials were then dried at 20° C. under vacuum for ca. 22 h. After drying, the vials were back-weighed to determine the mass of mesembrine in each vial.

The miscibility study was carried out by adding aliquots of the desired solvent system to each vial. The following aliquot sizes were used: Aliquot numbers 1-10-20 μL; 11-16-50 μL; 17-19-200 μL; 20-750 μL.

In between additions the experiment was heated to 40° C. for ca. 5 minutes to facilitate miscibility/solubility. Additions were continued until miscibility was observed, or ca. 100 volumes (2 mL) had been added.

Results

Table 2.1 below details the approximate solvent miscibility/solubility of mesembrine in the 18 different solvents tested.

TABLE 2.1

Solubility of mesembrine in various solvents

| # | Solvent/% v/v | Miscibility/mg/mL |
|---|---|---|
| 1 | 2-Methyl THF | >845 |
| 2 | 1,4-Dioxane | >850 |
| 3 | 2-Propanol (IPA) | >870 |
| 4 | Acetone | >890 |
| 5 | Acetonitrile | >855 |
| 6 | 2-Propanol:Water (50:50) | >870 |
| 7 | DMSO | >288 |
| 8 | Ethanol | >630 |
| 9 | Ethyl acetate | >445 |
| 10 | Heptane | <9 |
| 11 | Isopropyl acetate | >900 |
| 12 | Methanol | >455 |
| 13 | Methyl ethyl ketone (MEK) | >915 |
| 14 | N-Methyl-2-pyrrolidone (NMP) | >450 |
| 15 | Tert-butyl methyl ether | >465 |
| 16 | Tetrahydrofuran (THF) | >381 |
| 17 | Toluene | >455 |
| 18 | Water | <9 |

As can be seen in Table 2.1 mesembrine was very poorly soluble in heptane and water and had a reasonable solubility in ethanol and other organic solvents.

Conclusion

Many organic solvents are classed as toxic or carcinogenic and as such are not suitable for use as diluents in pharmaceutical compositions.

The low solubility of mesembrine in water means that the compound will be difficult to formulate into a pharmaceutical composition as only a small mass of the compound can be dissolved in water.

In a study determining the toxicity of Zembrin®, an extract of *Sceletium tortusosum*, which comprises ca.20% mesembrine, the no observed adverse effect level (NOAEL) was determined to be 420 mg extrapolated to a 70 kg human (Murbach et al., 2014).

Therefore, a dose of around 84 mg of mesembrine (20% of 420 mg) would require approximately 10 ml of water to form a miscible solution, this amount being far higher than the standard 00 capsule size used for medication delivery which has a fill volume of 0.9 ml.

Example 3: Primary Salt Formation Assessment

Materials and Methods

The primary salt formation was assessed using reactions with 12 counterions across six solvent systems. The various counterions were selected based on their pKa, and also as a result of their molecular weight, toxicity and diversity. The counterions and solvents used for the primary salt formation assessment are as detailed in Table 3.1 below.

TABLE 3.1

| Counterions and solvent details | | | | | | |
|---|---|---|---|---|---|---|
| # | Counterions | MW/g/mol | pKa | Merck Class | Solvent System/% v/v | Upper Temp. Limit/° C. |
| 1 | Hydrochloric acid | 36.46 | −6 | 1 | THF | 40 |
| 2 | Sulfuric acid | 98.08 | −3 | 1 | Ethyl acetate | |
| 3 | p-Toluenesulfonic acid | 172.2 | −1.34 | 2 | Ethanol | |
| 4 | Methanesulfonic acid | 96.10 | −1.2 | 2 | IPA:Water 50:50 | |
| 5 | Benzenesulfonic acid | 158.18 | 0.7 | 2 | MEK | |
| 6 | Maleic acid | 116.08 | 1.92; 6.23 | 1 | Acetonitrile | |
| 7 | Phosphoric acid | 98.00 | 1.96; 7.12; 12.32 | 1 | | |
| 8 | (+)-L-Tartaric acid | 150.09 | 3.02; 4.36 | 1 | | |
| 9 | Fumaric acid | 116.08 | 3.03; 4.38 | 1 | | 25 |
| 10 | Citric acid | 192.13 | 3.13; 4.76; 6.40 | 1 | | |
| 11 | Succinic acid | 118.09 | 4.21; 5.64 | 1 | | |
| 12 | Benzoic acid | 179.18 | 4.3 | 3 | | |

Stock solutions of mesembrine at 200 mg/mL were prepared in the desired solvent systems. Separately, 1.1 equivalents of counterion were dispensed (either weighed, or measured using an autopipette) into 72×2 mL vials and a stirrer bar added.

100 μL of the appropriate solvent system was added to each vial to dissolve/suspend the counterion. 100 μL of the mesembrine stock solution in the correct solvent system was added to each vial, at the specified upper temperature limit.

The experiments were then temperature cycled between the upper temperature limit (specified in Table 3.1) and 5° C. at 0.1° C./min, with 1 h holds at the upper temperature limit, and 5° C. for ca. 72 h.

After temperature cycling, solids were isolated from experiments at 5° C., and analysed by XRPD. Any experiments which did not contain solids had anti-solvent addition carried out and were temperature cycled for a further ca. 24 h as above.

Solids were dried at 40° C. under vacuum for ca. 24 h, and then re-analysed by XRPD.

Solids were then stored at 40° C./75% RH for ca. 24 h, and then re-analysed by XRPD.

Potential salt forms were also analysed by TGA/DSC.

Additional experiments were carried out for selected counterions (numbers 2, 3, 4 and 6 from Table 3.1) had not yielded any solids of a potential salt of mesembrine from the initial set of salt formations. The upper temperature limit was decreased from 40° C. to 25° C. as degradation was noted in these during the initial experiments as detailed below and in Table 3.2.

A stock solution of mesembrine at 200 mg/mL was prepared in MEK. Separately, 1.1 equivalents of counterion were dispensed (either weighed, or measured using an autopipette) into 4×2 mL vials and a stirrer bar added.

100 μL of MEK was added to each vial to dissolve/suspend the counterion. 100 μL of the mesembrine stock solution was added to each vial, at 25° C.

The experiments were then temperature cycled between 25° C. and 5° C. at 0.1° C./min, with 1 h holds at 25° C. and 5° C. for ca. 72 h. After temperature cycling, anti-solvent addition carried out in 100 μL aliquots, at 5° C. until a visual change was observed or 1 mL of heptane had been added.

The experiments were temperature cycled for a further ca. 24 h as above.

TABLE 3.2

| Counterions and solvent details for additional salt formation assessment | | | | | | |
|---|---|---|---|---|---|---|
| # | Counterions | MW/ g/mol | pKa | Merck Class | Solvent System/ % v/v | Upper Temp. Limit/° C. |
| 1 | p-Toluenesulfonic acid | 172.2 | −1.34 | 2 | MEK | 25 |
| 2 | Methanesulfonic acid | 96.10 | −1.2 | 2 | | |
| 3 | Maleic acid | 116.08 | 1.92; 6.23 | 1 | | |
| 4 | Sulfuric acid | 98.08 | −3 | 1 | | |

Results

The primary salt formation assessment from reactions with 12 counterions across six different solvent systems were determined. The results of the primary salt screen are summarized in Tables 3.3 to 3.5 below.

TABLE 3.3

| Summary of damp XRPD analysis from primary formation assessment | | | | | | |
|---|---|---|---|---|---|---|
| Counterions | THF | Ethyl Acetate | Ethanol | IPA: Water 50:50% v/v | MEK | MeCN |
| Hydrochloric acid | 1, C | 1, PC | 1, C | — | 1, C | 1, C |
| Sulfuric acid | — | — | — | — | — | — |
| p-Toluenesulfonic acid | — | — | — | — | — | — |
| Methanesulfonic acid | — | — | — | — | — | — |
| Benzenesulfonic acid | 1, C | 1, C | 1, C | — | 1, C | 1, C |
| Maleic acid | — | — | — | — | — | — |
| Phosphoric acid | 1, PC | A | 2, PC | — | 1, PC | — |

TABLE 3.3-continued

| | | | | | | |
|---|---|---|---|---|---|---|
| (+)-L-Tartaric acid | A | U | 1, PC | — | 1, PC | 1, C |
| Fumaric acid | 1, PC | 2, C | 2, C | — | 1, PC | 3, C |
| Citric acid | A | U | — | — | A | A |
| Succinic acid | — | U | — | — | 1, C | — |
| Benzoic acid | — | — | — | — | — | — |

Key

| | | | |
|---|---|---|---|
| A | Amorphous | # | Pattern number |
| C | Crystalline potential salt | PC | Poorly crystalline |
| U | Counterion (unreacted) | — | No solids |

TABLE 3.4

Summary of dry XRPD analysis from primary formation assessment

| Counterions | THF | Ethyl Acetate | Ethanol | IPA: Water 50:50% v/v | MEK | MeCN |
|---|---|---|---|---|---|---|
| Hydrochloric acid | 1, C | 1, PC | 1, C | — | 1, C | 1, C |
| Sulfuric acid | — | — | — | — | — | — |
| p-Toluenesulfonic acid | — | — | — | — | — | — |
| Methanesulfonic acid | — | — | — | — | — | — |
| Benzenesulfonic acid | 1, C | 1, C | 1, C | — | 1, C | 1, C |
| Maleic acid | — | — | — | — | — | — |
| Phosphoric acid | 1, PC | A | 2, PC | — | 1, PC | — |
| (+)-L-Tartaric acid | 1, PC | U | 1, PC | — | 1, PC | 1, C |
| Fumaric acid | 1, PC | 2, C | 2, C | — | 1, PC | 3, C |
| Citric acid | A | U | — | — | A | A |
| Succinic acid | — | U | — | — | 1, C | — |
| Benzoic acid | — | — | — | — | — | — |

Key

| | | | |
|---|---|---|---|
| A | Amorphous | # | Pattern number |
| C | Crystalline potential salt | PC | Poorly crystalline |
| U | Counterion (unreacted) | — | No solids |

TABLE 3.5

Summary of 40° C./75% RH XRPD analysis from primary formation assessment

| Counterions | THF | Ethyl Acetate | Ethanol | IPA: Water 50:50% v/v | MEK | MeCN |
|---|---|---|---|---|---|---|
| Hydrochloric acid | 1, C | A | 1, C | — | 1, C | 1, C |
| Sulfuric acid | — | — | — | — | — | — |
| p-Toluenesulfonic acid | — | — | — | — | — | — |
| Methanesulfonic acid | — | — | — | — | — | — |
| Benzenesulfonic acid | 1, C | 1, C | 1, C | — | 1, C | 1, PC |
| Maleic acid | — | — | — | — | — | — |
| Phosphoric acid | 3, C | 3, C | 3, C | — | 3, C | — |
| (+)-L-Tartaric acid | A | A | A | — | A | 1, PC |
| Fumaric acid | 1, C | 1, C | 1*, C | — | ¼, C | ¼, C |
| Citric acid | A | A | — | — | A | A |
| Succinic acid | — | U | — | — | A | — |
| Benzoic acid | — | — | — | — | — | — |

Key

| | | | |
|---|---|---|---|
| A | Amorphous | # | Pattern number |
| C | Crystalline potential salt | PC | Poorly crystalline |
| U | Counterion (unreacted) | — | No solids |
| * | Additional peaks | | |

A summary of the properties of the hydrochloride, besylate and fumarate salts are reported in Table 3.6 below in addition to FIGS. 5 to 16.

TABLE 3.6

Summary of salt properties

| | TGA/DSC | | | | | |
|---|---|---|---|---|---|---|
| | Weight Loss/ wt % (Temp/ ° C.) | Endothermic Events (onset/peak)/ ° C. | Exothermic Events (onset/peak)/ ° C. | HPLC Solid Purity/ % area | $^1$H NMR | Comments |
| Hydrochloride Pattern 1 | 2.1 (20-191) | 194/208 | N/A | 92.2 | Ethanol 0.5 wt % | Anhydrous, high potential melt, physically stable at 40° C./75% RH, solution degradation observed |
| Besylate Pattern 1 | 1.1 (20-196) | 138/149 | N/A | 91.5 | Benzenesulfonic acid 1.3 equiv. Ethanol 0.37 wt % | Anhydrous, physically stable at 40° C./75% RH, solution degradation observed |
| Phosphate Pattern 1 | 10.5 (20-211) | 82/113 | N/A | 93.4 | THF 2.3 wt % | Likely solvate. Physically unstable at 40° C./75% RH. Solution degradation observed. |
| Phosphate Pattern 2 | 9.0 (20-201) | N/A | N/A | 92.7 | Ethanol 1.6 wt % | Potential solvate/hydrate. Physically unstable at 40° C./75% RH |
| Phosphate Pattern 3 | 1.7 (20-119) 5.3 (119-199) 7.5 (199-300) | 103/113 | 167/171 218/230 | N/A | No residual solvents | Obtained from exposure to 40° C./75% RH, multiple weight losses in TGA. |
| Tartrate Pattern 1 | 2.3 (20-164) 35.9 (164-301) | 126/141 171/192 | N/A | 91.7 | Tartrate 1.1 equiv. No residual solvents | Potentially hydrate or anhydrous. Deliquescence observed at 40° C./75% RH. Solution degradation observed. |
| Fumarate Pattern 1 | 4.3 (20-168) 31.2 (168-336) | 143/153 | N/A | 90.4 | Fumarate 1.5 equivalents THF 1.7 wt % | Likely solvate. Physically stable at 40° C./75% RH, from THF. |
| Fumarate Pattern 2 | 5.7 (72-159) 31.1 (159-330) | 141/152 200/205 | N/A | 94.4 | Fumarate 1.3 equivalents Ethanol 2.9 wt % | Likely solvate. Physically unstable at 40° C./75% RH. Solution degradation observed. |
| Fumarate Pattern 3 | 2.9 (112-175) 39.1 (175-304) | 139/147 186/207 | N/A | 96.9 | Fumarate 1.4 equivalents No residual solvents | Potentially anhydrous or hydrate. Physically unstable at 40° C./75% RH. |
| Fumarate Pattern 1/4 | 7.7 (20-170) 30.6 (170-303) | 137/148 | N/A | 93.1 | Fumarate 1.2 equivalents No residual solvents | Obtained from exposure to 40° C./75% RH. |
| Succinate Pattern 1 | 2.5 (20-127) 56.0 (127-316) | 74/83 152/161 | N/A | 89.2 | Succinate 1.9 equivalents No residual solvents | Potentially anhydrous or hydrate. Low potential melt. Physically unstable at 40° C./75% RH. Solution degradation observed. |

As can be seen from the tables above no solids were isolated for the following counterions: sulfuric acid, p-toluenesulfonic acid, methanesulfonic acid, malic acid and benzoic acid. Additional experiments were performed on these counterions as described in the methodology section, however after temperature cycling and anti-solvent addition, no solids were observed.

The results from reactions with each acid where solids were formed are summarised in more detail below.

Hydrochloric Acid:

When hydrochloric acid was used, the following results and observations were obtained.

Figure 5:
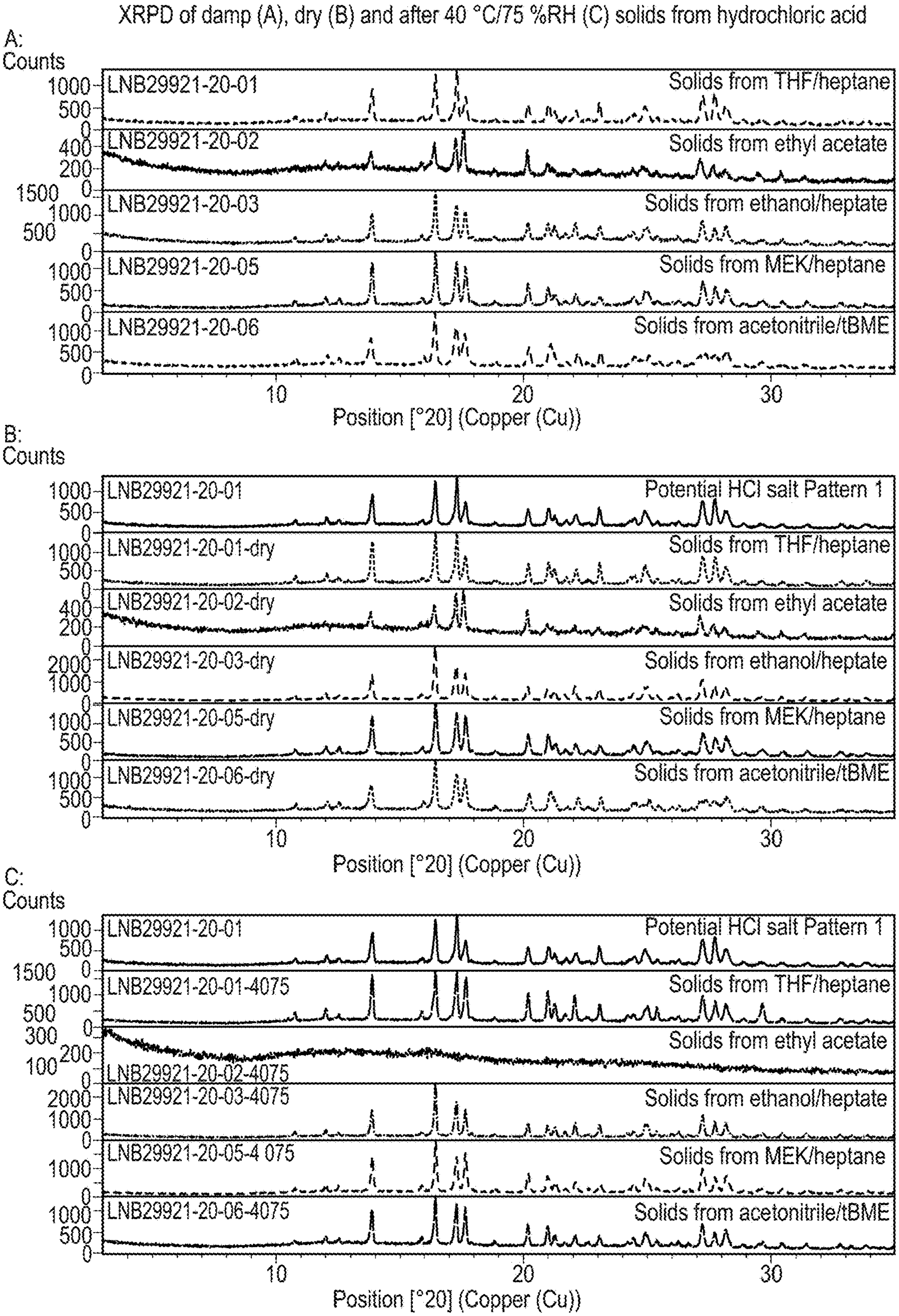
FIG. 5 shows an XRPD of damp (A), dry (B) and after 40° C./75% RH (C) solids from hydrochloric acid.

Solids of potential hydrochloride salt Pattern 1 were isolated from five solvent systems: THF, ethyl acetate, ethanol, MEK and acetonitrile. XRPD analysis indicated that hydrochloride salt Pattern 1 persisted after drying at 40° C. under vacuum and after storage at 40° C./75% RH as shown in FIG. 5.

Figure 6:
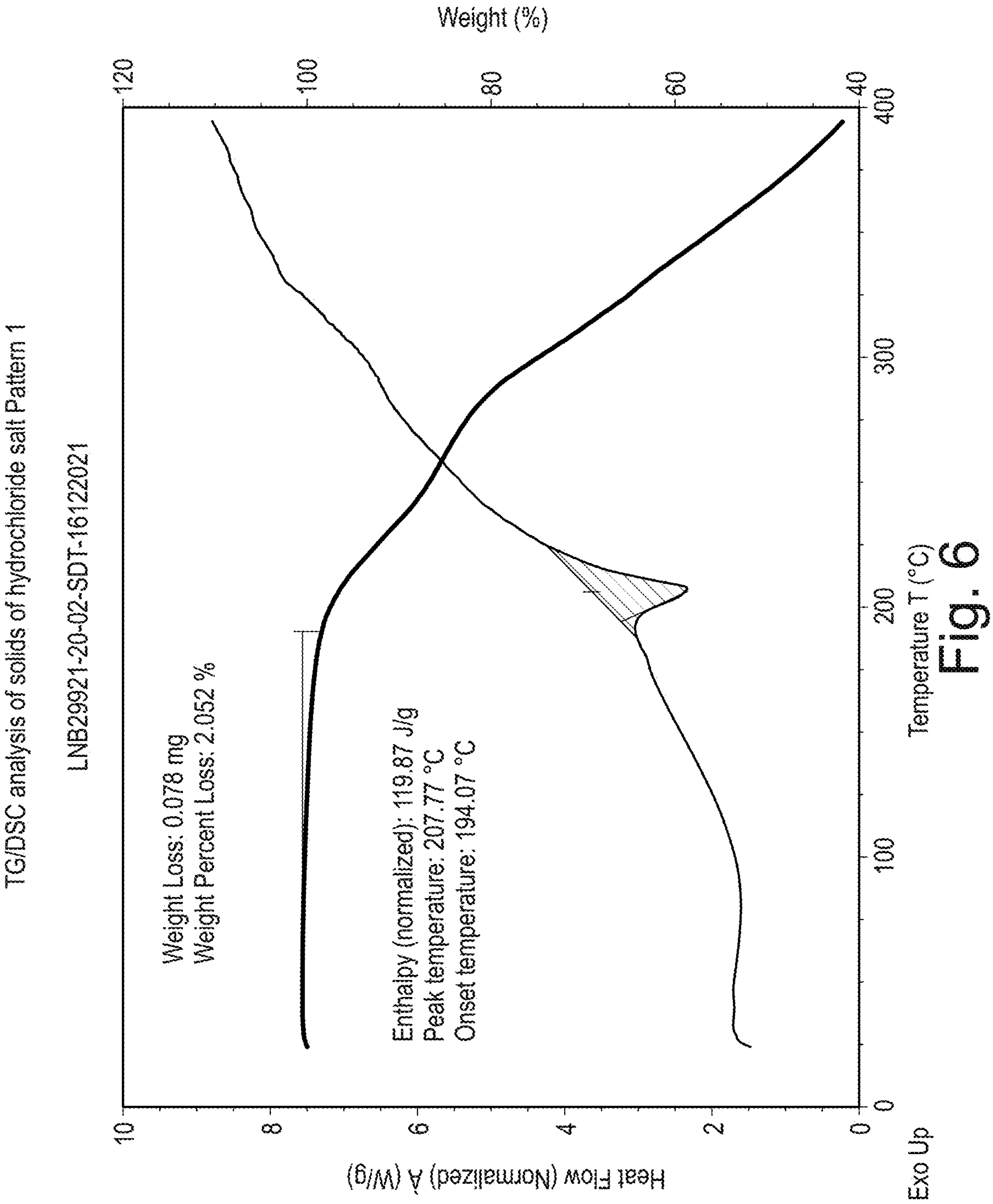
FIG. 6 shows a TG/DSC analysis of solids of hydrochloride salt Pattern 1.

TG/DSC analysis of the solids of hydrochloride salt Pattern 1, isolated from ethyl acetate, showed a weight loss of 2.1 wt % between 20-191° C. One endothermic event was observed with an onset temperature of 194° C., and a peak temperature of 208° C. as shown in FIG. 6.

Figure 7:
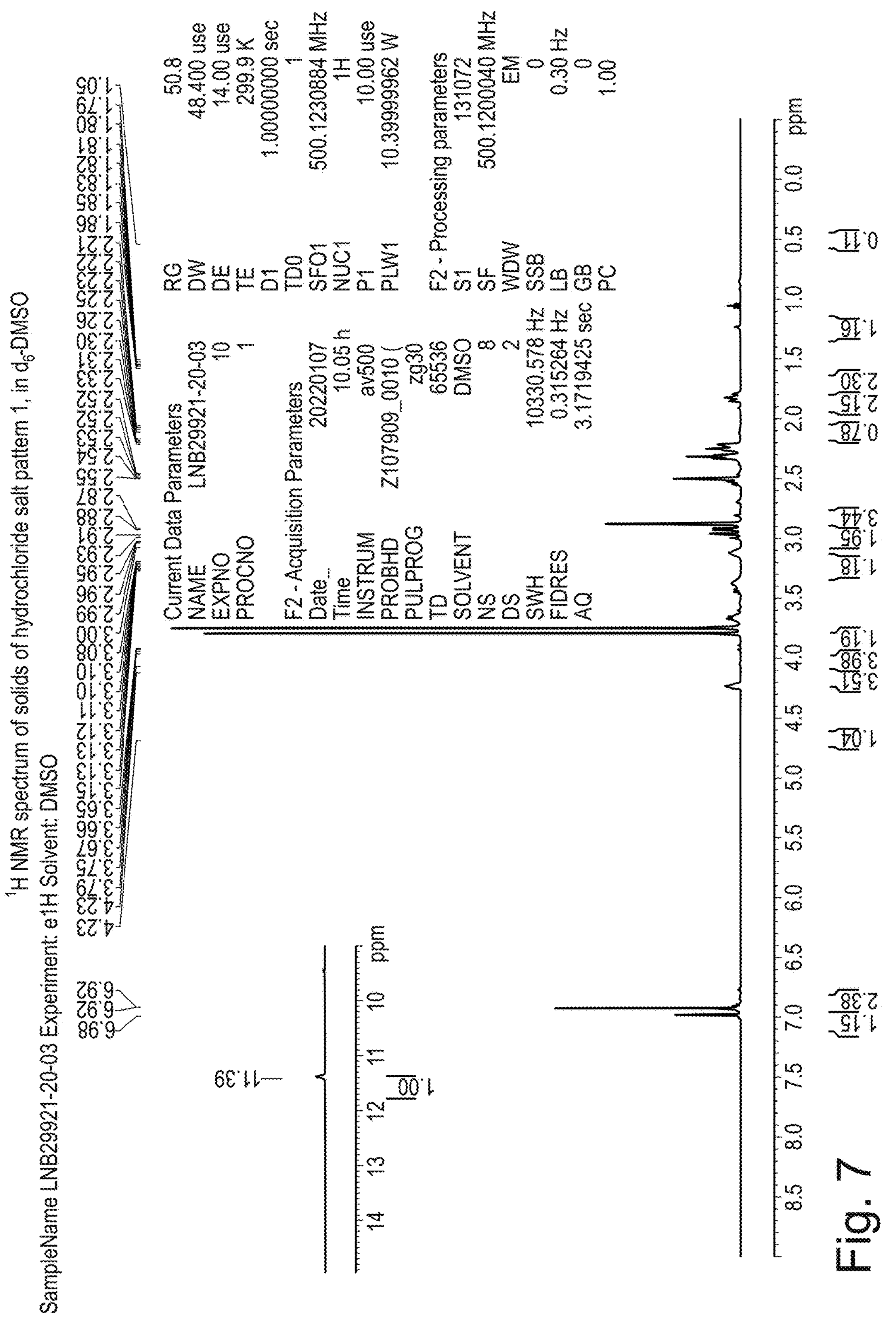
FIG. 7 shows a $^1$H NMR spectrum of solids of hydrochloride salt pattern 1, in $d_6$-DMSO.

The $^{1}H$ NMR spectrum of the solids of hydrochloride salt Pattern 1, isolated from ethanol, was consistent with the chemical structure of mesembrine, with an additional signal at 11.39 ppm, consistent with salt formation. The residual ethanol content was 0.5% wt as shown in FIG. 7.

Figure 8:
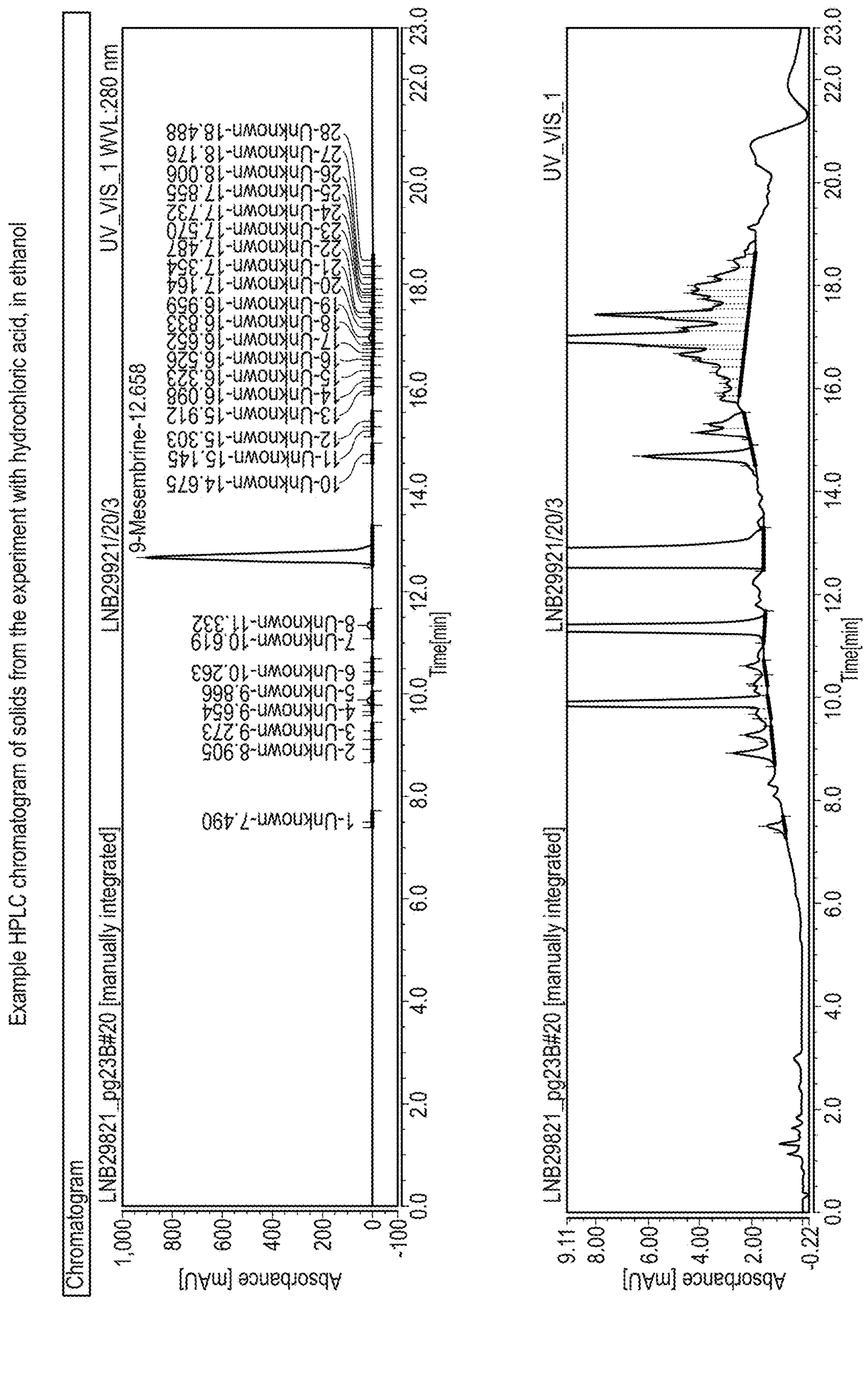
FIG. 8 shows an example HPLC chromatogram of solids from the experiment with hydrochloric acid, in ethanol.

HPLC analysis on the dried solids from ethanol showed the chemical purity was 92.2% area (c.f.: the input purity was 91.2% area) as shown in FIG. 8.

HPLC analysis on the filtered mother liquor from the experiment in ethyl acetate indicated the chemical purity was 40.3% area.

Benzenesulfonic Acid:

The results of the experiments with benzenesulfonic acid are summarized below.

Figure 9:
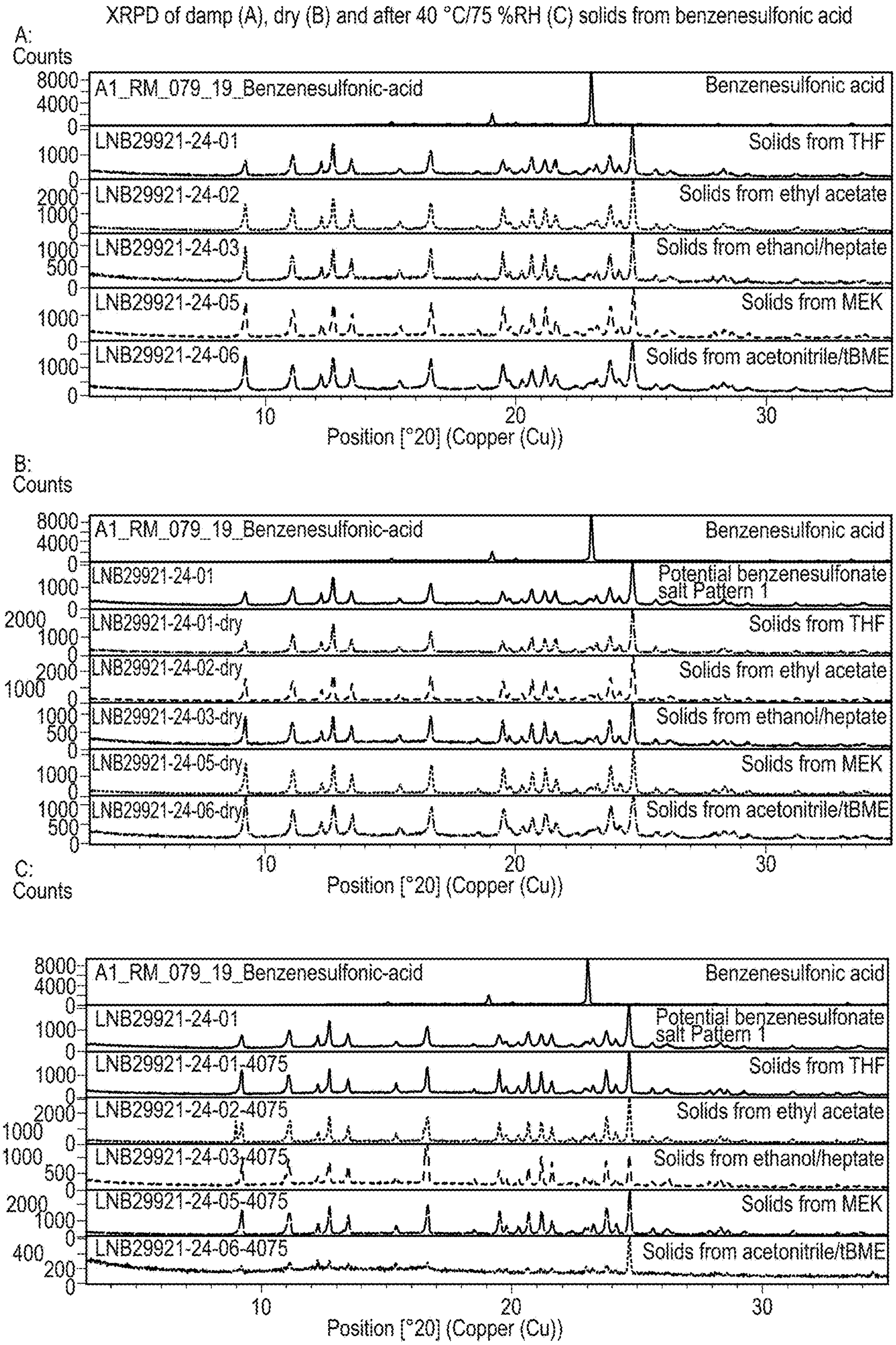
FIG. 9 shows an XRPD of damp (A), dry (B) and after 40° C./75% RH solids (C) from benzenesulfonic acid.

Solids of potential besylate salt Pattern 1 were isolated from five solvent systems: THF, ethyl acetate, ethanol, MEK and acetonitrile. This XRPD pattern persisted after drying at 40° C. under vacuum, and after storage at 40° C./75% RH as shown in FIG. 9.

Figure 10:
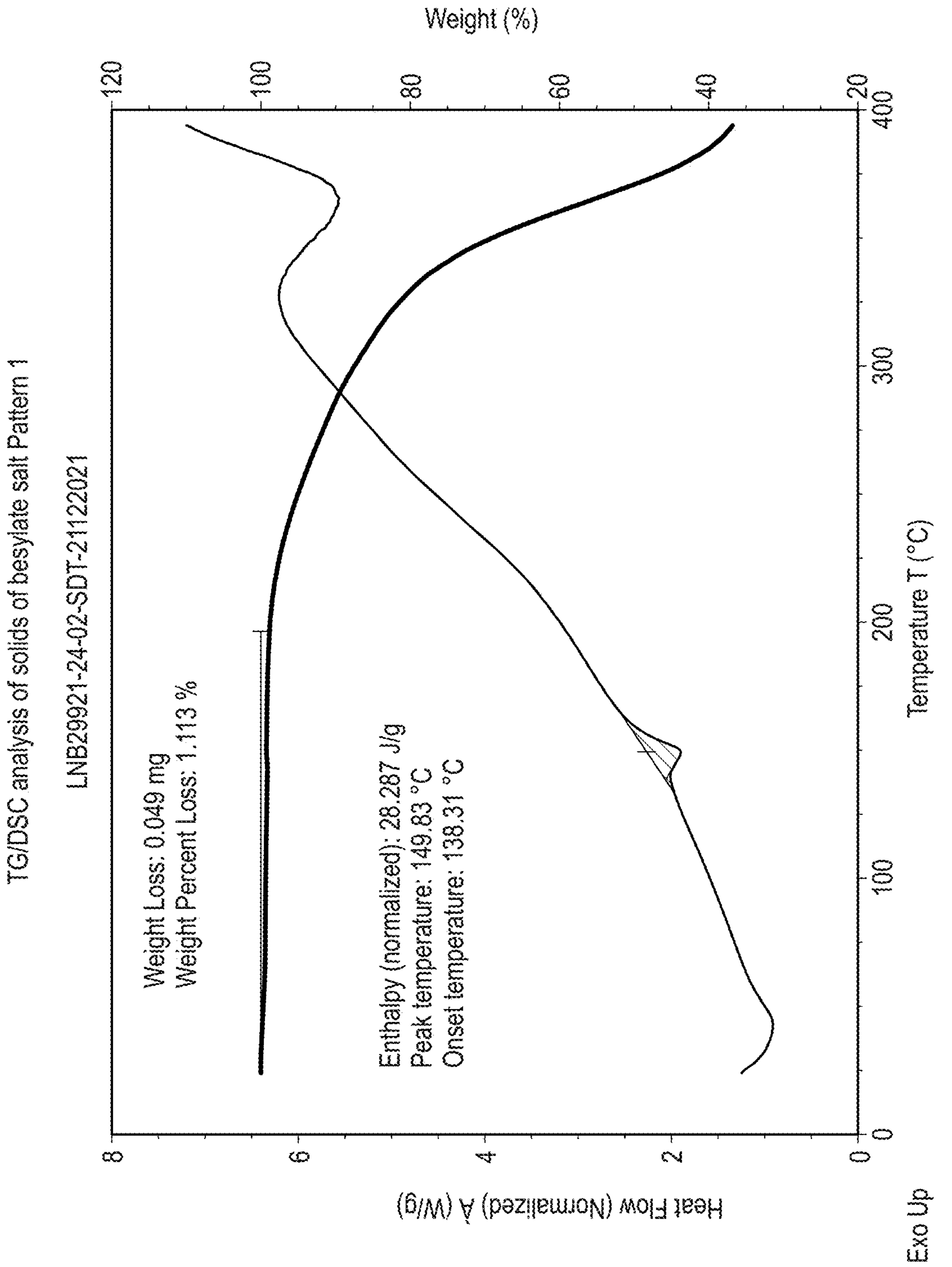
FIG. 10 shows a TG/DSC analysis of solids of besylate salt Pattern 1.

TG/DSC analysis of dried solids of besylate salt Pattern 1, isolated from ethyl acetate, showed a weight loss of 1.1 wt % between 20-196° C. In the DSC thermogram, one endothermic event was observed with an onset temperature of 138° C., and a peak temperature of 149° C. as shown in FIG. 10.

Figure 11:
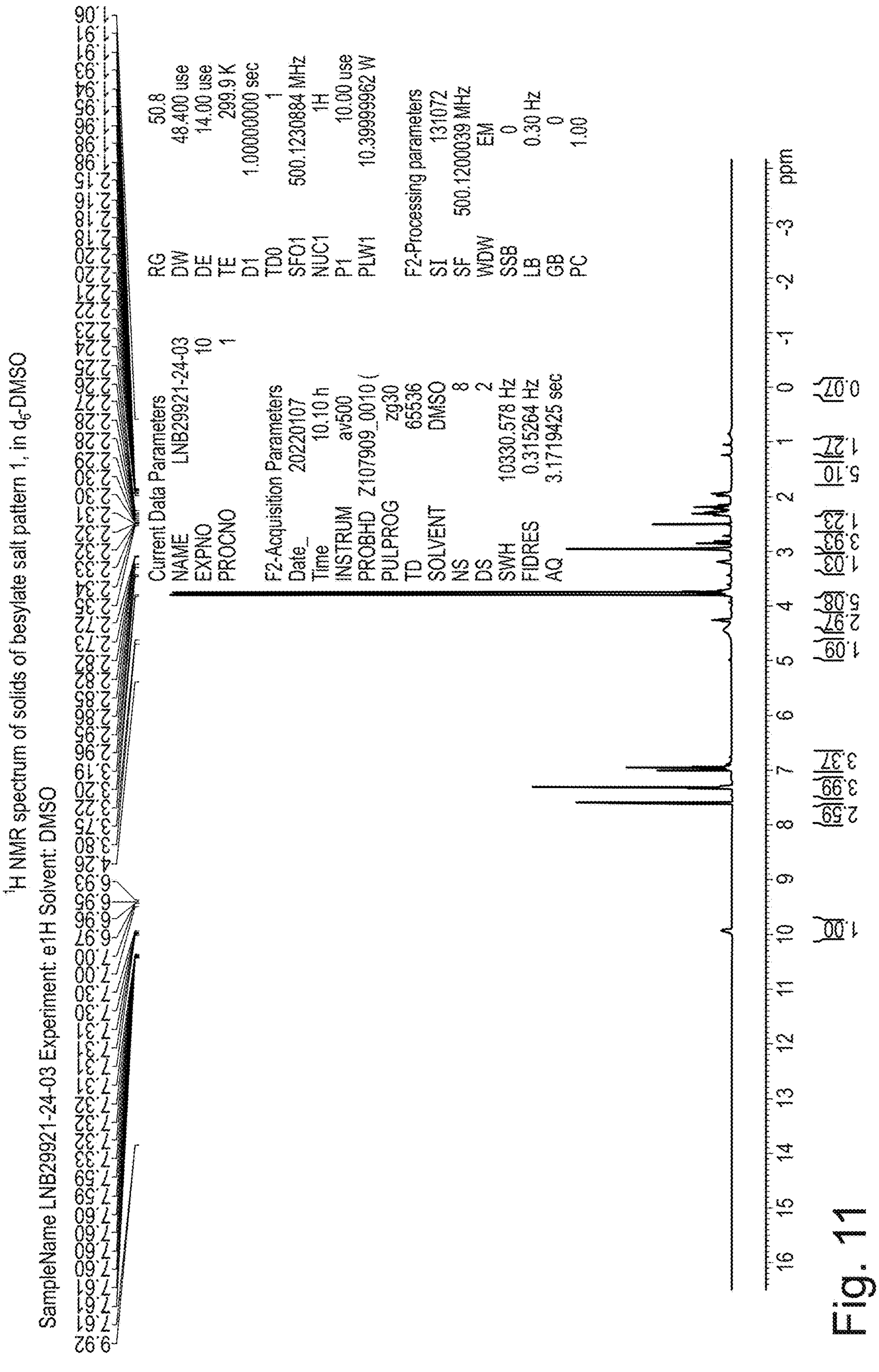
FIG. 11 shows a $^1$H NMR spectrum of solids of besylate salt pattern 1, in $d_6$-DMSO.

The $^{1}H$ NMR spectrum of solids of besylate salt Pattern 1, isolated from ethanol, was consistent with the structure of mesembrine, with an additional signal at 9.92 ppm, indicative with salt formation. Benzenesulfonic acid was also observed in the NMR spectrum, and the content was equal to 1.3 equivalents. A residual ethanol content of 0.37 wt % was observed as shown in FIG. 11.

Figure 12:
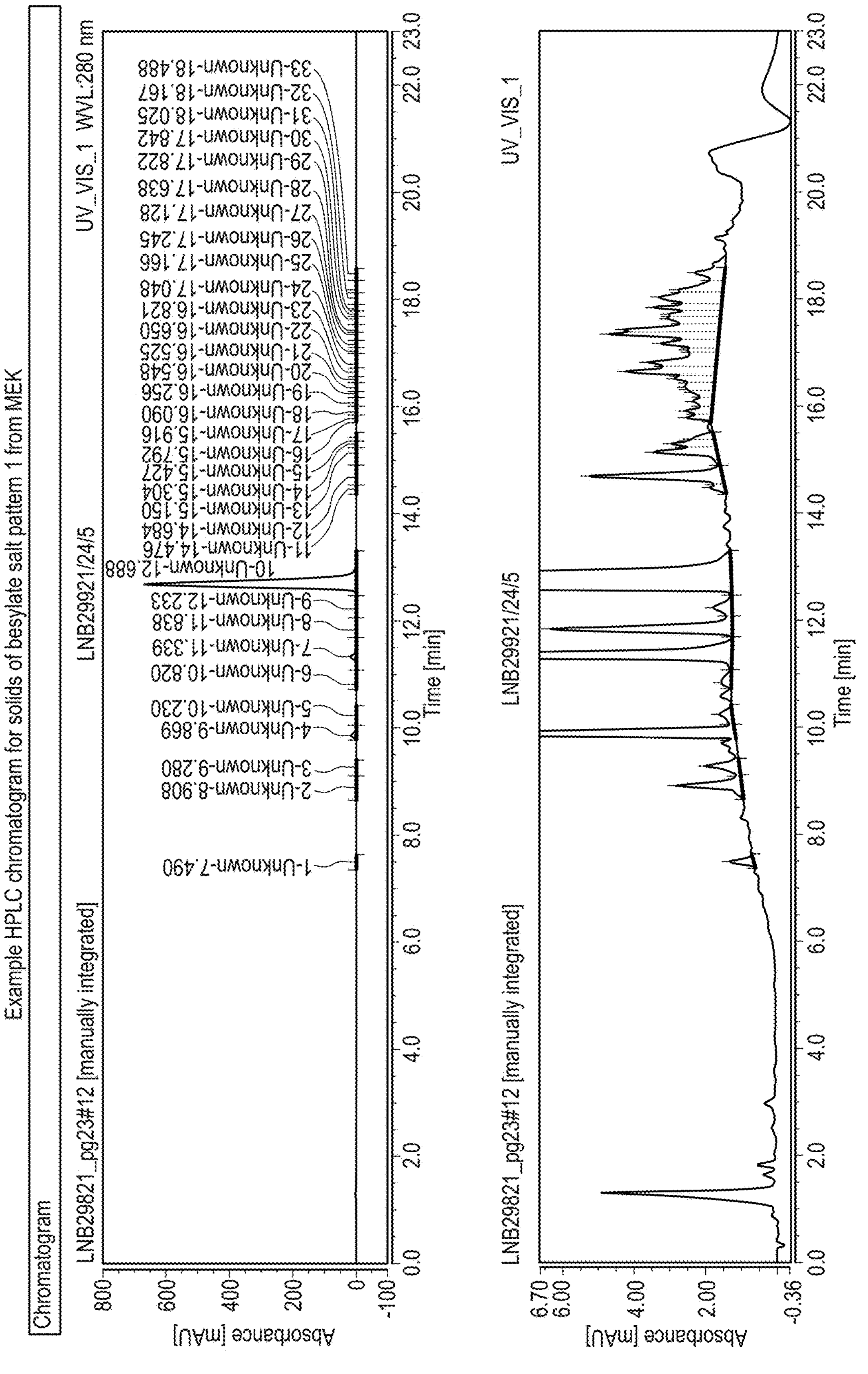
FIG. 12 shows an example HPLC chromatogram for solids of besylate salt pattern 1 from MEK.

HPLC analysis of the dried solids from the experiment in MEK indicated a chemical purity of 91.46% area (c.f.: the input purity was 91.2% area) as shown in FIG. 12.

HPLC analysis of the mother liquor from the experiment in ethyl acetate indicated a chemical purity of 44.21% area.

Phosphoric Acid:

The results of the experiments with phosphoric acid are summarized below.

Solids isolated from THF and MEK were poorly crystalline and labelled potential phosphate salt Pattern 1. After drying at 40° C. under vacuum solids of poorly crystalline phosphate Pattern 1 were maintained. After storage at 40° C./75% RH, the solids isolated from MEK had deliquesced but re-solidified out of the high humidity. For both materials, conversion to phosphate salt Pattern 3 was observed.

The solids isolated from the experiment in ethyl acetate were amorphous and remained amorphous after drying. After 24 h at 40° C./75% RH, conversion to phosphate Pattern 3 was observed.

The solids isolated from ethanol were poorly crystalline and labelled as potential phosphate salt Pattern 2. After drying at 40° C. under vacuum solids of poorly crystalline phosphate Pattern 2 were maintained, and after storage at 40° C./75% RH, conversion to phosphate salt Pattern 3 was observed.

HPLC analysis of the dried solids of phosphate salt Pattern 1, from THF, showed a chemical purity of 93.4% area. HPLC analysis of dried solids of phosphate salt Pattern 2, from ethanol, showed a chemical purity of 92.67% area.

The purity of the mother liquor from the experiment in MEK was 65.31% area.

TG/DSC analysis of solids of phosphate salt Pattern 1, from THF, showed a weight loss of 10.5 wt % between 20-211° C. In the DSC thermogram, one endothermic event was observed with an onset temperature of 82° C., and a peak temperature of 113° C.

The $^{1}H$ NMR spectrum of phosphate salt Pattern 1, isolated from THF, was consistent with the structure of mesembrine. A residual THF content of 2.3 wt % was observed. The 31P NMR analysis indicated a phosphate group was present in the material.

The TG/DSC analysis of solids of phosphate salt Pattern 2, from ethanol, showed a weight loss of 9.0 wt % between 20-201° C. In the DSC thermogram, no endothermic events were observed.

The $^{1}H$ NMR spectrum of phosphate salt Pattern 2, isolated from ethanol, was consistent with the structure of mesembrine. A residual ethanol content of 1.6 wt % was observed. The 31P NMR spectrum was consistent with the presence of a phosphate group within this material.

The TG/DSC analysis of solids of phosphate salt Pattern 3, obtained from THF after storage at 40° C./75% RH, showed a weight loss of 1.7 wt % between 20-119° C., followed by a second weight loss of 5.3 wt % between 119-199° C. a final weight loss of 7.5 wt % was observed between 199-300. In the DSC thermogram there was one endothermic event with an onset temperature of 103° C. and a peak temperature of 113° C. In the DSC thermogram there were also two exothermic events with onset temperatures of 167° C. and 218° C., and peak temperatures of 171° C. and 230° C.

The $^{1}H$ NMR spectrum of phosphate salt Pattern 3, isolated from MEK after storage at 40° C./75% RH was consistent with the structure of mesembrine. No residual solvent was detected. The 31P NMR spectrum indicated the presence of a phosphate group within the material.

(+)-L-Tartaric Acid:

The results of the experiments with (+)-L-tartaric acid are summarized below.

Solids of potential tartrate salt, Pattern 1, were isolated from ethanol and MEK, but were poorly crystalline, and from acetonitrile. After drying under vacuum, solids of tartrate salt Pattern 1 were maintained in solids from ethanol, MEK and acetonitrile. After exposing to 40 C/75% RH, the solids from ethanol and MEK had deliquesced and re-solidified on removal from the humidity chamber. These solids were amorphous. The solids from acetonitrile remained as tartrate salt Pattern 1, but with a decrease in crystallinity.

Solids of tartrate salt Pattern 1 were also observed in the solids isolated from THF, after drying at 40° C. under vacuum.

The solids of tartrate salt Pattern 1, isolated from THF, had a chemical purity of 91.70% area (c.f.: the input purity was 91.2% area) by HPLC.

The mother liquor for the experiment in acetonitrile had a chemical purity of 34.80% area.

TG/DSC analysis of solids of tartrate salt Pattern 1, from ethanol, showed a weight loss of 2.3 wt % between 20-164° C., followed by a second weight loss of 35.9 wt % between 164-301° C. Two endothermic events were observed in the DSC thermogram with onset temperatures of 126° C. and 171° C., and peak temperatures of 141° C. and 192° C.

The 1H NMR spectrum of solids of tartrate salt Pattern 1, isolated from acetonitrile, was consistent with the structure of mesembrine. Tartaric acid was observed, with a content equal to 1.1 equivalents. No residual acetonitrile was observed.

Fumaric Acid:

The results of the experiments with fumaric acid are summarized below.

Solids isolated from THF were poorly crystalline and labelled potential fumarate salt Pattern 1. After drying at 40° C. under vacuum this poorly crystalline Pattern 1 material persisted. After storage at 40° C./75% RH, an increase in crystallinity was observed, and the material remained Pattern 1.

Solids isolated from ethyl acetate were crystalline and labelled as potential fumarate salt Pattern 2. After drying at 40° C. under vacuum a mixture of fumarate Pattern 1 and Pattern 2 was observed by XRPD. After storage at 40° C./75% RH, conversion to fumarate salt Pattern 1 was observed.

Solids of fumarate salt Pattern 2 were also observed from ethanol, which persisted after drying. After exposure to 40° C./75% RH conversion to fumarate salt Pattern 1, with additional peaks, was observed.

Solids of poorly crystalline fumarate salt Pattern 1 were observed from MEK, and were maintained after drying at 40° C. under vacuum. Exposure to 40° C./75% RH resulted in conversion to a mixture of fumarate salt Pattern 1 and Pattern 4.

Solids isolated from acetonitrile were crystalline, and labelled as fumarate salt Pattern 3, and persisted after drying at 40° C. under vacuum. Exposure to 40° C./75% RH resulted in conversion to a mixture of fumarate salt Pattern 1 and Pattern 4.

Figure 13:
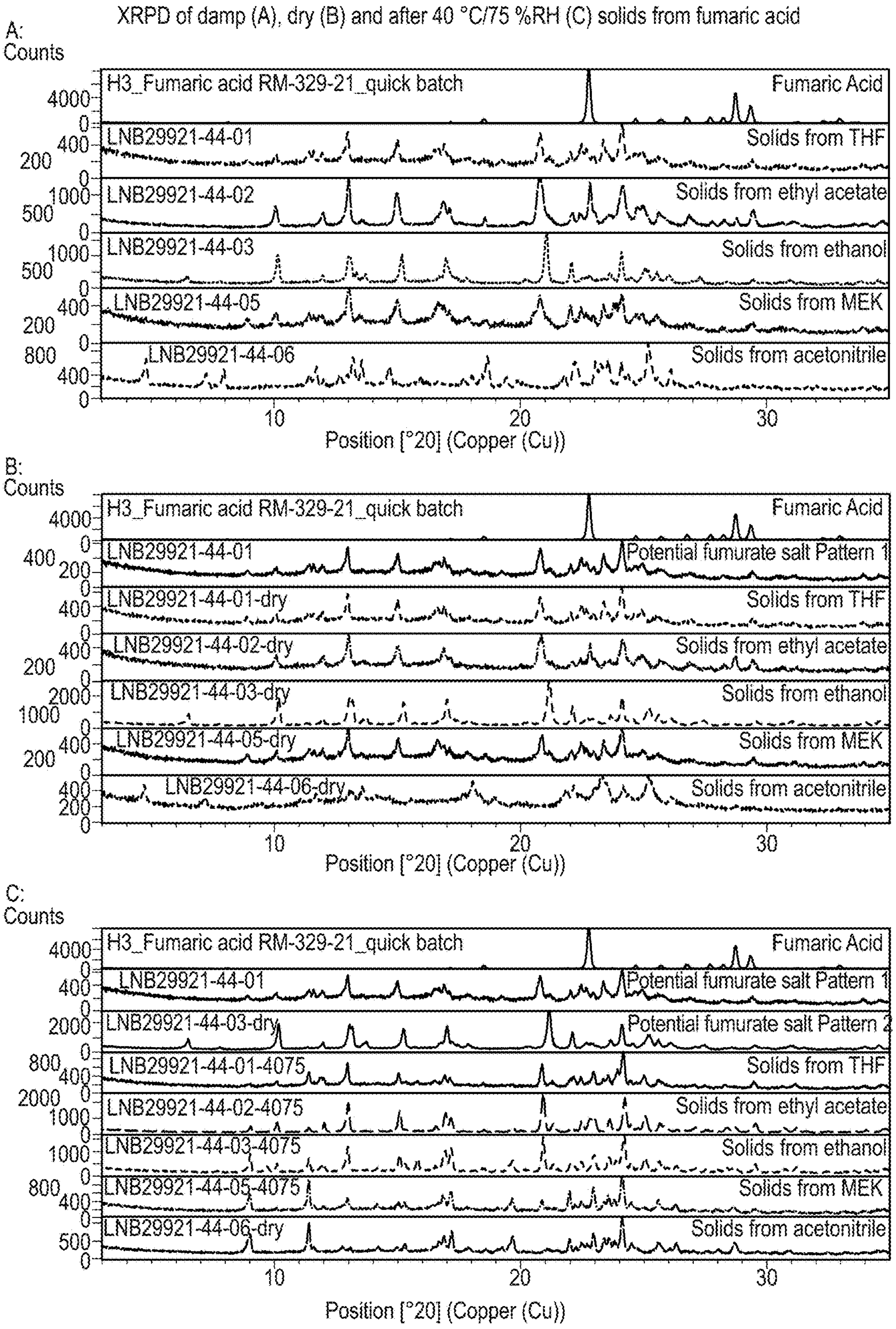
FIG. 13 shows an XRPD of damp (A), dry (B) and after 40° C./75% RH solids (C) from fumaric acid.

XRPD of the salt Patterns 1, 2 and 3 are shown in FIG. 13.

TG/DSC analysis showed the solids of fumarate salt Pattern 1, isolated from THF, showed a weight loss of 4.3 wt % between 20-168° C., followed by a second weight loss of 31.2 wt % between 168-336° C. One endothermic event was observed in the DSC thermogram with an onset temperature of 143° C. and a peak temperature of 153° C.

The $^1$H NMR spectrum of fumarate salt Pattern 1, isolated from THF, was consistent with the structure of mesembrine. The fumaric acid content was equal to 1.5 equivalents (30.7 wt %). The residual THF content was 1.7 wt %.

TG/DSC analysis showed the solids of fumarate salt Pattern 2, isolated from ethanol, showed a weight loss of 5.7 wt % between 72-159° C., and a second weight loss of 31.1 wt % between 159-330° C. There were two endothermic events in the DSC thermogram with onset temperatures of 141° C., and 200° C., and peak temperatures of 152° C. and 205° C.

The $^1$H NMR spectrum of fumarate salt Pattern 2, isolated from ethanol, was consistent with the structure of mesembrine. The fumaric acid content was equal to 1.3 equivalents (27.6 wt %). The residual ethanol content was 2.9 wt %.

TG/DSC analysis of solids of fumarate salt Pattern 3, isolated from acetonitrile, showed a weight loss of 2.9 wt % between 112-175° C., followed by a second weight loss of 39.1 wt % between 175-304° C. Two endothermic events were observed with onset temperatures of 139° C. and 186° C., and peak temperatures of 147° C. and 207° C.

The $^1$H NMR spectrum of fumarate salt Pattern 3, isolated from acetonitrile, was consistent with the structure of mesembrine. The fumaric acid content was equal to 1.4 equivalents. No residual acetonitrile was observed.

The TG/DSC analysis of solids of a mixture of fumarate salt Pattern 1 and Pattern 4, isolated from acetonitrile after storage at 40° C./75% RH, showed a weight loss of 7.7 wt % between 20-170° C., and a second weight loss of 30.6 wt % between 170-303° C. In the DSC thermogram, one endothermic event was observed with an onset temperature of 137° C. and a peak temperature of 148° C.

The $^1$H NMR spectrum of a mixture of fumarate salt Pattern 1+Pattern 4, isolated from MEK after exposure to 40° C./75% RH, was consistent with the chemical structure of mesembrine. The fumaric acid content was equal to 1.2 equivalents. No residual MEK was observed.

Figure 14:
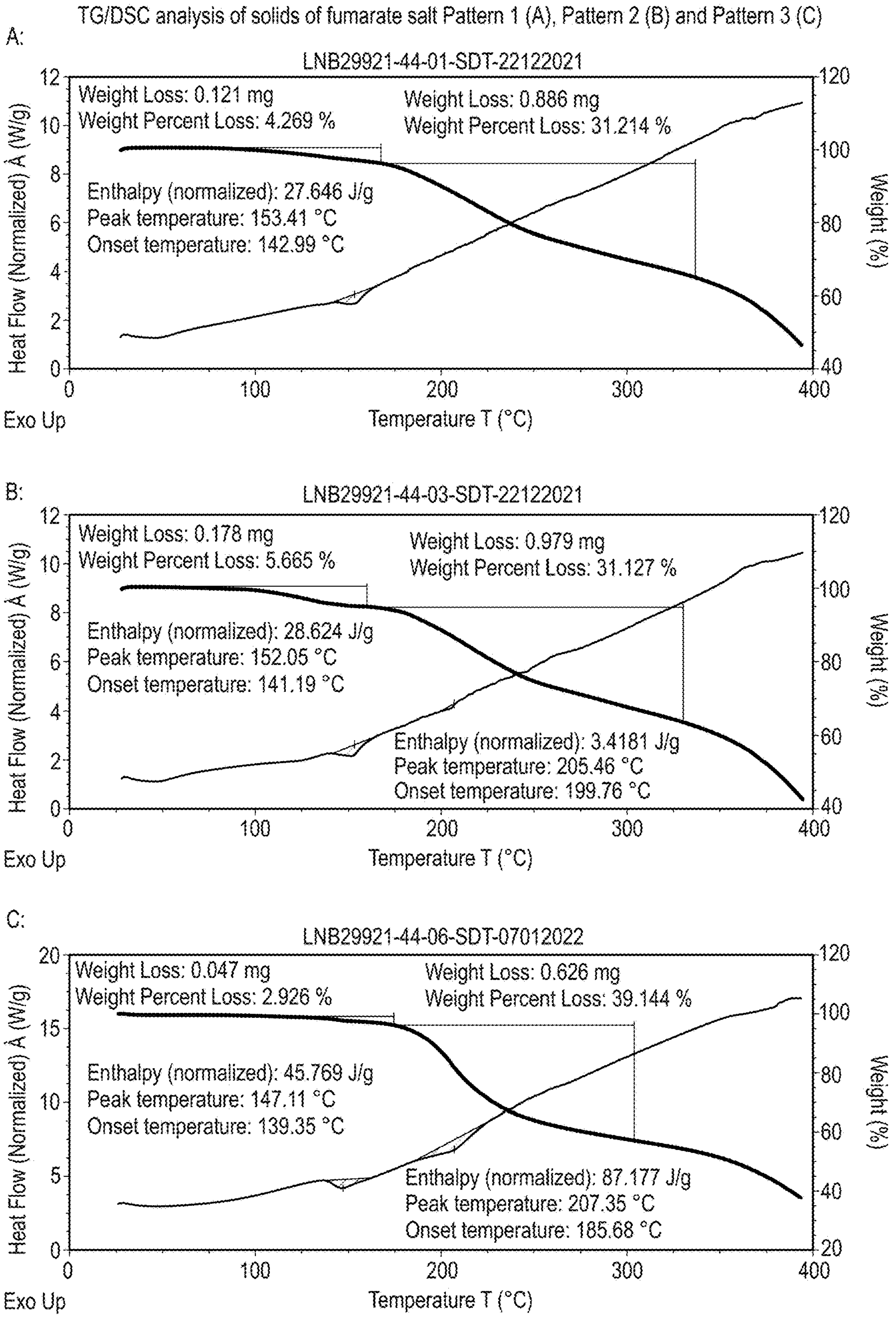
FIG. 14 shows a TG/DSC analysis of solids of fumarate salt Pattern 1 (A), Pattern 2 (B) and Pattern 3 (C)
Figure 15:
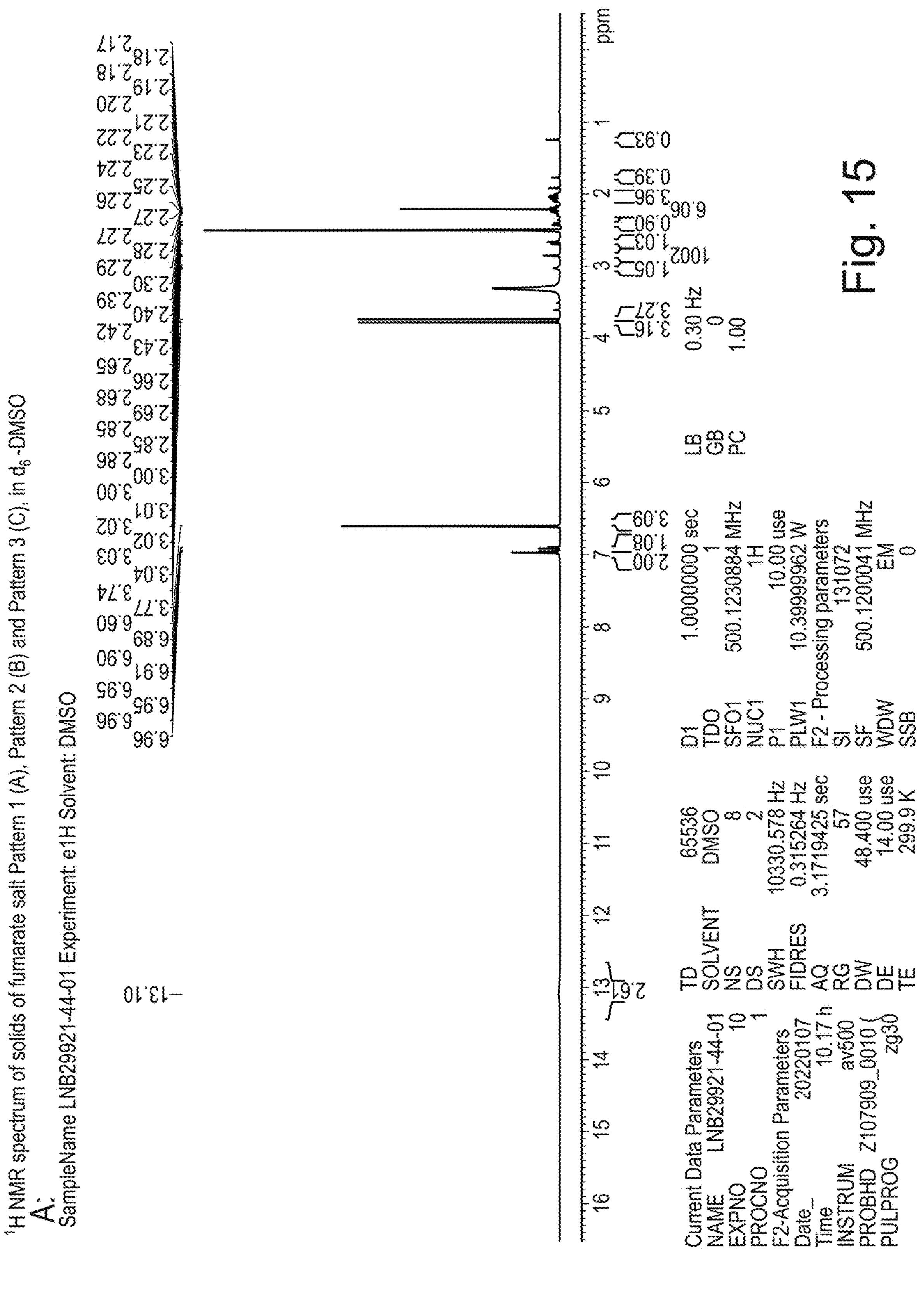
FIG. 15 shows a $^1$H NMR spectrum of solids of fumarate salt Pattern 1 (A), Pattern 2 (B) and Pattern 3 (C), in $d_6$-DMSO.
Figure 15:
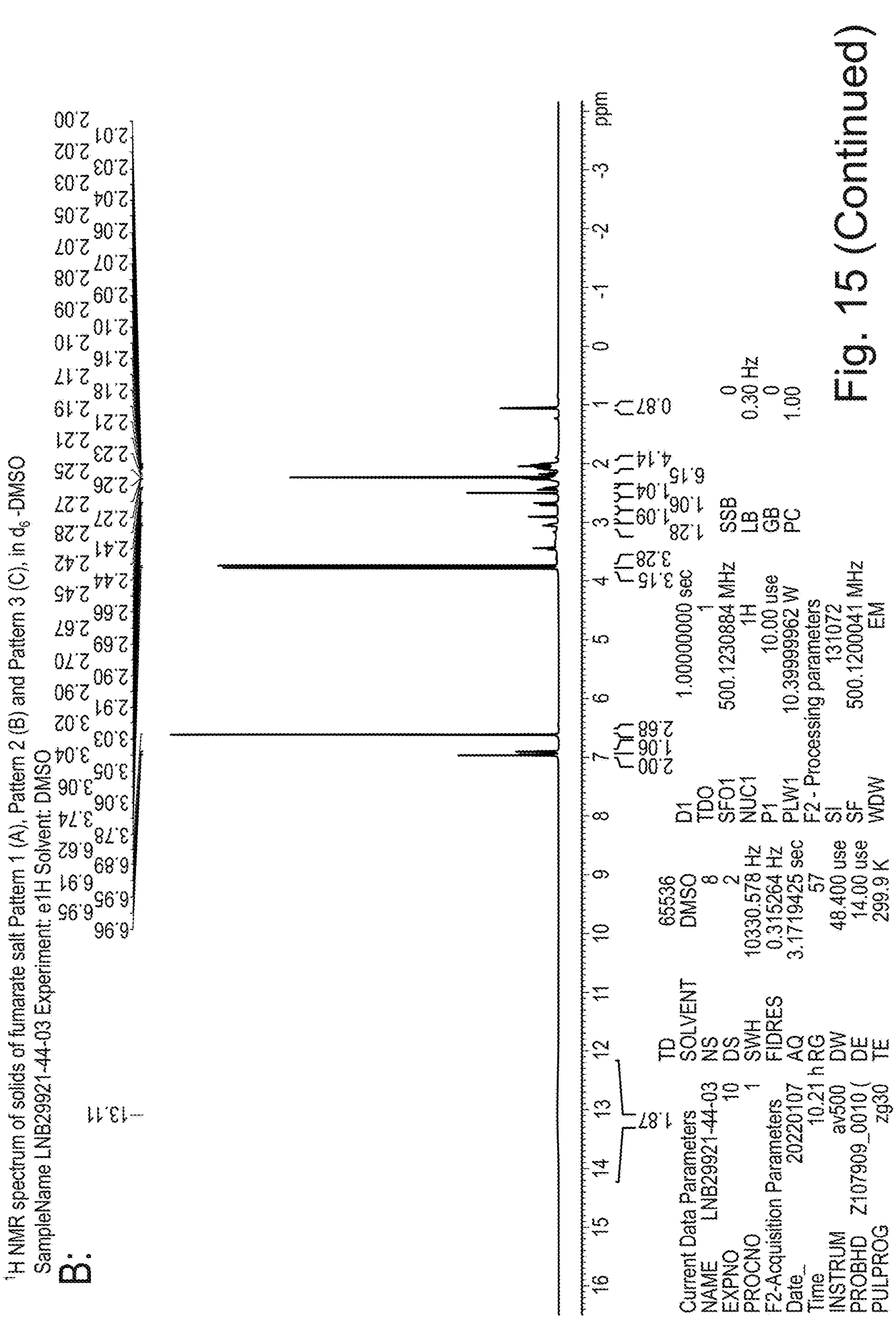
Figure 15:
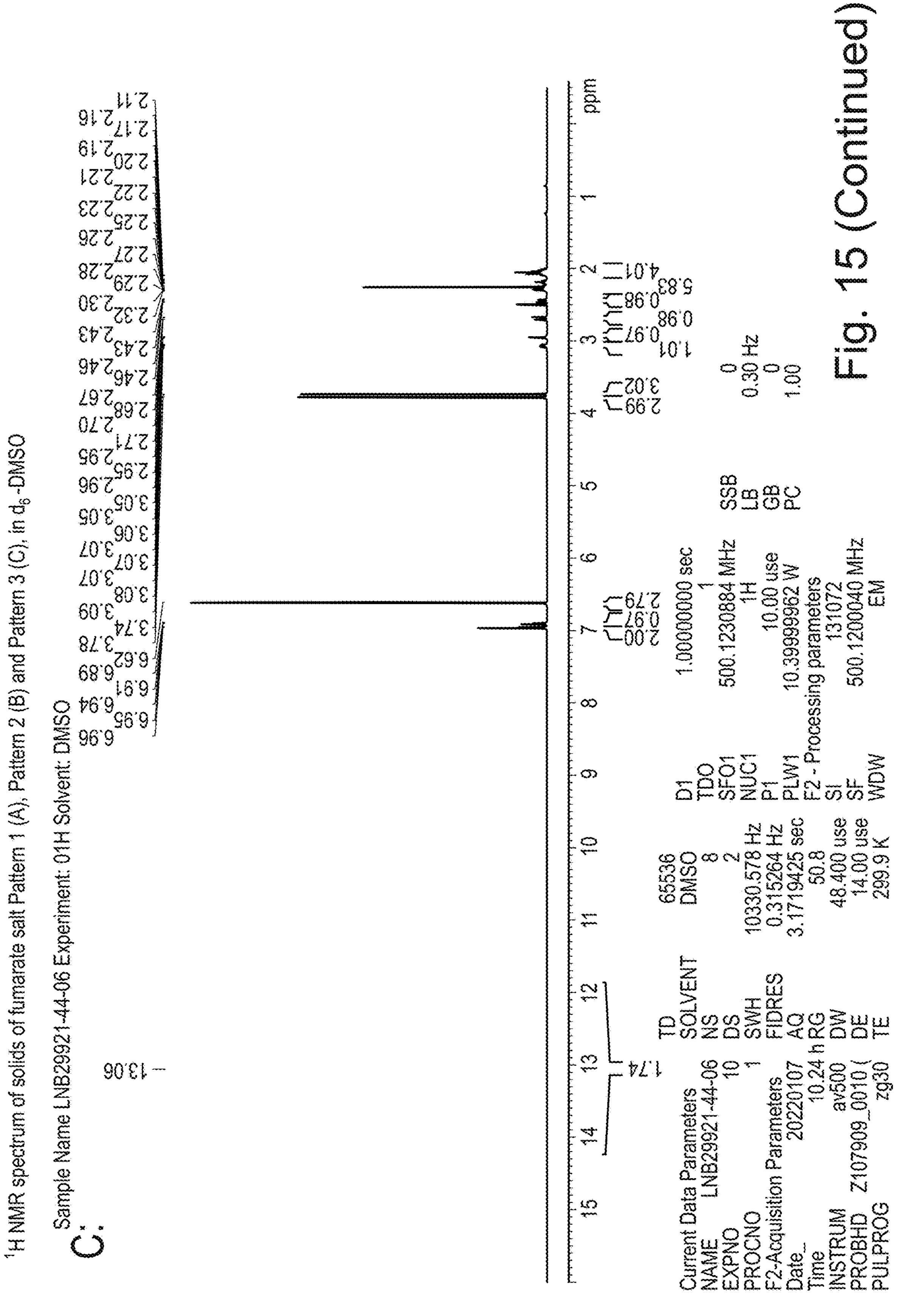

The TG/DSC for salt Patterns 1-3 are shown in FIG. 14 and the $^1$H NMR spectra for salt Patterns 1-3 are shown in FIG. 15.

Figure 16:
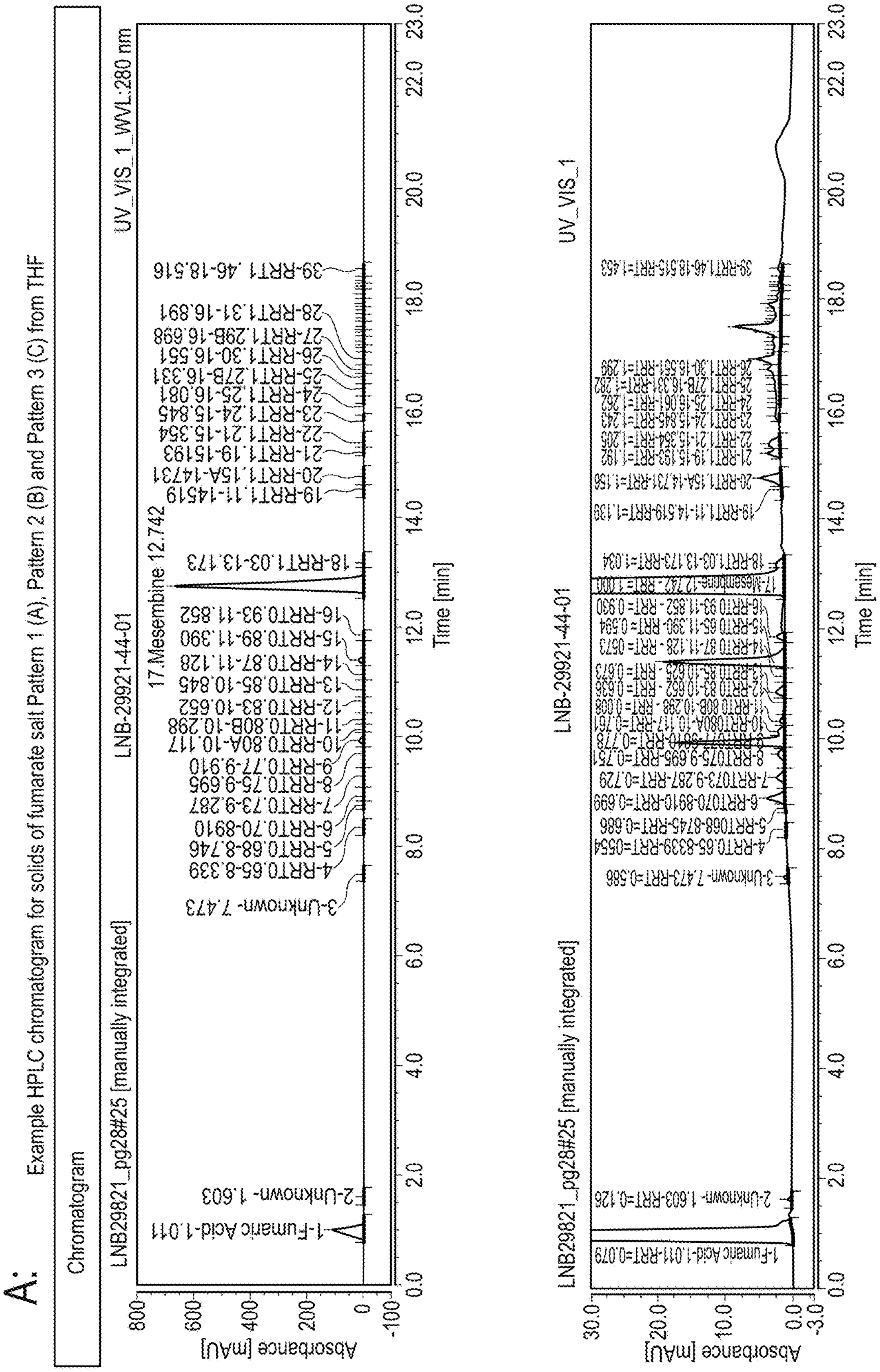
FIG. 16 shows an example HPLC chromatogram for solids of fumarate salt Pattern 1 (A), Pattern 2 (B), Pattern 3 (C) from THF.
Figure 16:
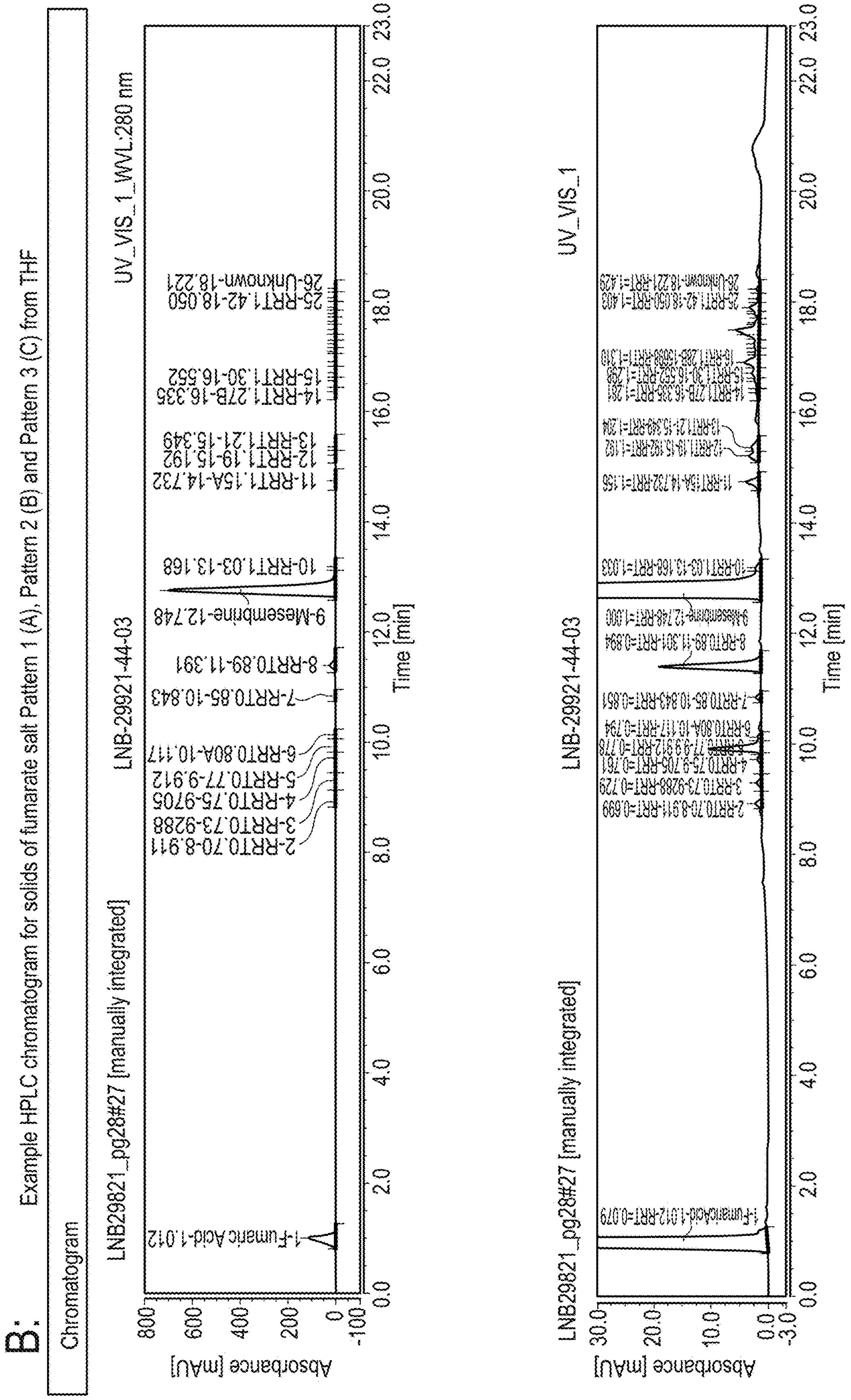
Figure 16:
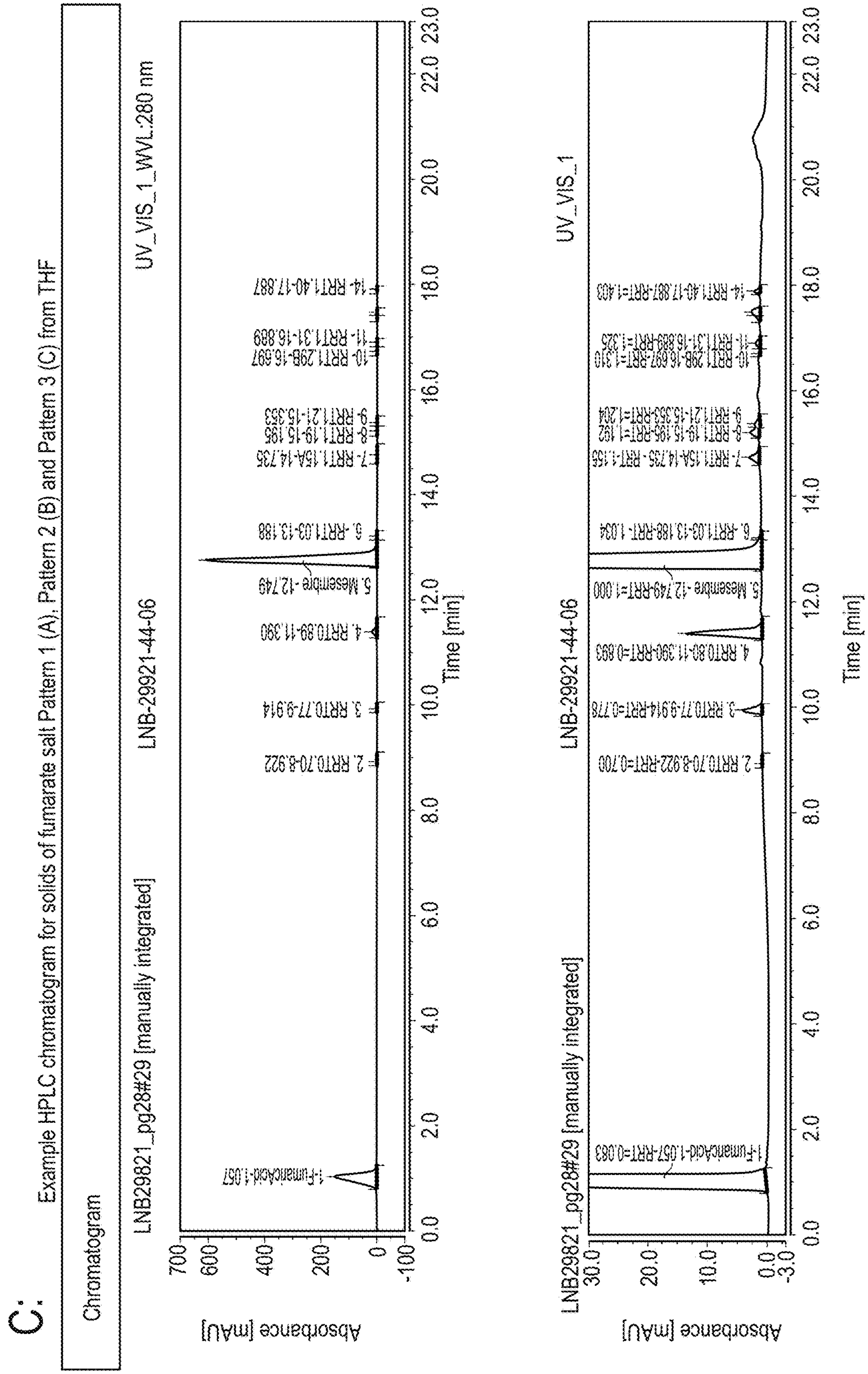

HPLC analysis showed a chemical purity of 90.36% area for the solids of fumarate salt Pattern 1, isolated from THF. The solids of fumarate salt Pattern 2, isolated from ethanol, had a chemical purity of 94.35% area. The solids of fumarate salt Pattern 3, isolated from acetonitrile, had a chemical purity of 96.47% area. The solids of a mixture of fumarate salt Pattern 1 and Pattern 4, isolated from MEK after exposure to 40° C./75% RH, was 93.1% area c.f.: the input purity was 91.2% area) as shown in FIG. 16.

Succinic Acid:

The results of the experiments with succinic acid are summarized below.

The solids isolated from MEK were crystalline and labelled potential succinate salt Pattern 1. This pattern persisted after drying at 40° C. under vacuum, however after exposure to 40° C./75% RH, conversion to amorphous material was observed.

Solids of potential succinate salt Pattern 1 had a chemical purity of 89.2% area.

The TG/DSC analysis of potential succinate salt Pattern 1 showed a weight loss of 2.5 wt % between 20-127° C., followed by a second weight loss of 56.0 wt % between 127-316° C. In the DSC thermogram, two endothermic events were observed with onset (and peak) temperatures of 74° C. (83° C.), and 152° C. (161° C.).

The $^1$H NMR analysis of potential succinate salt Pattern 1 was consistent with the chemical structure of mesembrine. A succinic acid content of 35.9 wt % (1.9 equivalents) was observed. No residual solvents were detected.

Conclusion

The data detailed above demonstrates that the salts formed using the counterions hydrochloric acid, benzenesulfonic acid and fumaric acid were crystalline, anhydrous solids with high potential melt temperatures and able to demonstrate physical stability.

As such these counterions were selected for a secondary salt formation assessment.

Table 3.1 details the pKa of the various counterions tested in the salt formation assessment. It is generally accepted that a difference of at least 2 pKa units between the acid and base are required for proton transfer, and as such the stronger the acid (lower pKa) the more likely a salt is to form. It was therefore surprising that apart from hydrochloric acid the stronger acids such as sulfuric acid, p-toluenesulfonic acid, methanesulfonic acid were unable to form salts with mesembrine.

Example 4: Secondary Salt Formation Assessment

Materials and Methods

Hydrochloride Salt Pattern 1:

The following procedure was used for the scale-up of the Hydrochloride salt Pattern 1. Approximately 0.5 g of mesembrine was dissolved in 2.5 mL of ethanol. 1.1 equivalents of HCl (0.156 mL) were dissolved in 2.5 mL of ethanol, and added to the solution of mesembrine, at 25° C. (Initial concentration: 100 mg/mL).

The experiment was stirred for ca. 1 h, then cooled to 5° C. at 0.1° C./min. After ca. 18 h at 5° C., 200 μL was sub-sampled and centrifuged and the solids analysed by XRPD.

The solids were predominately amorphous, so the experiment was heated to 25° C. over 10 minutes, and 15 mL of heptane was added over 30 minutes. The experiment was then cooled to 5° C. at 0.1° C./minute and held at 5° C. After ca. 2 h at 5° C., 200 μL was sub-sampled and centrifuged and the solids analysed by XRPD. The mother liquor was biphasic.

The solids were poorly crystalline, so the experiment was temperature cycled between 25° C. and 5° C. at 0.1° C./min, with 1 h holds at 25° C. and 5° C., for ca. 18 h. At 5° C., the solids were isolated by Buchner filtration and analysed by XRPD. The solids were dried at 40° C. under vacuum for ca. 72 h and then further characterization carried out.

Besylate Salt Pattern 1:

The following procedure was used for the scale-up of the Besylate salt Pattern 1.

Approximately 0.5 g of mesembrine was dissolved in 2.5 mL of MEK. 1.1 equivalents of benzenesulfonic acid (306.78 mg) were dissolved in 2.5 mL of MEK, and added to the solution of mesembrine, at 25° C. (Concentration: 100 mg/mL).

The experiment was stirred for ca. 1.5 h. The experiment was then cooled to 5° C. at 0.1° C./minute and held at 5° C. for ca. 18 h. A sub-sample (200 μL) was taken and centrifuged, and the solids analysed by XRPD.

The solids were isolated by Buchner filtration and dried at 40° C. under vacuum for ca. 18 h before being characterized further.

Fumarate Salt Pattern 1+Pattern 4 (Mixture):

The following procedure was used for the scale-up of the fumarate salt Pattern 4.

Approximately 0.5 g of mesembrine was dissolved in 2.5 mL of MEK. 1.1 equivalents of fumaric acid (222 mg) were dissolved in 2.5 mL of MEK, and the solution of mesembrine was added to the fumaric acid, dropwise at 25° C. (Concentration: 100 mg/mL).

The experiment was stirred for ca. 1 h at 25° C. The experiment was then cooled to 5° C. at 0.1° C./min and held at 5° C. for ca. 18 h. A sub-sample (200 μL) was taken and centrifuged, and the solids analysed by XRPD.

The slurry was very thick, therefore an additional 2 mL of MEK was added to improve slurry mobility, and stirred for ca. 30 min. The solids were isolated by Buchner filtration and dried at 40° C. under vacuum for ca. 18 h. The solids were analysed by XRPD, and then transferred to 40° C./75% RH.

After 5 days at 40° C./75% RH the solids were removed and further characterized.

The solids were sub-sampled after 1, 2 and 5 days for XRPD analysis.

Re-Preparation of Fumarate Salt Pattern 4:

The following general procedure was used for the re-preparation of the fumarate salt Pattern 4.

Approximately 103 mg of mesembrine was weighed into a vial and dissolved 0.52 mL of MEK at 25° C. 1.1 equivalents of fumaric acid was suspended in 0.52 mL of MEK. The mesembrine solutions were added to the fumaric acid at 25° C. and stirred.

The experiments were stirred for 1.5 h at 25° C. and then was cooled to 5° C. and 0.1° C./min and held at 5° C. for ca. 18 h before isolation. The solids were isolated by centrifugation. Solids were isolated and dried at 40° C. under vacuum for ca. 24 h.

Results

Hydrochloride Salt Pattern 1:

Solids of hydrochloride salt Pattern 1 were isolated in a 48% yield, with a chemical purity of 90.5% area. KF indicated a water content of 0.4% w/w. CAD indicated a chloride content of 0.9 equivalents, indicating the material is a mono-hydrochloride salt.

The solids were faint beige (BE10) with respect to the Sigma Aldrich colour chart.

TG/DSC analysis showed a weight loss of 1.7 wt % between 20-160° C., followed by a weight loss of 21.7 wt % between 162-273° C. An endothermic event with an onset temperature of 188° C. and a peak temperature of 200° C. was observed.

DSC analysis showed an endothermic event with an onset temperature of 182° C. and a peak temperature of 197° C.

VT-XRPD analysis showed that solids of hydrochloride salt Pattern 1 persisted between 25-160° C. At 188 and above (to 205° C.), the material was amorphous, and remained amorphous after cooling. The solids appeared to have melted.

Figure 17:
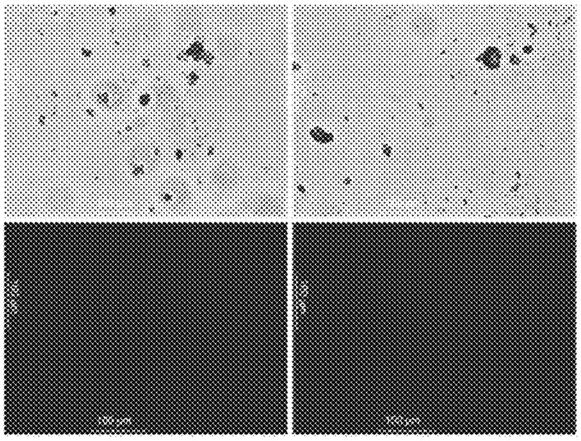
FIG. 17 shows a polarized light microscopy of hydrochloride salt Pattern 1 (A), besylate salt Pattern 1 (B) and fumarate salt Pattern 1 and 4 (C)
Figure 17:
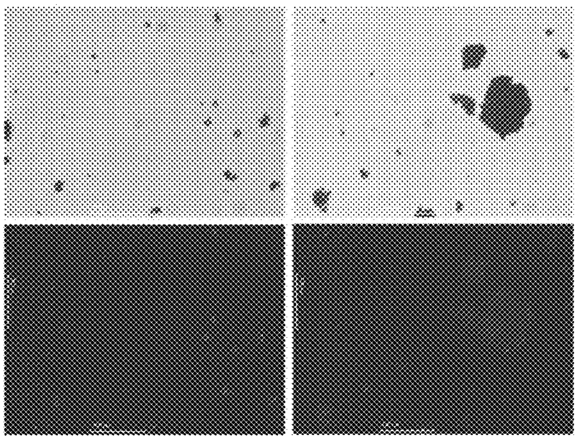
Figure 17:
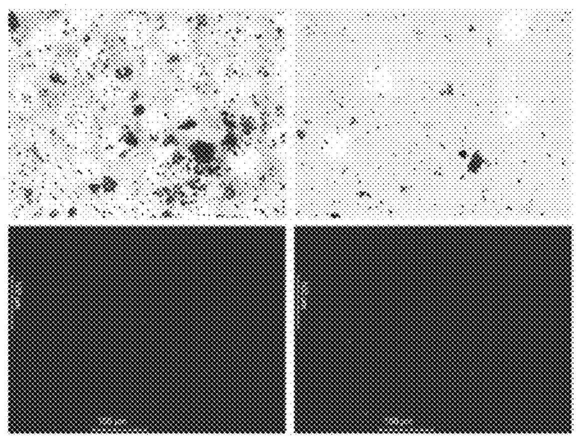

Polarized light microscopy (PLM) showed the material had no distinct morphology, with no apparent birefringence, see FIG. 17A.

An IR spectrum was recorded for reference.

The $^{1}H$ NMR spectrum was consistent with the formation of a salt of mesembrine. A residual ethanol content of 0.98 wt %, and a residual heptane content of 0.64 wt % was observed.

DVS analysis showed a water uptake of 5.4 wt % at 80% RH, and 25° C., indicating the material was hygroscopic. At 90% RH, the water uptake was 20.3 wt % indicating significant hygroscopicity above 80% RH. Solids of hydrochloride salt Pattern 1 were recovered from the DVS analysis.

VH-XRPD analysis showed that even after 12 h at 90% RH, the solids remained consistent with hydrochloride salt Pattern 1. No change in crystallinity was observed.

Besylate Salt Pattern 1:

Solids of besylate salt Pattern 1 were isolated in a 69% yield, with a chemical purity of 98.1% area. KF indicated a water content of 0.3% w/w.

The solids were faint beige (BE10) with respect to the Sigma Aldrich colour chart.

TG/DSC analysis showed a weight loss of 0.3 wt % prior to decomposition. In the DSC thermogram two endothermic events were observed with onset (and peak) temperatures of 131° C. (141° C.) and 151° C. (158° C.).

In the DSC, at a heating rate of 10° C./min, two overlapping endothermic events were observed in the first heat with onset (and peak) temperatures of 132° C.(141° C.) and 150° C.(158° C.). In the first cool a vitrification was observed with a mid-point half-height of 59° C., in the second heat a glass transition was observed with a mid-point half-height of 65° C. The DSC was repeated with a heating rate of 1° C./min which successfully resolved the endothermic events in the first heat, which were observed to have onset (and peak) temperatures of 129° C.(135° C.), and 151° C.(156° C.).

VT-XRPD analysis showed that solids of besylate salt Pattern 1 persisted between 25-150° C. At temperatures of 157° C. to 160° C., and after returning to 25° C., the material was amorphous, and appeared to have melted.

PLM indicated the material had no distinct morphology, with some birefringence, see FIG. 17B.

An IR spectrum was recorded for reference.

The $^1$H NMR spectrum was consistent with the formation of a salt of mesembrine. The benzenesulfonic acid content was 1.1 equivalents, indicating the material is a monobesylate salt.

DVS analysis showed that besylate salt Pattern 1 had a water uptake of 2.3 wt % at 80% RH and 25° C., indicating the material was hygroscopic. At 90% RH, the water uptake was 13 wt %, indicating significant hygroscopicity above 80% RH. Solids isolated at the end of the DVS analysis were consistent with besylate salt Pattern 1.

VH-XRPD analysis showed that even after 17 h at 90% RH, solids of besylate salt Pattern 1 persisted. There was no change in crystallinity during this analysis.

Fumarate Salt Pattern 1+Pattern 4 (Mixture):

Solids of a mixture of fumarate salt Pattern 1 and Pattern 4 were isolated in a 55% yield, with a chemical purity of 96.6% area. KF analysis indicated a water content of 4.0% w/w (ca. 1 equivalent water).

The solids were faint beige (BE10) with respect to the Sigma Aldrich colour chart.

TG/DSC analysis showed a weight loss of 3.4 wt % between 20-95° C., followed by second weight loss of 1.8 wt % between 95° C. and 162° C. In the DSC thermogram, two endothermic events were observed with onset (and peak) temperatures of 67° C.(80° C.), and 131° C.(154° C.).

In the DSC thermogram, two endothermic events were observed with onset (and peak) temperatures of 61° C.(75° C.), and 136° C.(152° C.).

VT-XRPD showed that between 25° C. and 90° C. a mixture of fumarate salt Pattern 1 and Pattern 4 persisted. At 130° C., the diffractogram was consistent with fumarate Pattern 4. At 154° C. and to 170° C., and after returning to ambient temperature the material was amorphous.

PLM showed the material had no distinct morphology, with limited birefringence, see FIG. 17C.

An IR spectrum was recorded for reference.

The $^1$H NMR spectrum was consistent with the salt formation of mesembrine. The fumaric acid content was equal to 1.3 equivalents, indicating this material is a monofumarate salt. A residual MEK content of 0.74 wt % was observed.

DVS analysis showed that at 80% RH and 25° C., the water uptake was 0.7 wt %, indicating that the material is slightly hygroscopic. Between 0-20% RH, a water uptake of 2.1 wt % was observed, indicating that at ambient humidity's the material is likely hydrated. The solids isolated at the end of the analysis were consistent with a mixture of fumarate salt Pattern 1 and Pattern 4.

VH-XRPD showed that between 40% RH and 10% RH, the solids were consistent with a mixture of fumarate salt Pattern 1 and Pattern 4. At 0% RH, a new diffractogram was observed, labelled fumarate Pattern 5.

Re-Preparation of Fumarate Salt Pattern 4:

XRPD showed Pattern 4 without Pattern 1 present. DVS analysis on fumarate salt Pattern 4 showed a water uptake of 0.5 wt % at 80% RH, 25° C., indicating the material was slightly hygroscopic. HPLC indicated the chemical purity was 95.88% area.

Conclusion

Salts were successfully formed from all three counterions and analysed accordingly. The three salts demonstrated properties consistent with improved attributes consistent with the ability to produce enhanced pharmaceutical formulations.

Example 5: Salt Hydration Study

Materials and Methods

Approximately 20 mg of the hydrochloride (HCl), besylate and fumarate salts were weighed into 3×2 mL push cap vials. 0.05-0.1 mL of relevant solvent system was added to each vial, at 25° C.

Methanol/water solvent systems (99:1, 75:25, 33:67) of known water activity ($a_w$ 0.2, 0.5 and 0.8 respectively) were used. The experiment was stirred for ca. 24 h. After 24 h, any slurries were centrifuged, and the solids analysed by XRPD.

An additional hydration study was required in order to repeat the salt hydration studies, for the HCl salt and the besylate salt due to dissolution in the first set of experiments:

For each salt, approximately 10 mg was weighed into 4×2 mL vials and a stirrer bar added. 10 μL of each solvent system was added, at 25° C. The experiments were stirred for 24 h, and any solids recovered were then analysed by XRPD.

Results

The results of the hydration studies are summarized in Table 3.7 below.

Clear solutions were obtained for the experiments with hydrochloride salt Pattern 1, and besylate salt Pattern 1.

Additional experiments with hydrochloride salt Pattern 1 resulted in slurries persisting at $a_w$ 0.5 and 0.8. The isolated solids were consistent with hydrochloride salt Pattern 1.

Clear solutions were obtained from the additional experiments with besylate salt Pattern 1, indicating the solubility was >1000 mg/mL.

Slurries were maintained for the fumarate salt. The isolated solids were consistent with fumarate salt Pattern 4.

TABLE 3.7

| Summary of Results from Hydration Studies | | | | |
|---|---|---|---|---|
| Salt | Concentration/mg/mL | Water Activity/$a_w$ | Observation | XRPD |
| Hydrochloride | 200 | 0.2 | Clear solution | — |
| Pattern 1 | 1000 | | | — |
| | 200 | 0.5 | Clear solution | — |
| | 1000 | | Slurry | 1, C |
| | 200 | 0.8 | Clear solution | |
| | 1000 | | Slurry | 1, C |
| Besylate | 200 | 0.2 | Clear solution | — |
| Pattern 1 | 1000 | | | |
| | 400 | 0.5 | Clear solution | — |
| | 1000 | | | |
| | 400 | 0.8 | Clear solution | — |
| | 1000 | | | |
| Fumarate | 400 | 0.2 | Thick slurry | 4, C |
| Pattern 1 + 4 | 400 | 0.5 | Slurry | 4, C |
| | 200 | 0.8 | Thick slurry | 4, C |

| Key | | | |
|---|---|---|---|
| A | Amorphous | # | Pattern number |
| C | Crystalline potential salt | PC | Poorly crystalline |
| U | Counterion (unreacted) | — | No solids |

Conclusion

The besylate salt was highly soluble resulting in greater than 1000 mg/ml at all levels of water activity, providing evidence that this salt is highly suitable for development of a pharmaceutical composition.

The hydrochloride salt was not soluble at higher concentrations and higher water activity levels. The fumarate did not produce a clear solution at any of the concentrations or water activity levels tested.

Example 6: pH Solubility Study

Materials and Methods

Approximately 20 mg of each salt was weighed into 3×2 mL push cap vials. 0.1 mL of buffer (Chloride pH 1.2; Acetate pH 4.5; Phosphate pH 6.8) was added to each vial, at 25° C. The experiment was stirred for ca. 24 h. After 2 h, the pH was measured and adjusted if required. After 24 h a final pH measurement was taken. Any slurries were centrifuged and the solids analysed by XRPD. The clear solutions/mother liquors were analysed by HPLC Results The results from the pH solubility study are summarized in Table 3.8:

High solubility (>96.75 mg/mL, with respect to mesembrine) was observed for hydrochloride salt Pattern 1 and besylate Pattern 1 across all pH ranges (1.2, 4.5, 6.8).

Solubility was 29.44 mg/mL for fumarate salt Pattern 1, at pH 1.2. Solids isolated from this experiment were consistent with fumaric acid.

Oiling was observed in the fumarate salt Pattern 1 experiment at pH 6.8.

TABLE 3.8

| Summary of Results from pH Studies | | | | | | | | | | |
|---|---|---|---|---|---|---|---|---|---|---|
| | | pH | | | | | HPLC | | | |
| Salt | Target PH | 2 h measured | 2 h adjusted | 24 h measured | Final pH | Observation | Purity/ % area | Conc./ mg/mL | XRPD |
| Hydrochloride | 1.2 | 1.2 | 1.25 | n/a | 1.48 | Clear solution | 97.09 | >105 | — |
| Pattern 1 | 4.5 | 4.5 | 4.49 | n/a | 4.34 | Clear solution | 93.45 | >146 | — |
| | 6.8 | 6.8 | 5.67 | 6.74 | 6.54 | Clear solution | 92.87 | >122 | — |
| Besylate | 1.2 | 1.2 | 1.18 | n/a | 1.18 | Clear solution | 98.01 | >172 | — |
| Pattern 1 | 4.5 | 4.5 | 5.55 | 4.55 | 3.72 | Clear solution | 98.02 | >140 | — |
| | 6.8 | 6.8 | 5.53 | 6.75 | 6.80 | Clear solution | 97.62 | >97 | — |
| Fumarate | 1.2 | 1.2 | 2.31 | 1.21 | 1.36 | Slurry | 96.31 | 29.44 | U |
| Pattern 1 + 4 | 4.5 | 4.5 | 3.28 | 4.49 | 4.53 | Clear solution | 96.07 | >24 | — |
| | 6.8 | 6.8 | 3.38 | 6.71 | 8.01 | Oil | 96.78 | 18.98 | — |

| Key | | | |
|---|---|---|---|
| A | Amorphous | # | Pattern number |
| C | Crystalline potential salt | PC | Poorly crystalline |
| U | Counterion (unreacted) | — | No solids |

Conclusion

The besylate salt and hydrochloride salts were highly soluble at all pH ranges, providing evidence that these salts would be suitable for development of a pharmaceutical composition.

The fumarate salt was only able to produce a clear solution at pH 4.5.

Example 7: Stability Study

Materials and Methods

A 1-week stability study was performed for hydrochloride salt Pattern 1, besylate salt Pattern 1, fumarate salt Pattern 1+4, and fumarate salt Pattern 4.

Approximately 5 mg of the salt was weighed into 3×2 mL push cap vials. The 2 mL vials were then each placed inside a 20 mL vial, with the lids on or off as required. The solids were placed under the required stability conditions for 1 week at the following three conditions: 40° C./75% RH (open); 80° C. (closed); Ambient light, temperature and humidity (open)

After 1-week, visual observations were noted, then the solids were analysed by XRPD and HPLC.

Results

The results from the 1-week stability studies are summarized in Table 3.9.

For hydrochloride salt Pattern 1, there was a slight increase in chemical purity observed from all stability conditions. Solids of hydrochloride salt Pattern 1 were isolated from all stability conditions.

For besylate salt Pattern 1, there was no decrease in chemical purity observed after 1 week at 40° C./75% RH, or ambient conditions. A small decrease in chemical purity was observed after 1 week at 80° C. Solids of besylate salt Pattern 1 were isolated from all conditions.

For fumarate salt Pattern 1+4, there was a slight decrease in chemical purity observed after 1 week at 40° C./75% RH, and the solids were consistent with a mixture of fumarate salt Pattern 1 and Pattern 4. A decrease in chemical purity was observed after 1 week at 80° C., with conversion to novel fumarate salt Pattern 6. No significant decrease in chemical purity was observed after 1 week at ambient conditions, and the solids had a XRPD diffractogram consistent with a mixture of fumarate salt Pattern 1 and Pattern 4.

For fumarate salt Pattern 4, solids of fumarate salt Pattern 4 were recovered from all stability conditions. There was a slight increase in chemical purity after 1-week at all stability conditions.

TABLE 3.9

Summary of Results from 1-week stability study

| Salt | Stability Condition | Observation * | HPLC/ % area | XRPD |
|---|---|---|---|---|
| Hydrochloride Pattern 1 | Input | Faint beige solids (BE10) | 90.5 | 1, C |
| | 40° C./75% RH (open) | Light brown solids (BR8) | 93.4 | 1, C |
| | 80° C. (closed) | Light brown solids (BR8) | 92.8 | 1, C |
| | Ambient light, temperature and humidity | Faint beige solids (BE10) | 91.5 | 1, C |
| Besylate Pattern 1 | Input | Faint beige solids (BE10) | 98.1 | 1, C |
| | 40° C./75% RH (open) | Light brown solids (BR8) | 98.0 | 1, C |
| | 80° C. (closed) | Faint beige solids (BE10) | 96.7 | 1, C |
| | Ambient light, temperature and humidity | Faint beige solids (BE10) | 98.1 | 1, C |
| Fumarate Pattern 1 + 4 | Input | Faint beige solids (BE10) | 96.6 | 1/4, C |
| | 40° C./75% RH (open) | Faint beige solids (BE10 | 95.6 | 1/4, C |
| | 80° C. (closed) | Light brown solids (BR8) | 83.4 | 6, C |
| | Ambient light, temperature and humidity | Faint beige solids (BE10 | 96.1 | 1/4, C |
| Fumarate Pattern 4 | Input | Faint beige solids (BE10) | 95.9 | 4, C |
| | 40° C./75% RH (open) | Faint beige solids (BE10) | 96.4 | 4, C |
| | 80° C. (closed) | Faint beige solids (BE10) | 96.4 | 4, C |
| | Ambient light, temperature and humidity | Faint beige solids (BE10) | 96.4 | 4, C |

Key

| | | | |
|---|---|---|---|
| A | Amorphous | # | Pattern number |
| C | Crystalline potential salt | PC | Poorly crystalline |
| U | Counterion (unreacted) | — | No solids |

* From the Sigma Aldrich colour chart

Conclusion

The besylate, hydrochloride and fumarate salt Pattern 4 were stable across all storage conditions, providing evidence that these salts would be suitable for development of a pharmaceutical composition.

The fumarate salt pattern 1 and 4 produced a novel salt type on storage at 80° C. was only able to produce a clear solution at pH 4.5.

Example 8: Scale-Up of Besylate Salt Pattern 1

Materials and Methods

A scale-up of the Besylate salt Pattern 1 was undertaken in order to fully characterise the salt of this form and to undertake a polymorph screen. An anti-solvent addition step was carried out to maximise the yield:

Approximately 4.5 g of mesembrine was weighed out and dissolved in 27.7 mL of MEK, and transferred to a 100 mL vessel at 25° C. Next 1.1 equivalents (2.79 g) of benzenesulfonic acid was weighed out and dissolved in 17.7 mL of MEK.

The stock solution of benzenesulfonic acid was added dropwise into the vessel, and the experiment stirred for 1 h at 25° C.

The experiment was cooled to 5° C. at 0.1° C./min. At 5° C., 15 mL of heptane was added over 3.3 h. The final solvent system was: MEK:heptane 75:25% v/v.

The experiment was then stirred at 5° C. for ca. 12 h. Crusting was observed on the walls of the vessel, and this was manually re-introduced into the slurry.

The solids were isolated by Buchner filtration and washed with 5 mL of MEK:heptane 75:25% v/v.

Prior to isolation, a sub-sample of solids was taken by centrifugation for XRPD analysis. The solids were dried at 40° C. under vacuum for ca. 29 h and used for further analysis and polymorph screening.

The besylate salt was then lyophilised to prepare amorphous material using the following procedure.

Approximately 50 mg of besylate salt Pattern 1 was weighed into a 2 mL push cap vial. The solids were dissolved in 0.5 mL of water, and then frozen at −20° C. Once frozen, the material was lyophilized. The isolated solids were then analysed by XRPD, TGA/DSC and HPLC.

Results

Figure 18:
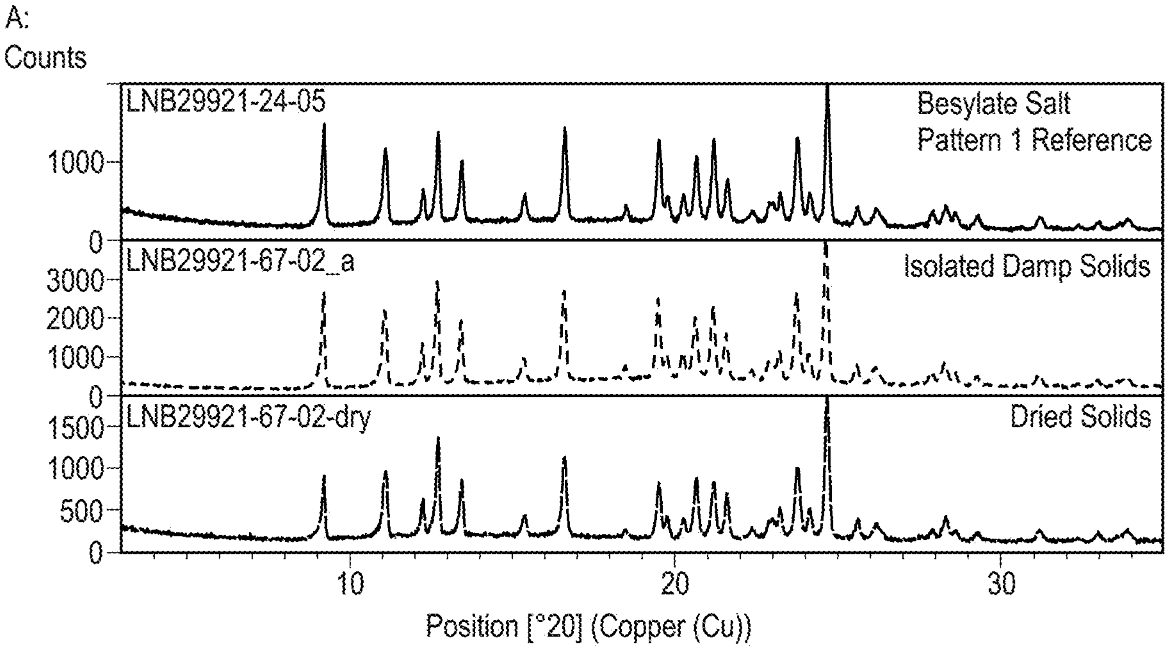
FIG. 18 shows an XRPD of solids from besylate salt Pattern 1 (A) and magnified dried solids (B)
Figure 18:
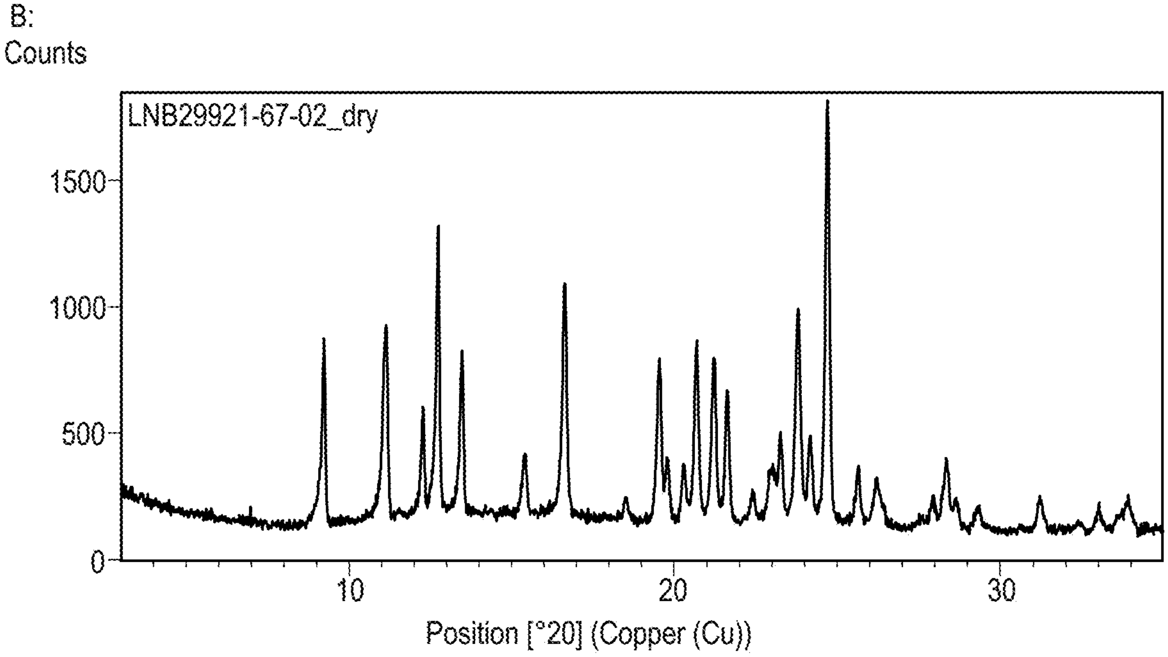

An XRPD of the solids from the scale-up experiment was prepared as detailed in FIG. 18. Details of the peaks are found in Table 3.10 below.

TABLE 3.10

XRPD Peaks for Besylate Salt Pattern 1

| Pos. [°2θ ] | Height [cts] | FWHM Left [° 2θ] | d-spacing [Å] | Rel. Int. [%] |
|---|---|---|---|---|
| 9.2289 | 699.40 | 0.0895 | 9.58280 | 43.47 |
| 11.0523 | 643.46 | 0.0512 | 8.00559 | 39.99 |
| 11.1405 | 761.35 | 0.0768 | 7.94241 | 47.32 |
| 12.2729 | 481.42 | 0.0895 | 7.21196 | 29.92 |
| 12.7303 | 1215.72 | 0.1023 | 6.95387 | 75.56 |
| 13.4672 | 684.26 | 0.1151 | 6.57500 | 42.53 |
| 15.4051 | 286.37 | 0.1023 | 5.75196 | 17.80 |
| 16.6247 | 950.78 | 0.1023 | 5.33263 | 59.09 |
| 18.5019 | 121.96 | 0.1023 | 4.79562 | 7.58 |
| 19.5198 | 651.77 | 0.1151 | 4.54778 | 40.51 |
| 19.7897 | 242.77 | 0.0768 | 4.48634 | 15.09 |
| 20.2578 | 240.37 | 0.1023 | 4.38373 | 14.94 |
| 20.6618 | 756.89 | 0.1023 | 4.29892 | 47.04 |
| 21.1937 | 670.33 | 0.1407 | 4.19221 | 41.66 |
| 21.5953 | 542.41 | 0.1023 | 4.11516 | 33.71 |
| 22.3994 | 126.07 | 0.1535 | 3.96921 | 7.84 |
| 22.8769 | 212.17 | 0.0768 | 3.88744 | 13.19 |
| 23.2193 | 390.41 | 0.0640 | 3.83088 | 24.26 |
| 23.7753 | 881.90 | 0.1279 | 3.74253 | 54.81 |
| 24.1351 | 372.81 | 0.0768 | 3.68755 | 23.17 |
| 24.6446 | 1608.97 | 0.1279 | 3.61245 | 100.00 |
| 25.6285 | 243.78 | 0.1151 | 3.47596 | 15.15 |
| 26.1758 | 202.33 | 0.1279 | 3.40451 | 12.58 |
| 27.9112 | 140.83 | 0.1279 | 3.19666 | 8.75 |
| 28.3172 | 287.92 | 0.0895 | 3.15174 | 17.89 |
| 28.6091 | 117.85 | 0.1535 | 3.12024 | 7.32 |
| 29.2966 | 84.22 | 0.1791 | 3.04857 | 5.23 |
| 31.1585 | 113.96 | 0.1535 | 2.87052 | 7.08 |
| 32.4190 | 24.17 | 0.2047 | 2.76173 | 1.50 |
| 32.9906 | 98.16 | 0.1023 | 2.71517 | 6.10 |
| 33.8751 | 115.38 | 0.1279 | 2.64627 | 7.17 |

The solids were isolated with an 80% yield. The isolated solids had a chemical purity of 96.4% area, by HPLC.

The theoretical yield, based on losses to mother liquor and wash liquors, was 99%. The mother liquor and wash liquor concentrations were 0.3 mg/mL.

Figure 19:
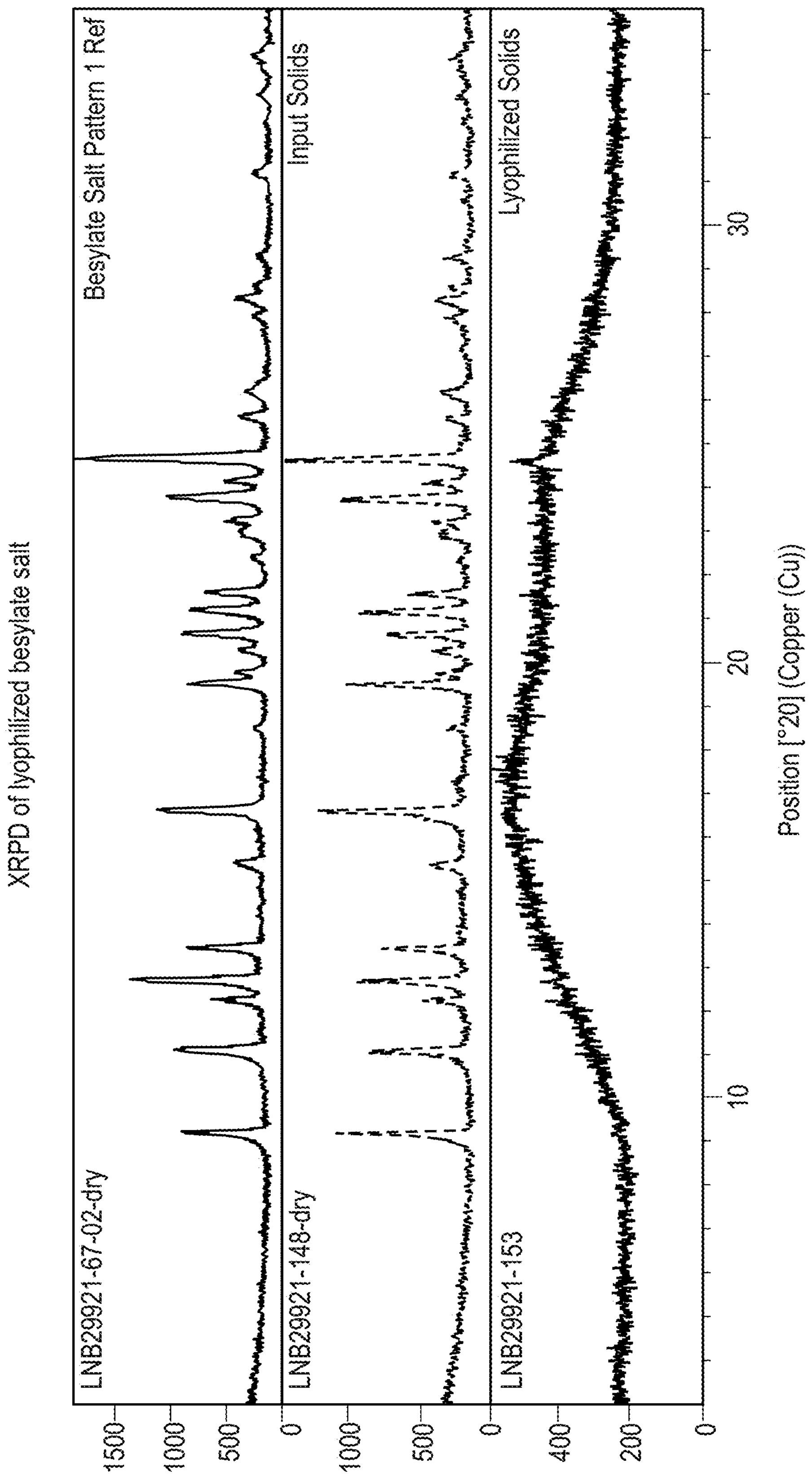
FIG. 19 shows an XRPD of lyophilized besylate salt.

FIG. 19 demonstrates the lyophilized material was predominantly amorphous, there was one peak at 24.7° 2θ in the isolated material which is consistent with besylate salt Pattern 1.

Conclusion

The mesembrine besylate salt Pattern 1 was fully characterised by the XRPD analysis demonstrating a novel form of mesembrine salt with superior properties which are able to be lyophilised to produce an amorphous material suitable for use in the preparation of pharmaceutical compositions.

Example 9: Solubility Screen for Mesembrine Besylate Salt

Materials and Methods

The amorphous besylate salt prepared in Example 8 was used in a solubility screen as follows:

Known volume aliquots of solvent system were added to each vial, with heating at 40° C. between each addition for ca. 5 minutes. Addition of solvents was continued until either dissolution was observed, or until 100 volumes (ca. 1 mL) had been added.

After the solvent addition was complete, the experiments were stirred at 40° C. for ca. 16 h. Slurries were stirred at 40° C. and clear solutions were left to evaporate at 40° C., at ambient pressure for ca. 24 h. The solids were isolated by centrifuge filtration and were analysed by XRPD.

Clear solutions were left to evaporate at 40° C. under vacuum, for ca. 72 h. Any solids isolated were analysed by XRPD.

Results

The results of the solubility screen are summarized in Table 3.11 below.

TABLE 3.11

Solubility screen of amorphous besylate salt

| No. | Solvent System/% v/v | Solubility/mg/mL | XRPD |
|---|---|---|---|
| 1 | 1,4-Dioxane | <10 | A |
| 2 | 1-Butanol | <10 | A |
| 3 | 1-Propanol | ca.31 | 1, C |
| 4 | 2-Ethoxyethanol | ca.44 | 1, PC |
| 5 | 2-Methyl THF | <10 | 1, C |
| 6 | 2-Propanol | <10 | 1, C |
| 7 | 2-Propanol:Water (50:50) | >500 | n/a |
| 8 | 2-Propanol:Water (75:25) | ca.167 | n/a |
| 9 | Acetone | <10 | 1, C |
| 10 | Acetone:Water (90:10) | >500 | 1, PC |
| 11 | Acetonitrile | >500 | A |
| 12 | Anisole | <10 | A |
| 13 | Butyl Acetate | <10 | A |
| 14 | Dichloromethane (DCM) | ca.250 | n/a |
| 15 | Diisopropyl ether | <10 | n/a |
| 16 | Dimethylsulfoxide (DMSO) | >500 | n/a |
| 17 | Ethanol | ca.44 | 1, C |
| 18 | Ethanol:Water (50:50) | >500 | n/a |
| 19 | Ethanol:Water (90:10) | >500 | 1, PC |
| 20 | Ethyl Acetate | <10 | 1, C |
| 21 | Heptane | <10 | n/a |

TABLE 3.11-continued

| Solubility screen of amorphous besylate salt | | | |
|---|---|---|---|
| 22 | Isopropyl Acetate | <10 | 1, PC |
| 23 | Methanol | >500 | n/a |
| 24 | Methylethyl Ketone (MEK) | <10 | 1, PC |
| 25 | Methylisobutyl Ketone (MiBK) | <10 | A |
| 26 | N,N-Dimethylacetamide (DMA) | >500 | 2, C |
| 27 | N,N-Dimethylformamide (DMF) | ca.250 | 1, C |
| 28 | N-Methylpyrrolidone (NMP) | >500 | n/a |
| 29 | tert-Butylmethyl Ether (tBME) | <10 | n/a |
| 30 | Tetrahydrofuran (THF) | <10 | A |
| 31 | Toluene | <10 | A |
| 32 | Water | >500 | n/a |

Key

| | | | |
|---|---|---|---|
| A | Amorphous | 1 | Besylate salt Pattern 1 |
| C | Crystalline salt | 2 | Besylate salt Pattern 2 |
| PC | Poorly crystalline | | |

The solubility screen demonstrated that in addition to the besylate salt pattern 1 an additional salt pattern 2 was formed in DMA.

Conclusion

The amorphous material is soluble in many solvent systems and is capable of forming an additional polymorph described as besylate salt pattern 2.

Example 10: Polymorph Screen for Mesembrine Besylate Salt

Materials and Methods

The amorphous besylate salt prepared in Example 8 was used as the input for this set of experiments.

Approximately 1.25 g of besylate salt was weighed and dissolved in 17.5 mL of water. The solution was split across 25×2 mL vials and frozen. The frozen material was Lyophilized for ca. 24 h. The isolated solids were dried at 20° C. under vacuum for ca. 24 h. The dried solids were analysed by XRPD.

Solvent was added to each vial to obtain a slurry. If dissolution was observed more amorphous material was added to try and produce a slurry.

The experiments were temperature cycled between 30° C. and 5° C. at 0.1° C./min with 1 h holds at 30° C. and 5° C., for 48 h. After 48 h, solids were isolated from slurries at 30° C. by centrifuge filtration and analysed by XRPD. The solids were then dried at 40° C. under vacuum for 18 h. The clear solutions were cooled to 5° C. over 10 minutes and held for 30 minutes to attempt to induce precipitation.

Results

The results of the solubility screen are summarized in Table 3.12 below.

TABLE 3.12

Polymorph screen of amorphous besylate salt

| No. | Solvent System/% v/v | Observation at end of experiment | XRPD (damp) |
|---|---|---|---|
| 1 | 1,4-Dioxane | Slurry | 1, C |
| 2 | 1-Butanol | Clear solution | — |
| 3 | 1-Propanol | Slurry | 2, C |
| 4 | 2-Ethoxyethanol | Slurry | 2, C |
| 5 | 2-Methyl THF | Slurry | 1 + 2, C |
| 6 | 2-Propanol | Slurry | 2, C |
| 7 | 2-Propanol:Water (75:25) | Clear solution | — |
| 8 | Acetone | Slurry | 1 + 2, C |
| 9 | Acetonitrile:Ethyl acetate (50:50) | Slurry | 2, C |
| 10 | Anisole | Slurry | 1 + 2, C |
| 11 | Dichloromethane (DCM) | Slurry | 2, C |
| 12 | DCM:tBME (50:50) | Slurry | 2, C |
| 13 | DMSO:Ethyl acetate (50:40) | Clear solution | — |
| 14 | Ethanol | Clear solution | — |
| 15 | Ethanol:Water (95:5) | Slurry | 2, C |
| 16 | Ethyl acetate | Slurry | 1, C |
| 17 | Isopropyl Acetate | Slurry | 1 + 2, C |
| 18 | Methanol:Ethyl acetate (50:50) | Clear solution | — |
| 19 | Methylethyl Ketone (MEK) | Slurry | 1, C |
| 20 | Methylisobutyl Ketone (MiBK) | Slurry | 1 + 2, C |
| 21 | NMP:tBME (50:50) | Slurry | 2, C |
| 22 | Tetrahydrofuran (THF) | Slurry | 1, C |
| 23 | Toluene | Solids on vial base | 2, C |
| 24 | Water | Clear solution | — |

Key

| | | | |
|---|---|---|---|
| — | No solids | 1 | Besylate salt Pattern 1 |
| C | Crystalline salt | 2 | Besylate salt Pattern 2 |

As shown, many of the solvent systems were able to produce either of the polymorphs besylate salt pattern 1 or besylate salt pattern 2. Furthermore, some systems produced a mixture of both salt patterns.

Figure 20:
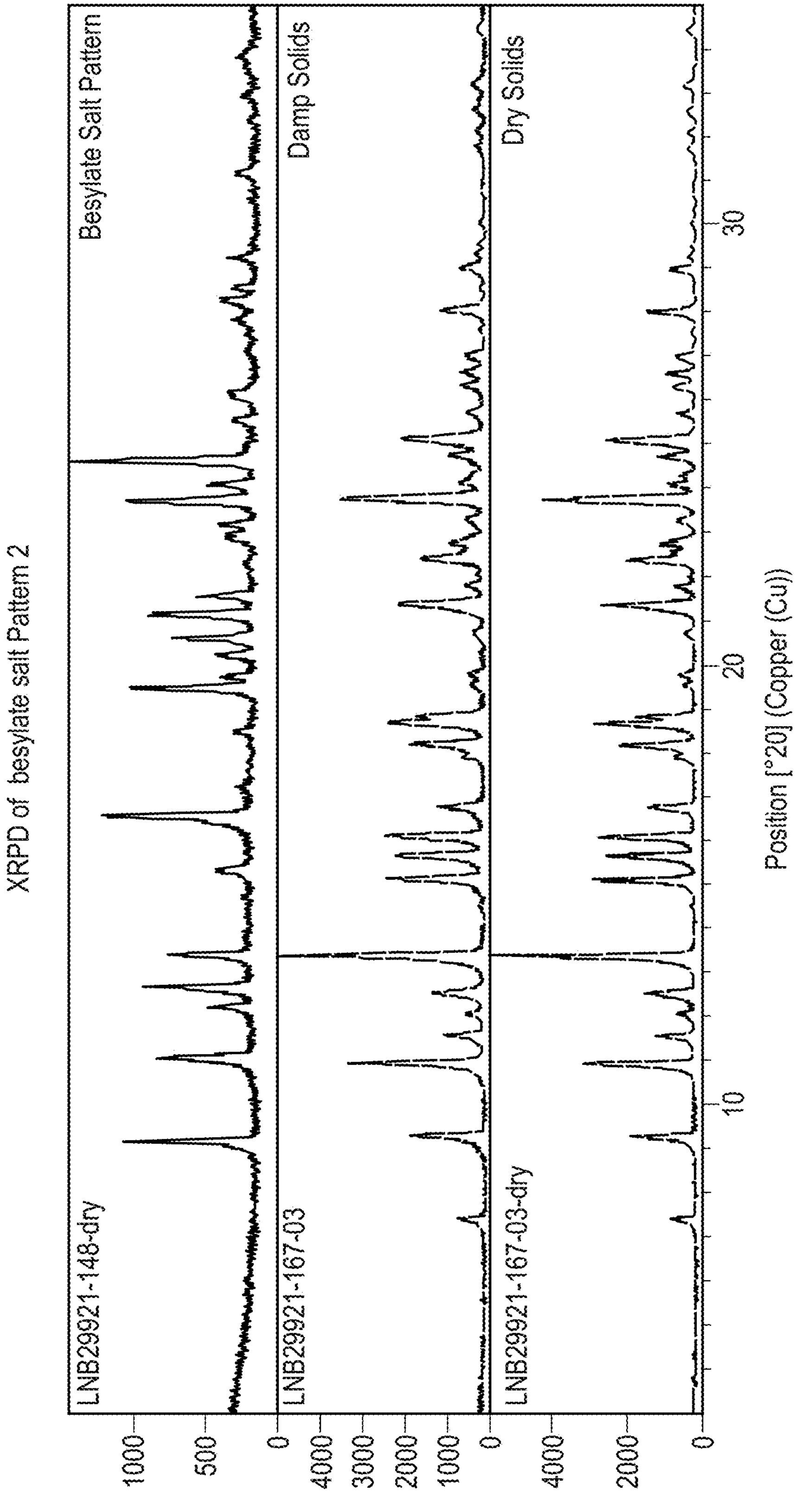
FIG. 20 shows an XRPD of besylate salt Pattern 2.
Figure 21:
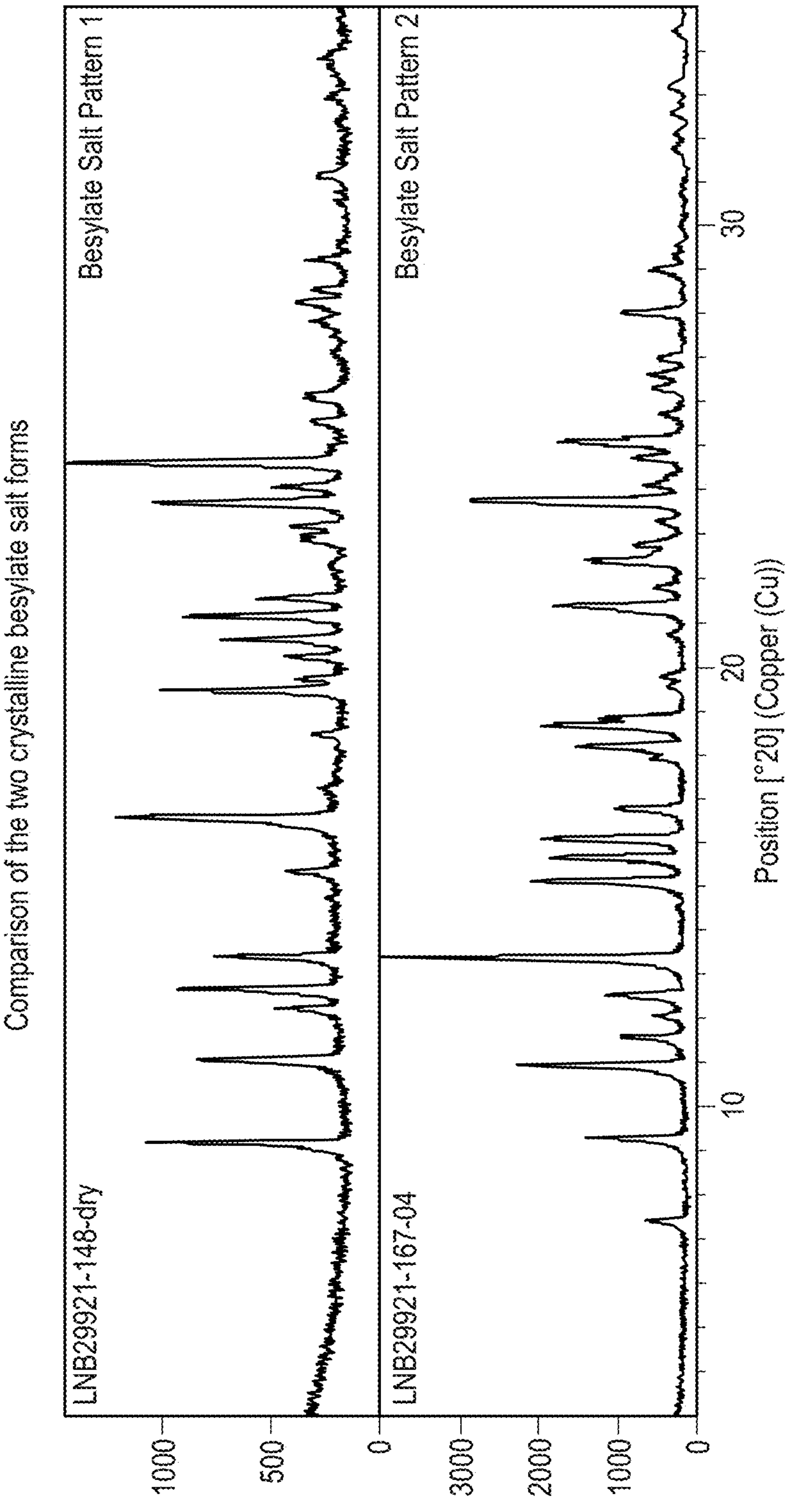
FIG. 21 shows a comparison of the two crystalline besylate salt forms.

The novel polymorph besylate salt pattern 2 was further characterised by XRPD as shown in FIG. 20 with peak positions and heights as specified in Table 3.13 below. A comparison of the two crystalline forms Pattern 1 and Pattern 2 is additionally shown in FIG. 21.

TABLE 3.13

XRPD Peaks for Besylate Salt Pattern 2

| Pos. [°2θ] | Height [cts] | FWHM Left [°2θ] | d-spacing [Å] | Rel. Int. [%] |
|---|---|---|---|---|
| 3.2456 | 58.55 | 0.6140 | 27.22259 | 1.10 |
| 7.4271 | 684.03 | 0.0768 | 11.90295 | 12.88 |
| 9.3019 | 1717.10 | 0.0895 | 9.50775 | 32.34 |
| 10.9620 | 2816.81 | 0.0895 | 8.07130 | 53.06 |
| 11.5879 | 1065.97 | 0.0768 | 7.63675 | 20.08 |
| 12.0804 | 494.59 | 0.0640 | 7.32648 | 9.32 |
| 12.5619 | 1305.28 | 0.0768 | 7.04670 | 24.59 |
| 13.4046 | 5309.08 | 0.0895 | 6.60552 | 100.00 |
| 14.5243 | 135.29 | 0.1023 | 6.09873 | 2.55 |
| 15.1300 | 2692.72 | 0.1023 | 5.85592 | 50.72 |
| 15.6466 | 2424.16 | 0.0895 | 5.66374 | 45.66 |
| 16.0986 | 2570.30 | 0.1023 | 5.50572 | 48.41 |
| 16.7575 | 1253.30 | 0.0895 | 5.29069 | 23.61 |
| 17.8837 | 528.70 | 0.0895 | 4.95996 | 9.96 |
| 18.1790 | 2068.20 | 0.1023 | 4.88006 | 38.96 |
| 18.6461 | 2663.26 | 0.0895 | 4.75884 | 50.16 |
| 18.8174 | 1606.35 | 0.0895 | 4.71591 | 30.26 |
| 19.5339 | 314.34 | 0.0768 | 4.54452 | 5.92 |
| 19.7767 | 438.54 | 0.0895 | 4.48928 | 8.26 |
| 20.7293 | 291.48 | 0.0895 | 4.28508 | 5.49 |
| 21.3589 | 2518.45 | 0.1151 | 4.16015 | 47.44 |
| 21.7748 | 573.67 | 0.0895 | 4.08164 | 10.81 |
| 22.3767 | 1835.92 | 0.1023 | 3.97319 | 34.58 |
| 22.5713 | 656.22 | 0.0512 | 3.93937 | 12.36 |
| 22.7318 | 843.79 | 0.0768 | 3.91192 | 15.89 |
| 23.2719 | 506.24 | 0.1023 | 3.82234 | 9.54 |
| 23.7453 | 4139.90 | 0.1151 | 3.74719 | 77.98 |
| 24.1138 | 719.19 | 0.1023 | 3.69076 | 13.55 |
| 24.2892 | 374.86 | 0.0895 | 3.66451 | 7.06 |
| 24.7259 | 1014.59 | 0.0895 | 3.60077 | 19.11 |
| 25.0993 | 2369.88 | 0.1023 | 3.54804 | 44.64 |
| 25.6893 | 456.57 | 0.1279 | 3.46787 | 8.60 |
| 26.2905 | 586.92 | 0.0624 | 3.38711 | 11.06 |
| 26.3404 | 538.09 | 0.0468 | 3.38921 | 10.14 |
| 26.6066 | 757.13 | 0.1248 | 3.34759 | 14.26 |
| 26.9884 | 521.57 | 0.1092 | 3.30108 | 9.82 |
| 27.5335 | 113.88 | 0.1872 | 3.23696 | 2.15 |
| 28.0252 | 1249.17 | 0.1404 | 3.18128 | 23.53 |
| 28.4998 | 96.44 | 0.0936 | 3.12937 | 1.82 |
| 28.9700 | 692.95 | 0.1560 | 3.07964 | 13.05 |
| 29.2870 | 191.82 | 0.1248 | 3.04702 | 3.61 |
| 29.5248 | 138.56 | 0.1560 | 3.02302 | 2.61 |
| 30.0582 | 97.15 | 0.1092 | 2.97058 | 1.83 |
| 30.6912 | 98.55 | 0.1248 | 2.91073 | 1.86 |
| 31.6949 | 208.95 | 0.1560 | 2.82081 | 3.94 |
| 32.0814 | 219.67 | 0.0780 | 2.78770 | 4.14 |
| 32.5443 | 243.64 | 0.1404 | 2.74910 | 4.59 |
| 33.0909 | 289.14 | 0.0624 | 2.70493 | 5.45 |
| 33.4658 | 66.36 | 0.1248 | 2.67548 | 1.25 |
| 34.4144 | 241.94 | 0.1872 | 2.60388 | 4.56 |

Conclusion

The amorphous material is capable of forming two different forms; characterized as besylate salt pattern 1 and besylate salt pattern 2.

Example 11: Pharmacokinetic Analysis of Mesembrine Besylate Salt

Materials and Methods

The amorphous besylate salt prepared in Example 8 was used in addition to mesembrine free base in this example to determine the pharmacokinetic (PK) characteristics of the two.

Groups of 18 male C57Bl/6J mice (weighing between 20 and 30 g) received a single administration of test compound (10 mg/kg; i.p.) in methylcellulose (0.5% w/v) at a nominal concentration of 1.0 ng/mL.

Three mice from each dose group were subject to cardiac puncture under general anaesthesia at 0.25, 0.50, 1.00, 1.50, 2.00 and 4.00 hrs post-dose and plasma samples generated for application of standard LC-MS/MS bioanalytical methods.

Quantification of compound concentration was derived from reference calibration data. Pharmacokinetic data were derived from serial plasma concentrations.

Results

Table 4 details the PK parameters measured using either the mesembrine besylate salt or the free base mesembrine.

Figure 22:
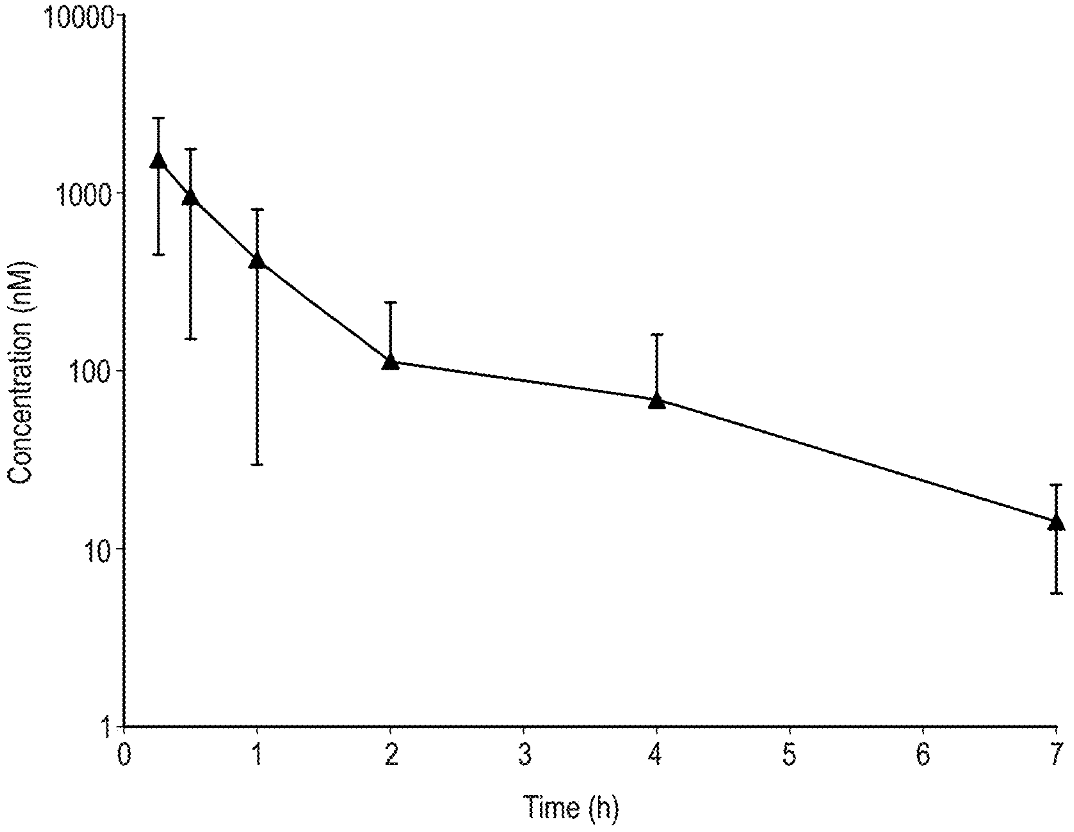
FIG. 22 shows the mean total concentrations of mesembrine besylate salt following IP administration to male C57Bl/6J mouse at 10.0 mg/kg.
Figure 23:
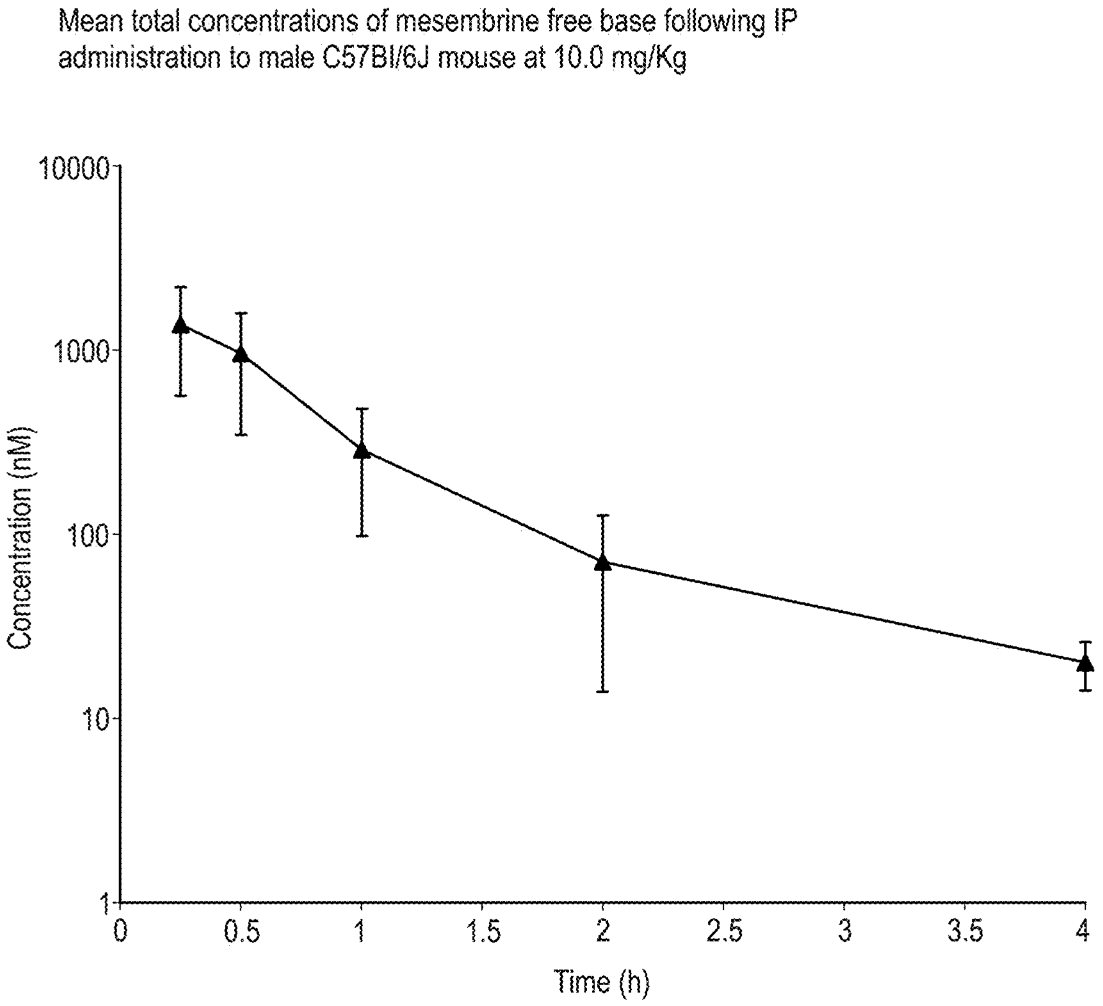
FIG. 23 shows the mean total concentrations of free base following IP administration to male C57Bl/6J mouse at 10.0 mg/kg.

FIGS. 22 and 23 detail the mean total concentrations of mesembrine besylate salt and mesembrine free base respectively.

TABLE 4

Summary of PK parameters

| Compound | $C_{max}$ (ng/mL) | $T_{max}$ (hr) | $AUC_{0\text{-}inf}$ (ng · hr/mL) | $t_{1/2}$ (hr) |
|---|---|---|---|---|
| Mesembrine free base | 400 | 0.25 | 290 | 0.454 |
| Mesembrine besylate salt | 451 | 0.25 | 392 | 0.615 |

Both mesembrine besylate salt and free base demonstrated a short $T_{max}$ at only 15 minutes, however the half-life of the besylate salt was substantially longer for the besylate salt form of mesembrine than the free base. Here it was seen that the besylate salt had a half-life of 36.9 minutes whereas the free base was 27.2 minutes, a difference of almost 10 minutes.

Different $C_{max}$ and AUCs were also found for the two forms of mesembrine. The $C_{max}$ and AUC were both found to be larger in the mesembrine besylate salt than in the free base. With respect to the AUC the mesembrine besylate salt produced an AUC of over 100 ng·hr/mL greater than that produced by the mesembrine free base.

Table 5 below details the blood:plasma ratio and the blood:brain ratios observed in both the mesembrine besylate salt and the free base in a separate cohort of satellite animals dosed in the same way but sacrificed at t=0.25 h to obtain brain samples.

TABLE 5

| Summary of mean ratios | | | | |
|---|---|---|---|---|
| Compound | Mean blood:plasma ratio | Mean blood:brain ratio | Plasma concentration (ng/ml) | Brain concentration (ng/g) |
| Mesembrine free base | 0.895 | 0.357 | 317 | 1292 |
| Mesembrine besylate salt | 1.023 | 0.395 | 417 | 814 |

As detailed above, plasma concentrations of besylate salt are greater than those observed with free base, consistent with the observations described in Table 4. Moreover, higher brain exposure was observed in the animals dosed with besylate salt when compared to free base. The mesembrine besylate salt resulted in a higher mean blood to plasma ratio than the free base. Such a difference infers that the salt form is able to enter the plasma at a greater concentration than the free base.

Conclusion

The ability of the mesembrine besylate salt to preferentially improve the PK properties of the mesembrine free salt demonstrates the importance of using the salt form of mesembrine in pharmaceutical preparations.

The improvement of PK properties demonstrated by the besylate salt form of mesembrine will enable more of the active to be absorbed and as such a smaller dose of drug can be given. Advantages of this includes a lower cost of active ingredient due to a smaller amount being required to obtain the same effect and also potentially fewer side effects for the patient due to a lower dose of drug being required.

Overall Conclusion

The Examples 1 to 10 presented above demonstrate that alternative salt forms of mesembrine can be formed using various counterions. The HCl salt is known in the art however there are distinct problems with this salt form as it is only able to solubilise to form a clear solution at relatively low concentrations of mesembrine. This physicochemical property renders the hydrochloride salt unsuitable for development of a pharmaceutical as only low doses of mesembrine could be delivered.

However, the besylate salt was found to be highly soluble resulting in a solubility of greater than 1000 mg/ml, providing evidence that this salt is highly suitable for development of a pharmaceutical composition.

Such a finding is surprising as often salts formed from benzenesulfonic acid are rarely found as being of use in active pharmaceutical ingredients. Hydrochloride salts are the most commonly found pharmaceutical salts and are found in approximately 15.5% of all approved medicinal compounds. Sodium and sulphate salts are also found in 9% and 4% of all medicinal compounds respectively.

The finding that a besylate salt was the most soluble and stable salt in comparison to the hydrochloride and fumarate salts was additionally surprising given the relatively high pKa of benzenesulfonic acid, particularly in comparison to hydrochloric acid. As described in Example 3, a weak acid is unlikely to form a suitable salt due to the inability to complete the proton transfer.

In the formulation of drug compositions, it is important for the active pharmaceutical ingredient (API) to be in a form in which it can be conveniently handled and processed. This is of importance, not only from the point of view of obtaining a commercially viable manufacturing process, but also from the point of view of subsequent manufacture of pharmaceutical formulations (e.g., oral dosage forms such as tablets) comprising the active pharmaceutical ingredient.

In the manufacture of oral drug compositions, it is important that a reliable, reproducible and constant plasma concentration profile of the active pharmaceutical ingredient is provided following administration to a patient.

Chemical stability, solid state stability, and the shelf life of the active pharmaceutical ingredient are also very important factors in the consideration of the form to use for preparation of the pharmaceutical.

Amorphous materials, such as mesembrine, are typically more difficult to handle and to formulate and are often unstable. Therefore, the mesembrine besylate salt provides a form which can be used in the manufacture of commercially viable and pharmaceutically acceptable drug compositions, as it has been shown to occur as a substantially crystalline and stable form, which is highly soluble.

Furthermore, the data presented in Example 11 demonstrates that the besylate salt of the invention was able to produce preferential pharmacokinetic properties than mesembrine free base.

NUMBERED EMBODIMENTS

1. A mesembrine salt, wherein the salt is taken from the group consisting of mesembrine besylate; mesembrine phosphate; mesembrine tartrate; mesembrine fumarate and mesembrine succinate.
2. A mesembrine salt according to embodiment 1, wherein the salt is mesembrine besylate salt.
3. A mesembrine salt according to embodiment 1 or embodiment 2, wherein the salt is in a solid form.
4. A mesembrine salt according to any of the preceding embodiments, wherein the salt is in a crystalline form.
5. A mesembrine salt according to embodiment 2, characterized by an XRPD pattern substantially similar to FIG. 18.
6. A mesembrine salt according to embodiment 5, characterized by an XRPD pattern comprising peaks at about the positions as described in Table 3.10.
7. A mesembrine salt according to embodiment 2, characterized by an XRPD pattern substantially similar to FIG. 20.
8. A mesembrine salt according to embodiment 7, characterized by an XRPD pattern comprising peaks at about the positions as described in Table 3.13.
9. A mesembrine salt according to embodiment 4, wherein the crystalline form is characterized by peaks in an XPRD pattern at 11.1±0.2, 12.7±0.2, 16.6±0.2, 23.8±0.2, and 24.6±0.2°2θ.
10. The mesembrine salt according to embodiment 9, further characterized by at least one peak selected from 9.2±0.2, 11.0±0.2, 13.5±0.2, 19.5±0.2, 20.7±0.2, and 21.2±0.2°2θ.
11. The mesembrine salt according to embodiment 4, wherein the crystalline form is characterized by peaks in a XRPD pattern at 9.2±0.2, 11.0±0.2, 11.1±0.2, 12.3±0.2, 12.7±0.2, 13.5±0.2, 15.4±0.2, 16.6±0.2, 18.5±0.2, 19.5±0.2, 19.8±0.2, 20.2±0.2, 20.7±0.2, 21.2±0.2, 21.6±0.2, 22.4±0.2, 22.9±0.2, 23.2±0.2, 23.8±0.2, 24.1±0.2, 24.6±0.2, 25.6±0.2, 26.2±0.2, 27.9±0.2, 28.3±0.2, 28.6±0.2, 29.3±0.2, 31.1±0.2, 32.4±0.2, 33.0±0.2, and 33.9±0.2°2θ.

12. The mesembrine salt according to embodiment 4, wherein the crystalline form is characterized by peaks in a XPRD pattern at 11.0±0.2, 13.4±0.2, 15.1±0.2, 18.6±0.2, or 23.7±0.2°2θ.
13. The mesembrine salt according to embodiment 12, further characterized by at least one peak selected from 15.6±0.2, 16.1±0.2, 18.2±0.2, 21.3±0.2, or 25.1±0.2°2θ.
14. The mesembrine salt according to embodiment 4, wherein the crystalline form is characterized by peaks in a XRPD pattern at 3.2±0.2, 7.4±0.2, 9.3±0.2, 11.0±0.2, 11.6±0.2, 12.1±0.2, 12.6±0.2, 13.4±0.2, 14.5±0.2, 15.1±0.2, 15.6±0.2, 16.1±0.2, 16.8±0.2, 17.9±0.2, 18.2±0.2, 18.6±0.2, 18.8±0.2, 19.5±0.2, 19.8±0.2, 20.7±0.2, 21.3±0.2, 21.8±0.2, 22.4±0.2, 22.6±0.2, 22.7±0.2, 23.3±0.2, 23.7±0.2, 24.1±0.2, 24.3±0.2, 24.7±0.2, 25.1±0.2, 25.7±0.2, 26.3±0.2, 26.6±0.2, 27.0±0.2, 27.5±0.2, 28.0±0.2, 28.5±0.2, 29.0±0.2, 29.3±0.2, 29.5±0.2, 30.0±0.2, 30.7±0.2, 31.7±0.2, 32.1±0.2, 32.5±0.2, 33.1±0.2, 33.5±0.2, and 34.4±0.2°2θ.
15. A process for the preparation of a mesembrine salt comprising the steps of:
  a) Dissolving mesembrine in a solvent;
  b) Addition of the appropriate counterion to the mesembrine solution under temperature cycling conditions; and
  c) Isolation of solids comprising the mesembrine salt.
16. A process according to claim 15, wherein the counterion of step b) is benzenesulfonic acid.
17. A pharmaceutical preparation comprising a mesembrine salt, wherein the salt is taken from the group consisting of mesembrine besylate; mesembrine phosphate; mesembrine tartrate; mesembrine fumarate and mesembrine succinate.
18. A pharmaceutical preparation according to embodiment 17, wherein the salt is mesembrine besylate.
19. A pharmaceutical preparation according to either embodiment 17 or claim 18, wherein the preparation produces an elevated blood level of mesembrine of between 80% and 125% compared to those obtained with a pharmaceutical preparation not comprising a salt form of mesembrine.
20. A mesembrine salt for use in the treatment of a disease, wherein the salt is taken from the group consisting of mesembrine besylate; mesembrine phosphate; mesembrine tartrate; mesembrine fumarate and mesembrine succinate.
21. A mesembrine salt for use according to embodiment 20, wherein the salt is mesembrine besylate.

The invention claimed is:

1. A method of treating sexual dysfunction in a subject in need thereof, the method comprising administering to the subject a besylate salt of mesembrine.

2. The method of claim 1, wherein treating sexual dysfunction in the subject delays ejaculation, delays orgasms, prevents premature ejaculation, or combinations thereof in the subject.

3. The method of claim 1, wherein the besylate salt of mesembrine is crystalline.

4. The method of claim 3, wherein the besylate salt of mesembrine is characterized by peaks in an XPRD pattern at 11.1±0.2, 12.7±0.2, 16.6±0.2, 23.8±0.2, and 24.6±0.2°2θ.

5. The method of claim 4, wherein the besylate salt of mesembrine is further characterized by at least one peak selected from 9.2±0.2, 11.0±0.2, 13.5±0.2, 19.5±0.2, 20.7±0.2, and 21.2±0.2°2θ.

6. The method of claim 4, wherein the besylate salt of mesembrine is further characterized by peaks in a XRPD pattern at 9.2±0.2, 11.0±0.2, 12.3±0.2, 13.5±0.2, 15.4±0.2, 18.5±0.2, 19.5±0.2, 19.8±0.2, 20.2±0.2, 20.7±0.2, 21.2±0.2, 21.6±0.2, 22.4±0.2, 22.9±0.2, 23.2±0.2, 24.1±0.2, 25.6±0.2, 26.2±0.2, 27.9±0.2, 28.3±0.2, 28.6±0.2, 29.3±0.2, 31.1±0.2, 32.4±0.2, 33.0±0.2, and 33.9±0.2°2θ.

7. The method of claim 3, wherein the besylate salt of mesembrine is further characterized by at least two peaks selected from 9.2±0.2, 11.0±0.2, 13.5±0.2, 19.5±0.2, 20.7±0.2, and 21.2±0.2°2θ.

8. The method of claim 3, wherein the besylate salt of mesembrine is further characterized by at least three peaks selected from 9.2±0.2, 11.0±0.2, 13.5±0.2, 19.5±0.2, 20.7±0.2, and 21.2±0.2°2θ.

9. The method of claim 3, wherein the besylate salt of mesembrine is further characterized by at least four peaks selected from 9.2±0.2, 11.0±0.2, 13.5±0.2, 19.5±0.2, 20.7±0.2, and 21.2±0.2°2θ.

10. The method of claim 3, wherein the besylate salt of mesembrine is further characterized by at least five peaks selected from 9.2±0.2, 11.0±0.2, 13.5±0.2, 19.5±0.2, 20.7±0.2, and 21.2±0.2°2θ.

11. The method of claim 3, wherein the besylate salt of mesembrine is further characterized by peaks at 9.2±0.2, 11.0±0.2, 13.5±0.2, 19.5±0.2, 20.7±0.2, and 21.2±0.2°2θ.

12. The method of claim 3, besylate salt of mesembrine is characterized by at least one peak selected from 11.1±0.2, 12.3±0.2, 12.7±0.2, 15.4±0.2, 16.6±0.2, 18.5±0.2, 19.8±0.2, 20.2±0.2, 21.6±0.2, 22.4±0.2, 22.9±0.2, 23.2±0.2, 23.8±0.2, 24.1±0.2, 24.6±0.2, 25.6±0.2, 26.2±0.2, 27.9±0.2, 28.3±0.2, 28.6±0.2, 29.3±0.2, 31.1±0.2, 32.4±0.2, 33.0±0.2, and 33.9±0.2°2θ.

13. The method of claim 3, besylate salt of mesembrine is characterized by at least two peaks selected from 11.1±0.2, 12.3±0.2, 12.7±0.2, 15.4±0.2, 16.6±0.2, 18.5±0.2, 19.8±0.2, 20.2±0.2, 21.6±0.2, 22.4±0.2, 22.9±0.2, 23.2±0.2, 23.8±0.2, 24.1±0.2, 24.6±0.2, 25.6±0.2, 26.2±0.2, 27.9±0.2, 28.3±0.2, 28.6±0.2, 29.3±0.2, 31.1±0.2, 32.4±0.2, 33.0±0.2, and 33.9±0.2°2θ.

14. The method of claim 3, besylate salt of mesembrine is characterized by at least three peaks selected from 11.1±0.2, 12.3±0.2, 12.7±0.2, 15.4±0.2, 16.6±0.2, 18.5±0.2, 19.8±0.2, 20.2±0.2, 21.6±0.2, 22.4±0.2, 22.9±0.2, 23.2±0.2, 23.8±0.2, 24.1±0.2, 24.6±0.2, 25.6±0.2, 26.2±0.2, 27.9±0.2, 28.3±0.2, 28.6±0.2, 29.3±0.2, 31.1±0.2, 32.4±0.2, 33.0±0.2, and 33.9±0.2°2θ.

15. The method of claim 3, besylate salt of mesembrine is characterized by at least four peaks selected from 11.1±0.2, 12.3±0.2, 12.7±0.2, 15.4±0.2, 16.6±0.2, 18.5±0.2, 19.8±0.2, 20.2±0.2, 21.6±0.2, 22.4±0.2, 22.9±0.2, 23.2±0.2, 23.8±0.2, 24.1±0.2, 24.6±0.2, 25.6±0.2, 26.2±0.2, 27.9±0.2, 28.3±0.2, 28.6±0.2, 29.3±0.2, 31.1±0.2, 32.4±0.2, 33.0±0.2, and 33.9±0.2°2θ.

16. The method of claim 1, wherein the besylate salt of mesembrine is administered as a pharmaceutical composition.

17. The method of claim 1, comprising orally administering to the subject the besylate salt of mesembrine.

18. The method of claim 1, comprising administering about 1 mg to about 500 mg of the besylate salt of mesembrine to the subject.

* * * * *